United States Patent
Burns et al.

(10) Patent No.: US 10,010,673 B2
(45) Date of Patent: Jul. 3, 2018

(54) ADJUSTABLE MEDIUM DIVERTER

(71) Applicants: Matthew M. Burns, Deephaven, MN (US); Tuan M. Doan, Burnsville, MN (US); Rodney L. Houfburg, Prior Lake, MN (US); David M. Kaye, Beaumaris (AU); Todd J. Mortier, Mound, MN (US)

(72) Inventors: Matthew M. Burns, Deephaven, MN (US); Tuan M. Doan, Burnsville, MN (US); Rodney L. Houfburg, Prior Lake, MN (US); David M. Kaye, Beaumaris (AU); Todd J. Mortier, Mound, MN (US)

(73) Assignee: Osprey Medical, Inc., Minnetonka, MN (US)

( * ) Notice: Subject to any disclaimer, the term of this patent is extended or adjusted under 35 U.S.C. 154(b) by 30 days.

(21) Appl. No.: 14/851,939

(22) Filed: Sep. 11, 2015

(65) Prior Publication Data

US 2016/0106915 A1    Apr. 21, 2016

Related U.S. Application Data

(63) Continuation-in-part of application No. 13/839,771, filed on Mar. 15, 2013, now Pat. No. 9,320,846.

(Continued)

(51) Int. Cl.
*A61M 5/168* (2006.01)
*A61M 39/24* (2006.01)
(Continued)

(52) U.S. Cl.
CPC ........ *A61M 5/16881* (2013.01); *A61M 5/007* (2013.01); *A61M 5/14212* (2013.01);
(Continued)

(58) Field of Classification Search
CPC ........ A61M 5/48; A61M 5/482; A61M 5/488; A61M 5/484; A61M 5/16881;
(Continued)

(56) References Cited

U.S. PATENT DOCUMENTS 3,469,578 A    9/1969  Bierman
3,543,759 A   12/1970  McWhorter
(Continued)

FOREIGN PATENT DOCUMENTS

EP    1930603 A1   6/2008
WO   84/01718 A1   5/1984
(Continued)

OTHER PUBLICATIONS

Search Report and Written Opinion dated Dec. 11, 2015 for International Application No. PCT/US2015/049691, filed Sep. 11, 2015, 14 pages.

(Continued)

*Primary Examiner* — Bradley J Osinski
*Assistant Examiner* — Nilay Shah
(74) *Attorney, Agent, or Firm* — Mai-Tram D. Lauer; Westman, Champin & Koehler, P.A.

(57) ABSTRACT

A system for modulating delivery of a fluid medium to a selected site within a patient's body includes a syringe for injecting the fluid medium, a delivery catheter including a conduit for delivering the fluid medium from outside of the body to the selected site within the body, a medium reservoir configured to receive a portion of the fluid medium, and a flow diverter assembly disposed in a fluid medium flow path between the syringe and the delivery catheter. The syringe includes a chamber for receiving the fluid medium therein. The flow diverter assembly is configured to divert the portion of the fluid medium from the chamber of the syringe away from the delivery of the medium through the delivery (Continued)

catheter conduit during injecting with the syringe, and simultaneously increase medium fluid flow resistance with increasing pressure level of the fluid medium within the flow diverter assembly.

3 Claims, 64 Drawing Sheets

Related U.S. Application Data

(60) Provisional application No. 62/048,974, filed on Sep. 11, 2014, provisional application No. 62/082,260, filed on Nov. 20, 2014, provisional application No. 61/694,137, filed on Aug. 28, 2012.

(51) Int. Cl.
| | | |
|---|---|---|
| *A61M 39/12* | (2006.01) | |
| *A61M 5/00* | (2006.01) | |
| *A61M 5/142* | (2006.01) | |
| *F04B 11/00* | (2006.01) | |
| *F04B 49/06* | (2006.01) | |
| *A61M 5/48* | (2006.01) | |
| *F16K 15/00* | (2006.01) | |
| *G06F 19/00* | (2018.01) | |
| *A61M 5/14* | (2006.01) | |

(52) U.S. Cl.
CPC .......... *A61M 5/482* (2013.01); *A61M 5/484* (2013.01); *A61M 5/488* (2013.01); *A61M 39/12* (2013.01); *A61M 39/24* (2013.01); *F04B 11/0033* (2013.01); *F04B 49/06* (2013.01); *A61M 5/14* (2013.01); *A61M 5/14216* (2013.01); *A61M 5/16813* (2013.01); *A61M 5/48* (2013.01); *A61M 2039/2413* (2013.01); *A61M 2205/3331* (2013.01); *A61M 2205/3334* (2013.01); *A61M 2205/3337* (2013.01); *A61M 2205/3341* (2013.01); *A61M 2205/3344* (2013.01); *A61M 2205/3355* (2013.01); *A61M 2206/22* (2013.01); *A61M 2210/125* (2013.01); *A61M 2210/127* (2013.01); *F16K 15/00* (2013.01); *G06F 19/3468* (2013.01)

(58) Field of Classification Search
CPC .......... A61M 39/24; A61M 2039/2413; A61M 2039/242; A61M 2039/2493; A61M 2205/3331; A61M 2205/3341; A61M 2039/2473; A61M 2005/3128; F16K 15/00; F16K 15/026; F16K 15/02
See application file for complete search history.

(56) References Cited

U.S. PATENT DOCUMENTS

| | | |
|---|---|---|
| 3,556,122 A | 1/1971 | Laerdal |
| 3,572,375 A | 3/1971 | Rosenberg |
| 3,610,228 A * | 10/1971 | Temkin ............... A61B 5/02156 600/486 |
| 3,626,978 A | 12/1971 | Hoekstra |
| 3,633,613 A | 1/1972 | Julow |
| 3,661,174 A | 5/1972 | Cripe |
| 3,818,929 A | 6/1974 | Braukmann |
| 3,905,382 A | 9/1975 | Waterston |
| 3,941,149 A | 3/1976 | Mittleman |
| 3,985,141 A | 10/1976 | Stanley et al. |
| 4,000,741 A | 1/1977 | Binard et al. |
| 4,030,497 A | 6/1977 | Binard et al. |
| 4,044,793 A | 8/1977 | Krueger et al. |
| 4,074,714 A | 2/1978 | Binard et al. |
| 4,077,405 A | 3/1978 | Haerten et al. |
| 4,084,606 A | 4/1978 | Mittleman |
| 4,141,379 A | 2/1979 | Manske |
| 4,142,525 A | 3/1979 | Binard et al. |
| 4,147,170 A | 4/1979 | Taylor |
| 4,240,430 A | 12/1980 | Binard et al. |
| 4,289,006 A | 9/1981 | Hallengren |
| 4,318,400 A | 3/1982 | Peery et al. |
| 4,329,985 A | 5/1982 | Bonchek |
| 4,381,006 A | 4/1983 | Genese |
| 4,392,847 A | 7/1983 | Whitney et al. |
| 4,403,988 A | 9/1983 | Binard et al. |
| 4,481,008 A | 11/1984 | Kurtz |
| 4,501,291 A | 2/1985 | Siegrist |
| 4,502,502 A | 3/1985 | Krug |
| 4,550,747 A | 11/1985 | Woodworth et al. |
| 4,602,700 A | 7/1986 | Szabo |
| 4,671,786 A | 6/1987 | Krug |
| 4,744,786 A | 5/1988 | Hooven |
| 4,755,172 A | 7/1988 | Baldwin |
| 4,758,223 A | 7/1988 | Rydell |
| 4,795,431 A | 1/1989 | Walling |
| 4,813,937 A | 3/1989 | Vaillancourt |
| 4,867,743 A | 9/1989 | Vaillancourt |
| 4,997,420 A | 3/1991 | LeFevre |
| 5,059,174 A | 10/1991 | Vaillancourt |
| 5,167,631 A | 12/1992 | Thompson et al. |
| 5,203,771 A | 4/1993 | Melker |
| 5,447,494 A * | 9/1995 | Dorsey, III ......... A61M 1/0084 604/118 |
| 5,460,609 A | 10/1995 | O'Donnell |
| 5,462,526 A | 10/1995 | Barney |
| 5,556,386 A | 9/1996 | Todd |
| 5,573,515 A | 11/1996 | Wilson et al. |
| 5,575,767 A | 11/1996 | Stevens |
| 5,660,205 A | 8/1997 | Epstein |
| 5,685,851 A | 11/1997 | Murphy et al. |
| 5,707,356 A | 1/1998 | Paul |
| 5,785,681 A | 7/1998 | Indravudh |
| 5,799,700 A | 9/1998 | Teh et al. |
| 5,800,397 A | 9/1998 | Wilson et al. |
| 5,806,519 A | 9/1998 | Evans, III et al. |
| 5,827,941 A | 10/1998 | Good et al. |
| 5,840,026 A | 11/1998 | Uber, III et al. |
| 5,840,071 A | 11/1998 | Kriesel et al. |
| 5,882,343 A | 3/1999 | Wilson et al. |
| 5,885,216 A | 3/1999 | Evans, III et al. |
| 5,916,165 A | 6/1999 | Duchon et al. |
| 6,019,747 A | 2/2000 | McPhee |
| 6,086,559 A | 7/2000 | Enk |
| 6,159,180 A | 12/2000 | Kriesel et al. |
| 6,317,623 B1 | 11/2001 | Griffiths et al. |
| 6,397,098 B1 | 5/2002 | Uber, III et al. |
| 6,409,699 B1 | 6/2002 | Ash |
| 6,442,418 B1 | 8/2002 | Evans, III et al. |
| 6,558,125 B1 | 5/2003 | Futterknecht |
| 6,850,792 B2 | 2/2005 | Ohishi |
| 6,866,654 B2 * | 3/2005 | Callan ................. A61M 5/007 604/246 |
| 6,889,074 B2 | 5/2005 | Uber, III et al. |
| 6,901,283 B2 | 5/2005 | Evans, III et al. |
| 6,966,893 B2 | 11/2005 | Holtby et al. |
| 6,969,353 B2 | 11/2005 | Brock-Fisher et al. |
| 6,970,735 B2 | 11/2005 | Uber, III et al. |
| 7,022,107 B1 | 4/2006 | Christensen et al. |
| 7,065,395 B2 | 6/2006 | Lienard et al. |
| 7,094,216 B2 | 8/2006 | Trombley, III et al. |
| 7,270,648 B2 | 9/2007 | Kazemzadeh |
| 7,326,186 B2 | 2/2008 | Trombley, III et al. |
| 7,470,253 B2 | 12/2008 | Kriesel et al. |
| 7,516,760 B2 | 4/2009 | Weber |
| 7,611,503 B2 | 11/2009 | Spohn et al. |
| 7,618,412 B2 | 11/2009 | Chernack |
| 7,678,070 B2 | 3/2010 | Kumar et al. |
| 7,766,885 B2 | 8/2010 | Olsen |
| 7,815,604 B2 | 10/2010 | Massengale et al. |
| 7,925,330 B2 | 4/2011 | Kalafut et al. |
| 7,927,305 B2 | 4/2011 | Yribarren et al. |
| 7,951,129 B2 | 5/2011 | Chinchoy |

(56) References Cited

U.S. PATENT DOCUMENTS

| | | |
|---|---|---|
| 7,955,301 B1 | 6/2011 | McKay |
| 8,147,448 B2 | 4/2012 | Sundar et al. |
| 8,208,994 B2 | 6/2012 | Niethammer |
| 8,295,914 B2 | 10/2012 | Kalafut et al. |
| 8,323,267 B2 | 12/2012 | Haase |
| 8,328,758 B2 | 12/2012 | Childers et al. |
| 8,795,219 B1 | 8/2014 | Al-Rashdan |
| 2001/0039396 A1 | 11/2001 | Kriesel et al. |
| 2002/0128611 A1 | 9/2002 | Kandalaft |
| 2003/0225371 A1 | 12/2003 | Hadzic |
| 2004/0138615 A1* | 7/2004 | Lombardi ............... A61B 90/00 604/118 |
| 2001/4016365 | 8/2004 | Gelfand |
| 2005/0059931 A1 | 3/2005 | Garrison et al. |
| 2005/0165364 A1 | 7/2005 | DiMatteo et al. |
| 2005/0277912 A1 | 12/2005 | John |
| 2006/0178632 A1 | 8/2006 | Trombley, III et al. |
| 2007/0161970 A1 | 7/2007 | Spohn et al. |
| 2008/0004507 A1 | 1/2008 | Williams, Jr. et al. |
| 2008/0147007 A1 | 6/2008 | Freyman et al. |
| 2009/0234231 A1 | 9/2009 | Knight et al. |
| 2010/0076307 A1* | 3/2010 | Spohn ................... A61M 5/007 600/431 |
| 2010/0114064 A1 | 5/2010 | Kalafut et al. |
| 2011/0092828 A1 | 4/2011 | Spohn et al. |
| 2011/0282302 A1 | 11/2011 | Lopez |
| 2012/0024987 A1 | 2/2012 | Nacken |
| 2012/0116217 A1 | 5/2012 | Lee-Sepsick et al. |
| 2012/0277661 A1 | 11/2012 | Bernard et al. |
| 2012/0277667 A1 | 11/2012 | Yodat et al. |
| 2012/0283186 A1 | 11/2012 | Adams |
| 2012/0302950 A1 | 11/2012 | Landsman et al. |
| 2012/0316460 A1 | 12/2012 | Stout |
| 2013/0261729 A1 | 10/2013 | Gillick et al. |
| 2014/0066891 A1 | 3/2014 | Burns |

FOREIGN PATENT DOCUMENTS

| | | |
|---|---|---|
| WO | 89/03230 A1 | 4/1989 |
| WO | 02/098493 A1 | 12/2002 |
| WO | 2005/068848 A1 | 7/2005 |
| WO | 2009/065153 A2 | 5/2009 |

OTHER PUBLICATIONS

Search Report and Written Opinion dated Dec. 10, 2015 for International Application No. PCT/US2015/049716, filed Sep. 11, 2015, 14 pages.

Davies, Justin E. et al. "Evidence of a Dominant Backward-Propagating 'Suction' Wave Responsible for Diastolic Coronary Filling in Humans, Attenuated in Left Ventricular Hypertrophy," Circulation (2006): 1768-1778 (12 pages).

Office Action dated May 10, 2017 for U.S. Appl. No. 14/851,958.

Office Action dated Nov. 2, 2017 for related U.S. Appl. No. 14/851,958.

* cited by examiner

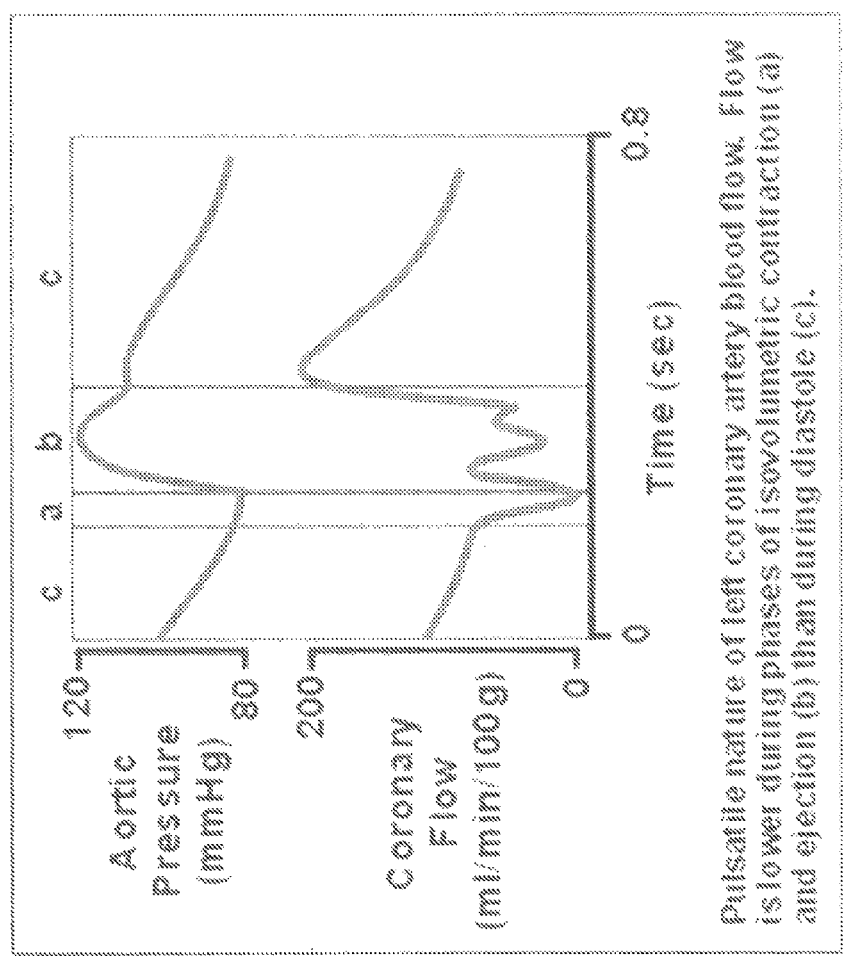

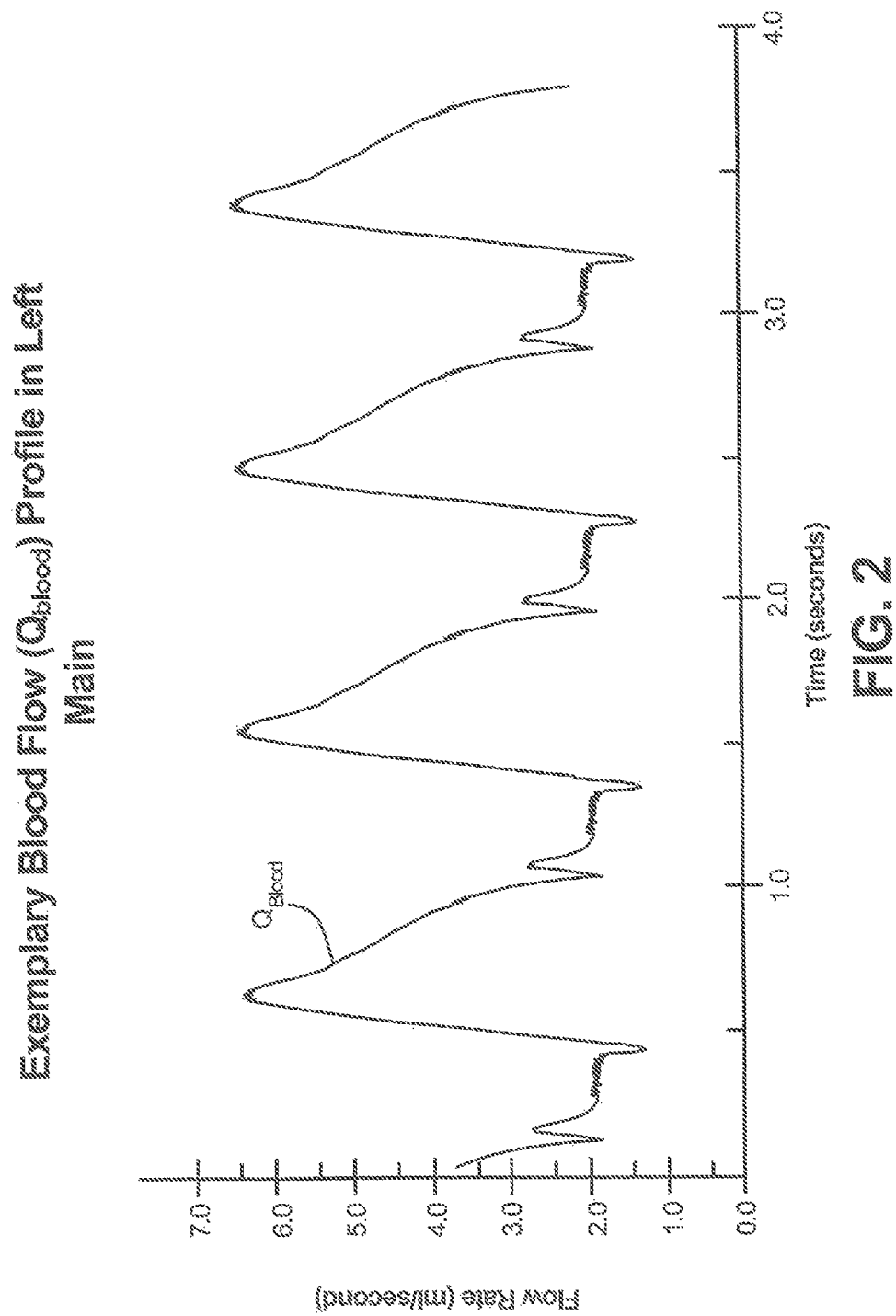

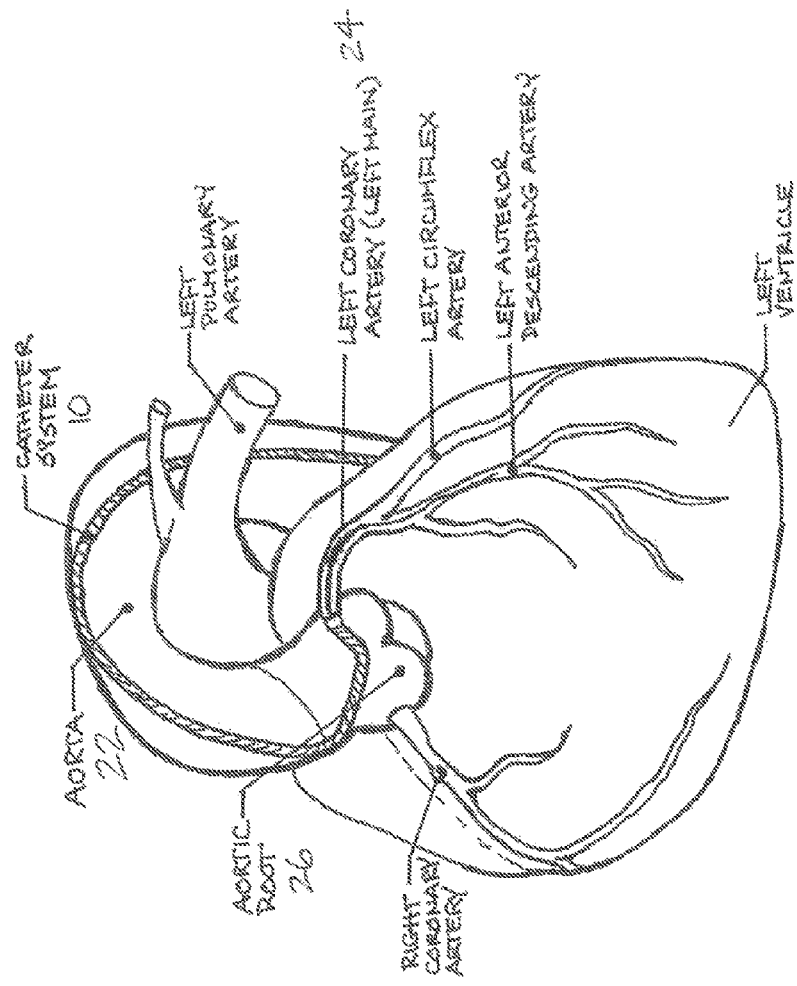

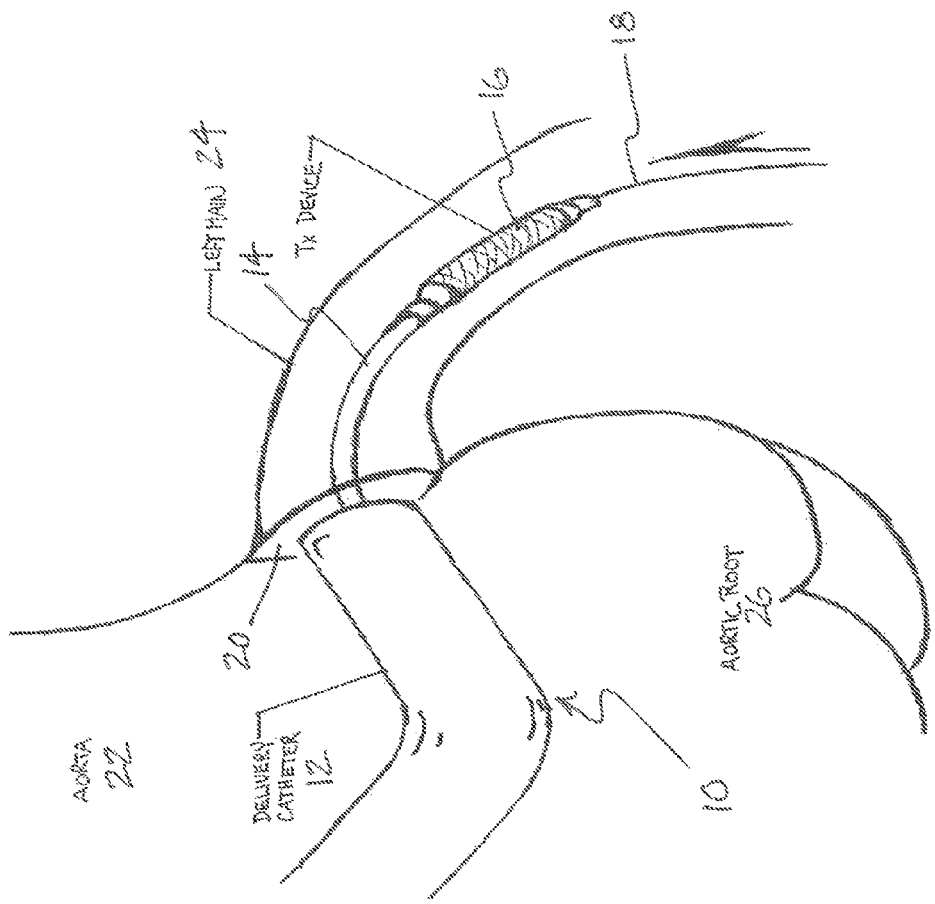

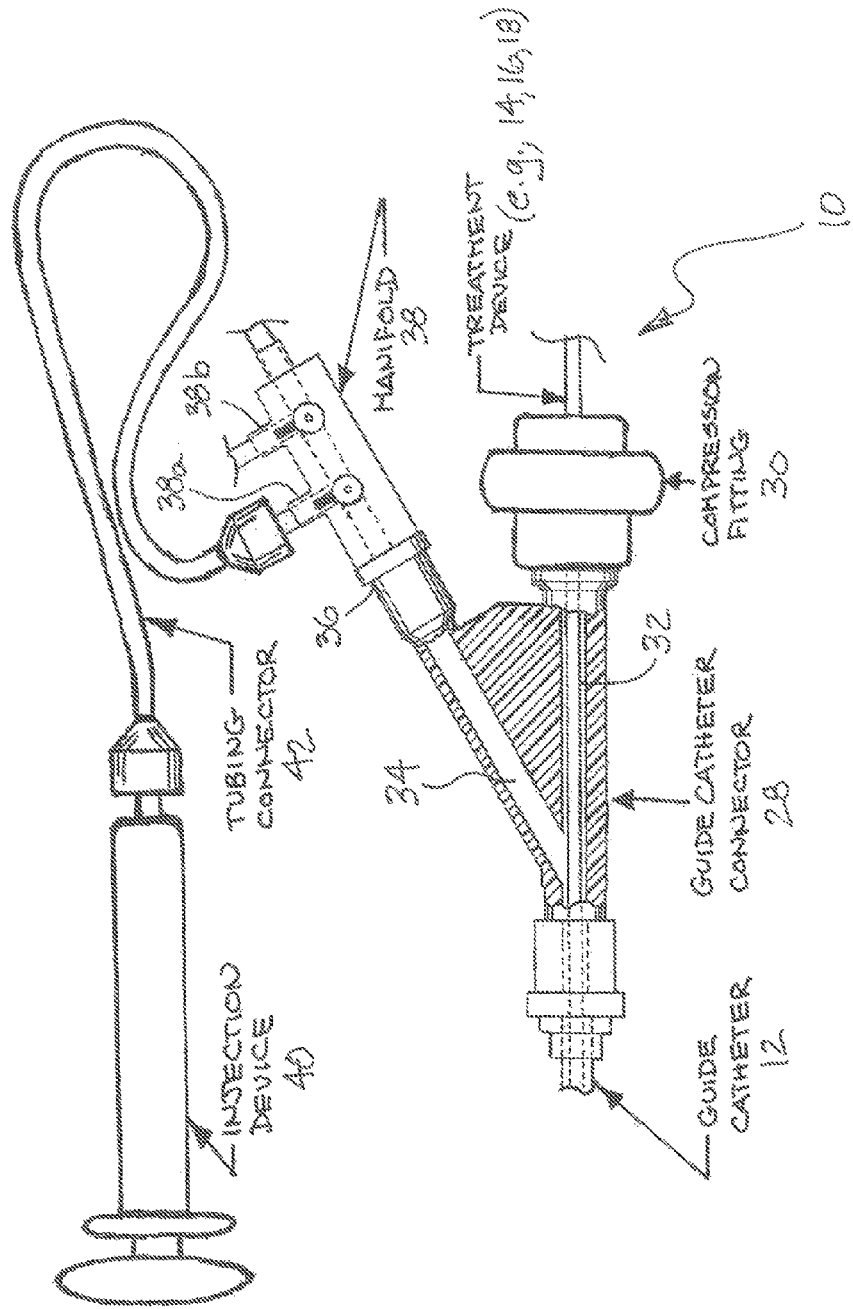

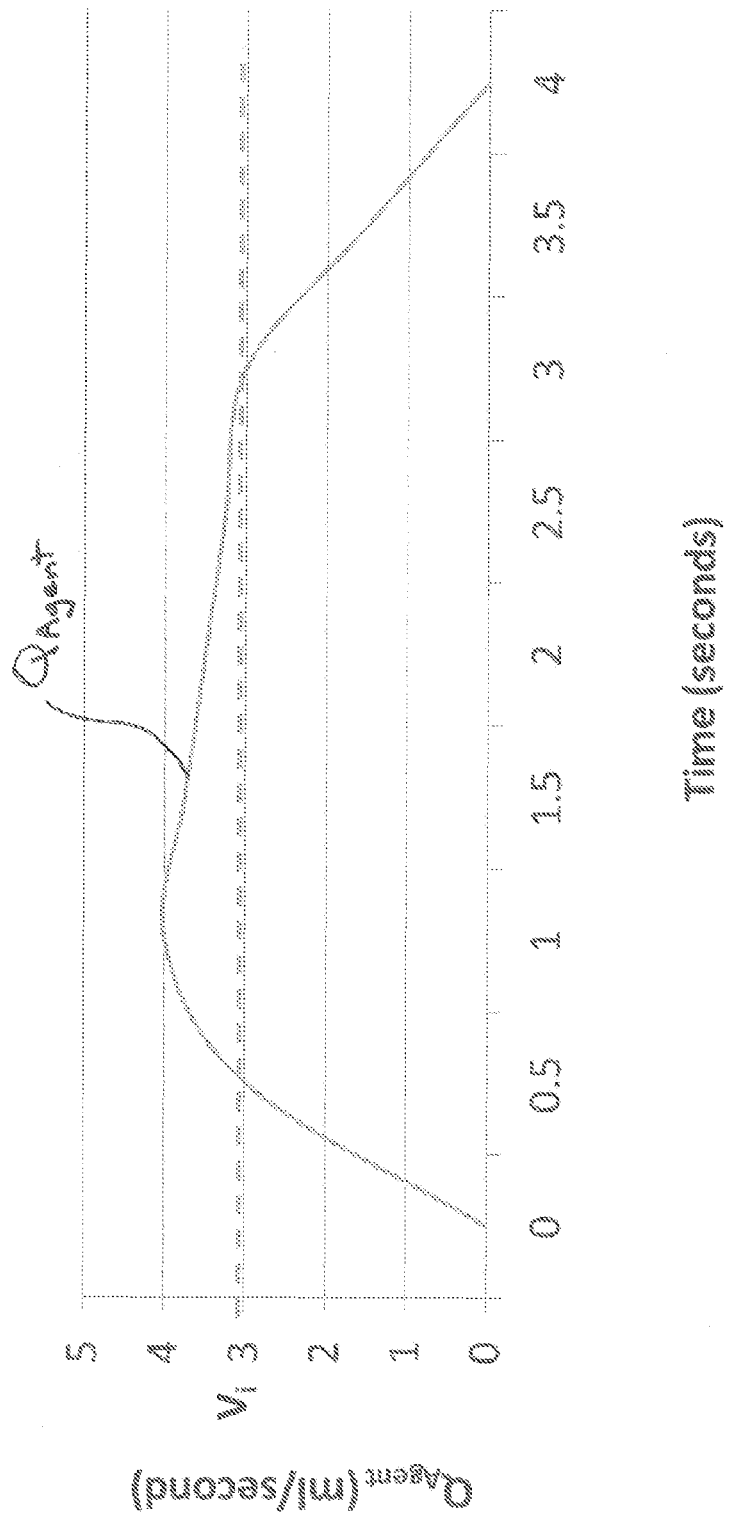

Exemplary Injection Profile of Agent for Tx System of Figures 3

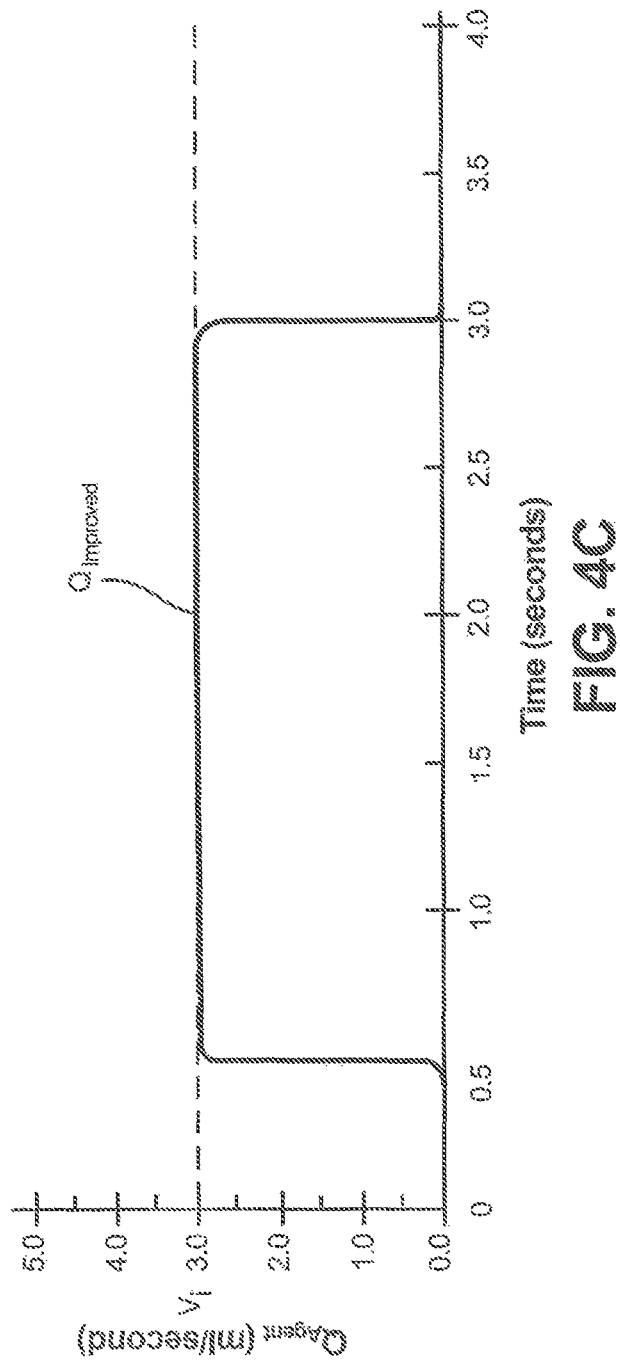

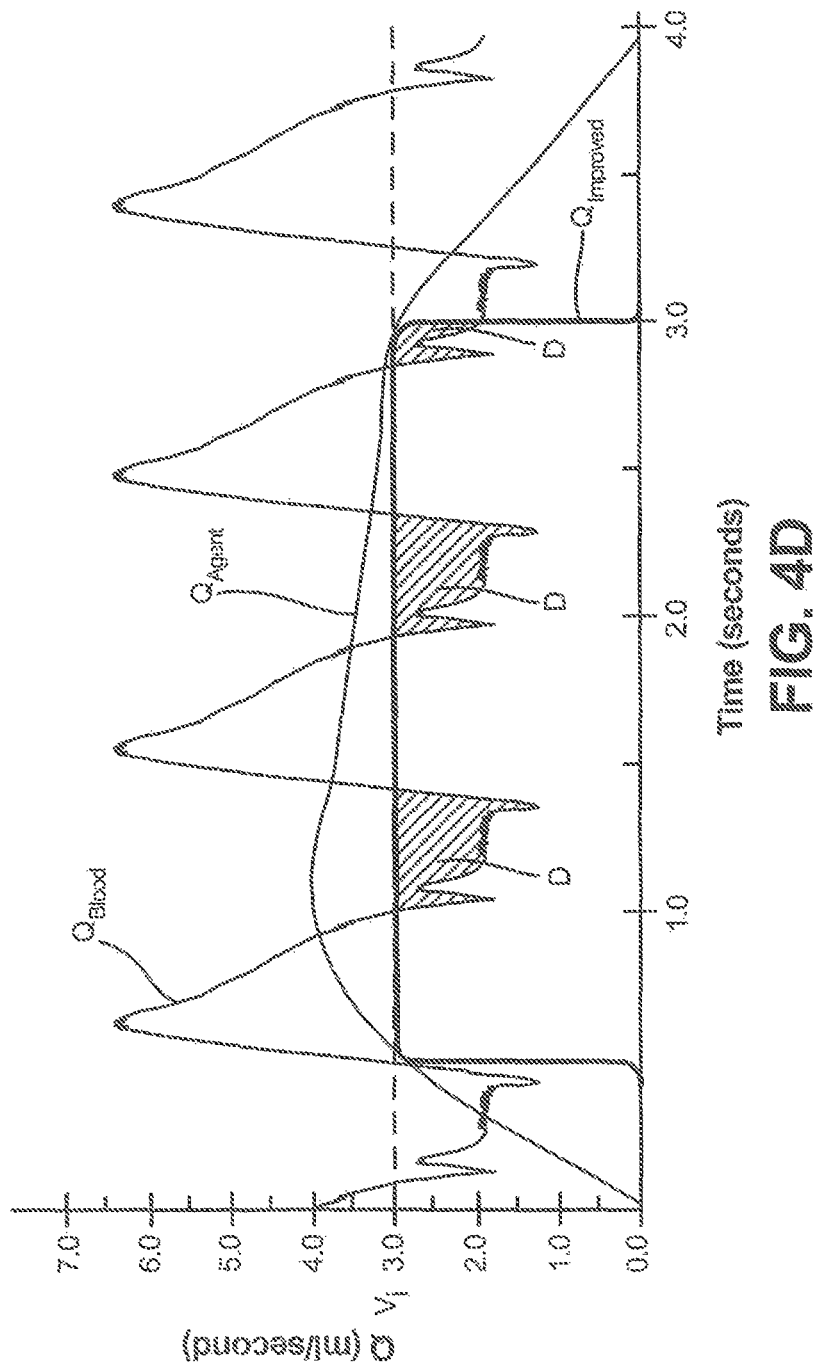

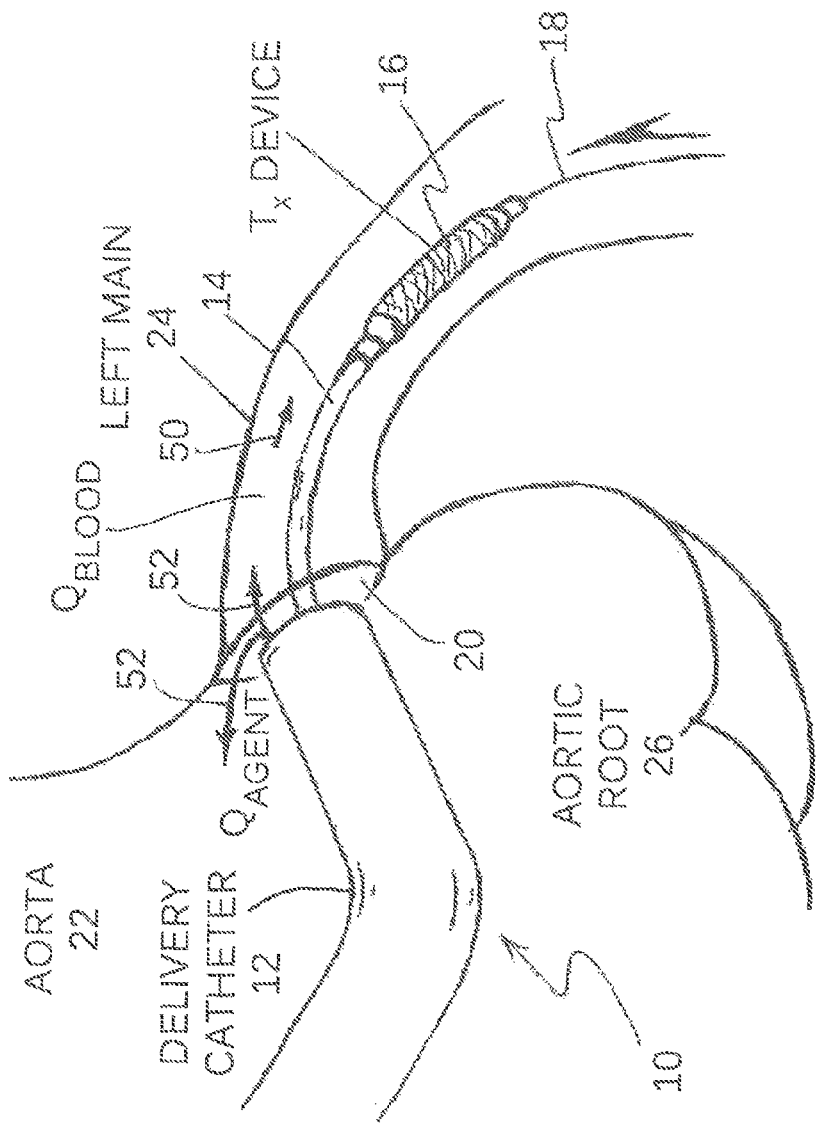

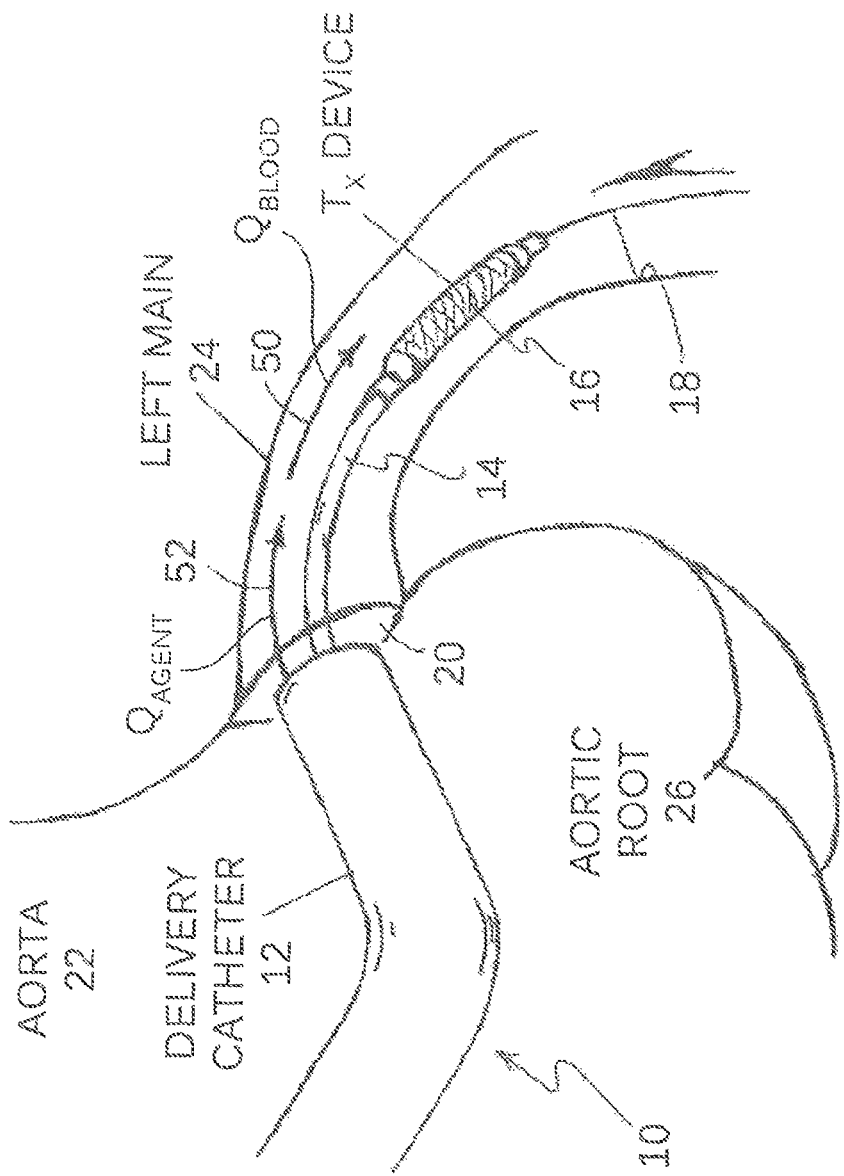

Exemplary Single Chamber Flow Modulator

Exemplary Single Chamber Flow Modulator

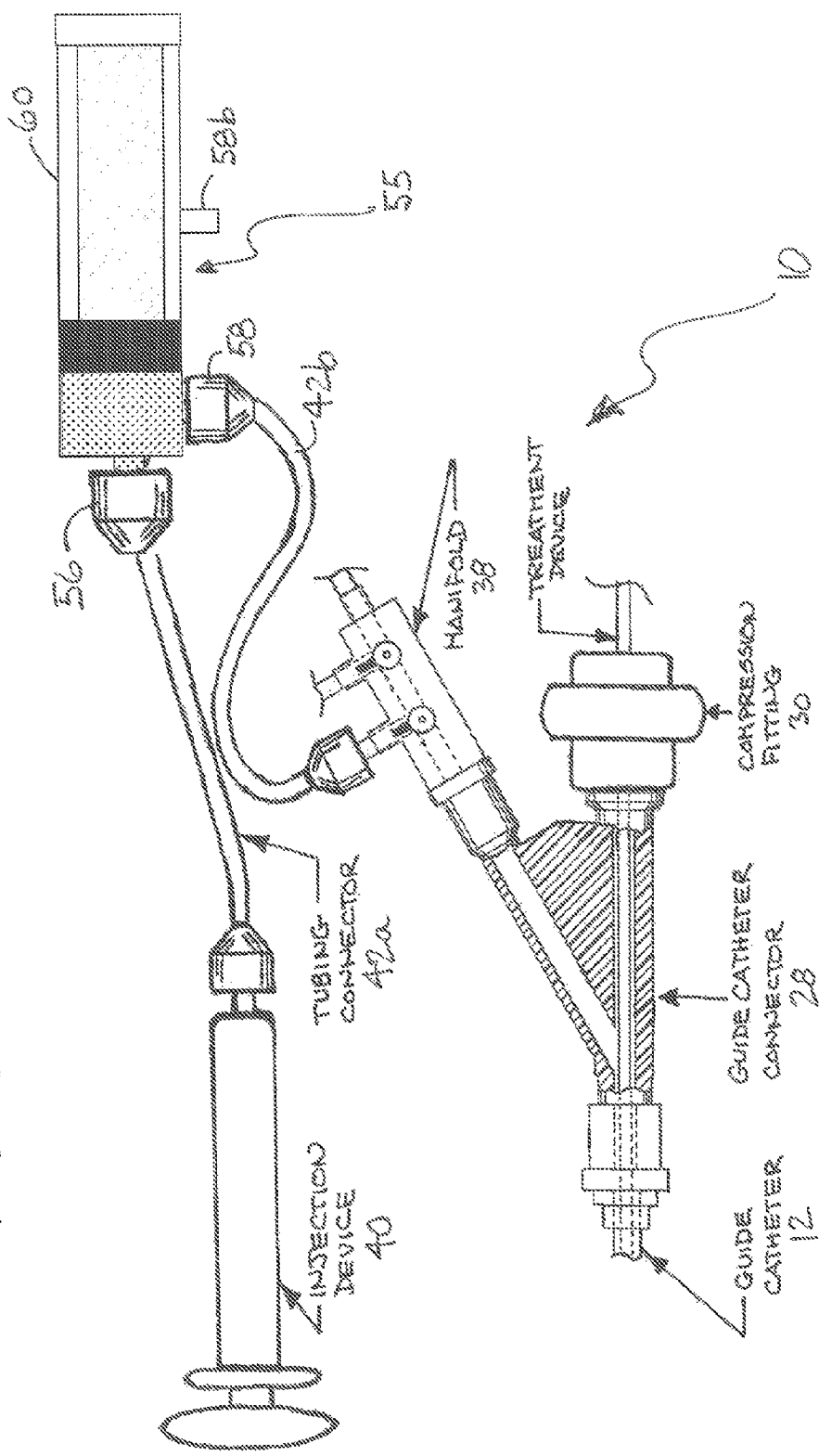

Figure 7

Fluid Flow Equations (Laminar) in a Conduit $$Q \text{ (fluid flow)} = \frac{\Delta P}{\Sigma W_n}$$

Wherein:  $Q$ = flow of fluid through a conduit
$\Delta P$ = pressure differential of the conduit from entrance to outlet
$\Sigma W_n$ = summation of resistances along $n$ sections of a conduit And, for a tubular conduit, each $W_n = \dfrac{8 * \mu * L_n}{\pi * R_n^4 * z_n * c}$ Wherein:  $\pi$ = pi
$\mu$ = viscosity of the fluid
$R_n$ = the inner diameter of the conduit of section $n$
$L_n$ = the length of the conduit of section $n$
$z_n$ = flow correction factor for flow between two tubes of section $n$ (e.g., tubes are coaxial and flow is between), with:
$\quad z = ((1-K_n^4) - (1-K_n^2)^2/\text{Natural Log }(1/K_n))$
$\quad K_n = r_n/R_n$
$\quad r_n$ = outer diameter of inner tube of section $n$
$\quad R_n$ = inner diameter of outer tube of section $n$
$c$ = empirically derived coefficient to correct for non-laminar flow (i.e., flow head development, transitions between sections $n$, pressure changes, etc.), dimensional variations (i.e., non-concentric, deformation), temperature variations (i.e., fluid viscosity), etc.

Exemplary Two-Chamber Flow Modulator

Exemplary Two-Chamber Flow Modulator

Exemplary Two-Chamber Flow Modulator

Exemplary Two-Chamber Flow Modulator with Holding Chamber

Exemplary Two-Chamber Flow Modulator with Holding Chamber

Exemplary Two-Chamber Flow Modulator with Holding Chamber

Capacitance Chamber Flow Modulator (Bladder)

Capacitance Chamber Flow Modulator (Bladder)

Exemplary Flow Modulator with Constant Force Chamber

Exemplary Flow Modulator with Constant Force Chamber

Exemplary Constant Flow Modulator

Exemplary Constant Flow Modulator

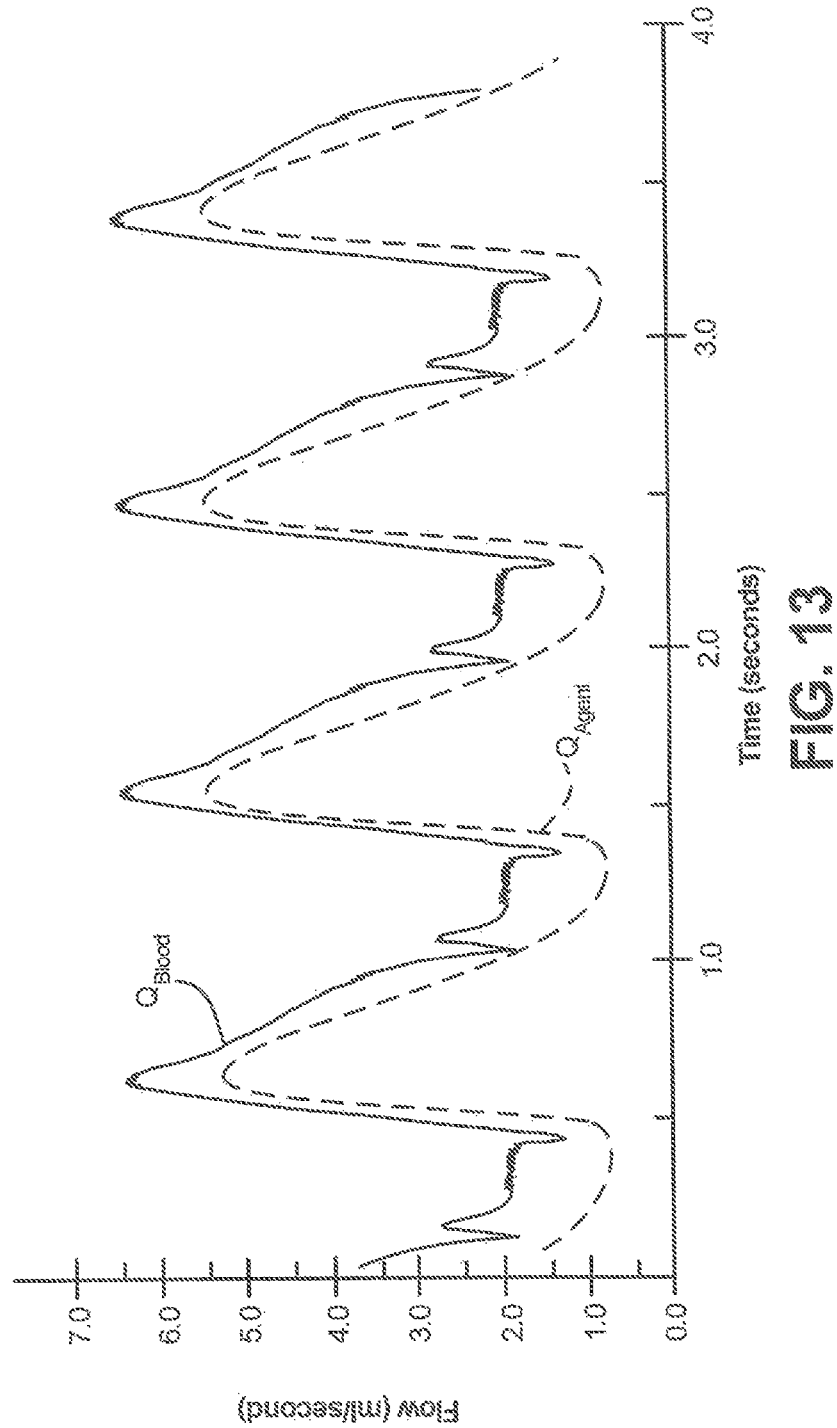

Exemplary Schemas of Synchronized Agent Delivery Modulation System

Exemplary Synchronized Agent Delivery with Direct Modulation

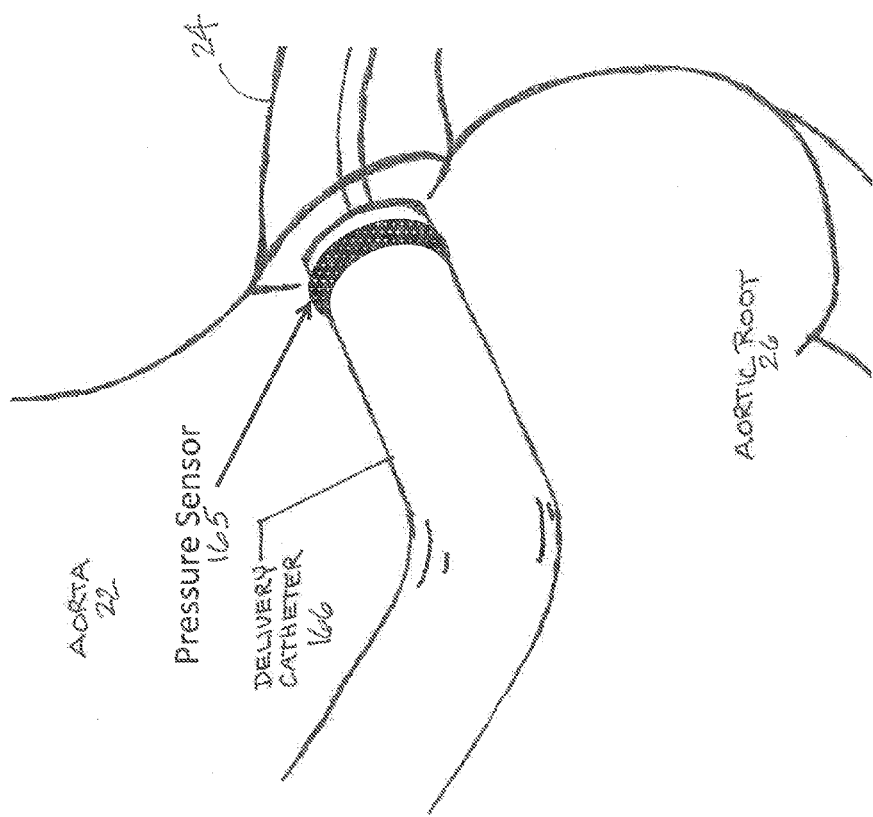

Exemplary Synchronized Agent Delivery with Indirect Modulation
(Top View)

Exemplary Synchronized Agent Delivery with Indirect Modulation
(Side View)

Detail of Brake Mechanism
(Side View)

Figure 17
Exemplary Delivery Catheter Distal Constructions
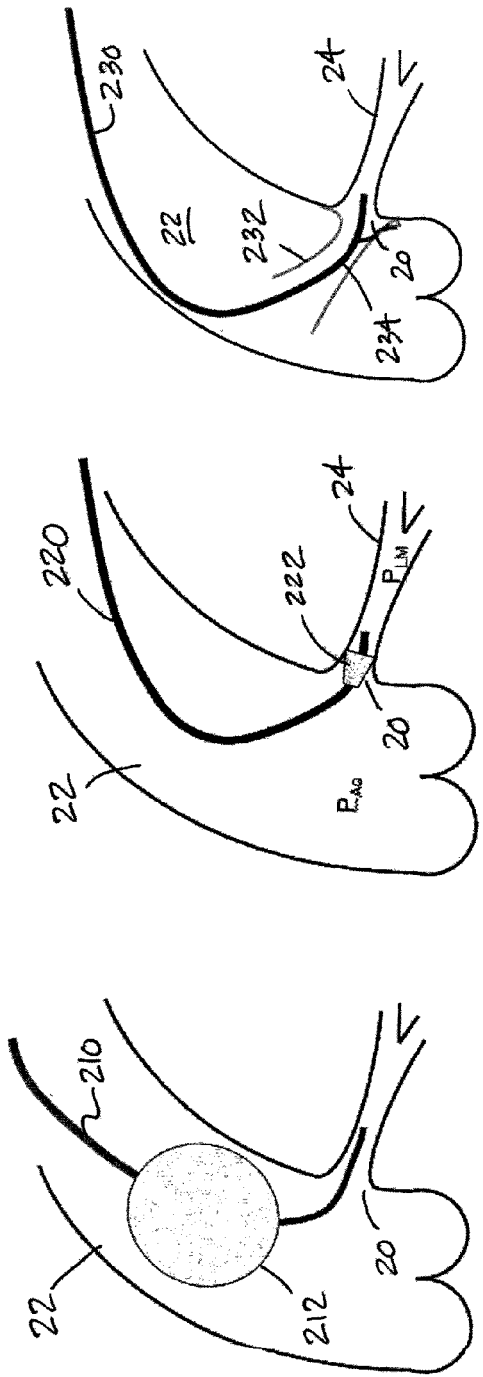
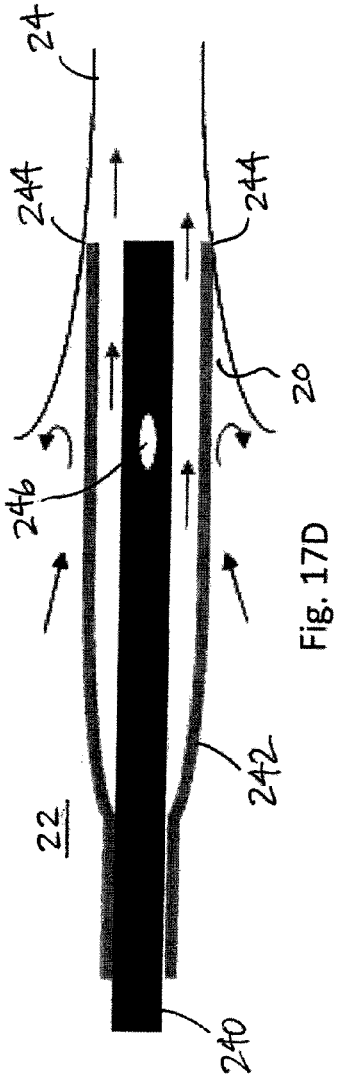
Fig. 17A
Fig. 17B
Fig. 17C
Fig. 17D Exemplary Delivery Catheter with Distal Disrupting Structure

FIG. 19

Illustrative Media Delivery Modulation Elements / Functions with Exemplary References

| Elements/Functions | Illustrative Description | | |
|---|---|---|---|
| Injection Device Type | Automated/Power Injector<br><br>FIG. 3C | Manual<br><br>FIG. 3C | Gravity Fed<br><br>In Description |
| Regulation Type | Constant Flow<br><br>FIG. 12A - 12B | Pressure<br><br>FIG. 6A - 6B | Flow Resistance Alteration<br><br>FIG. 17B |
| Sequential Delivery or Direct Delivery | Sequential (Delayed)<br><br>FIG. 10A - 10B | Direct (Non-sequential) Delivery<br><br>FIG. 6A - 6B | |
| Synchronization with Corporeal Flow | Synchronized<br><br>FIG. 13 | Non-synchronized<br><br>FIG. 4C | |
| Flow Activation/Deactivation | Direct to Pump<br><br>FIG. 14 | Indirect: Post-pump<br><br>FIG. 14 | |
| Flow Distal Environ Alternation | Capture/Isolate/Modify<br><br>FIG. 17A - 17B | Disruption<br><br>FIG. 18 | |

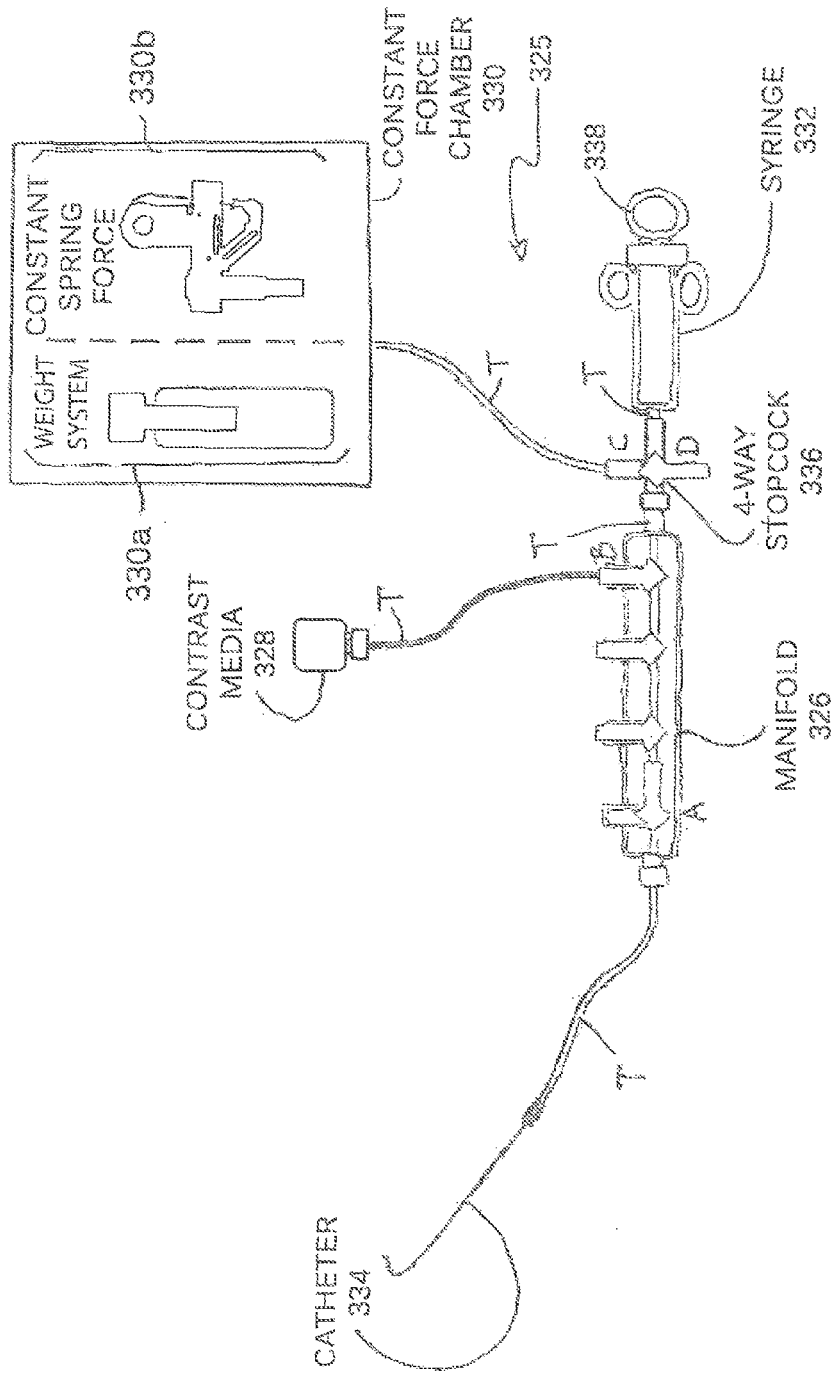

Exemplary Constant Force Modulator – Filling Injector

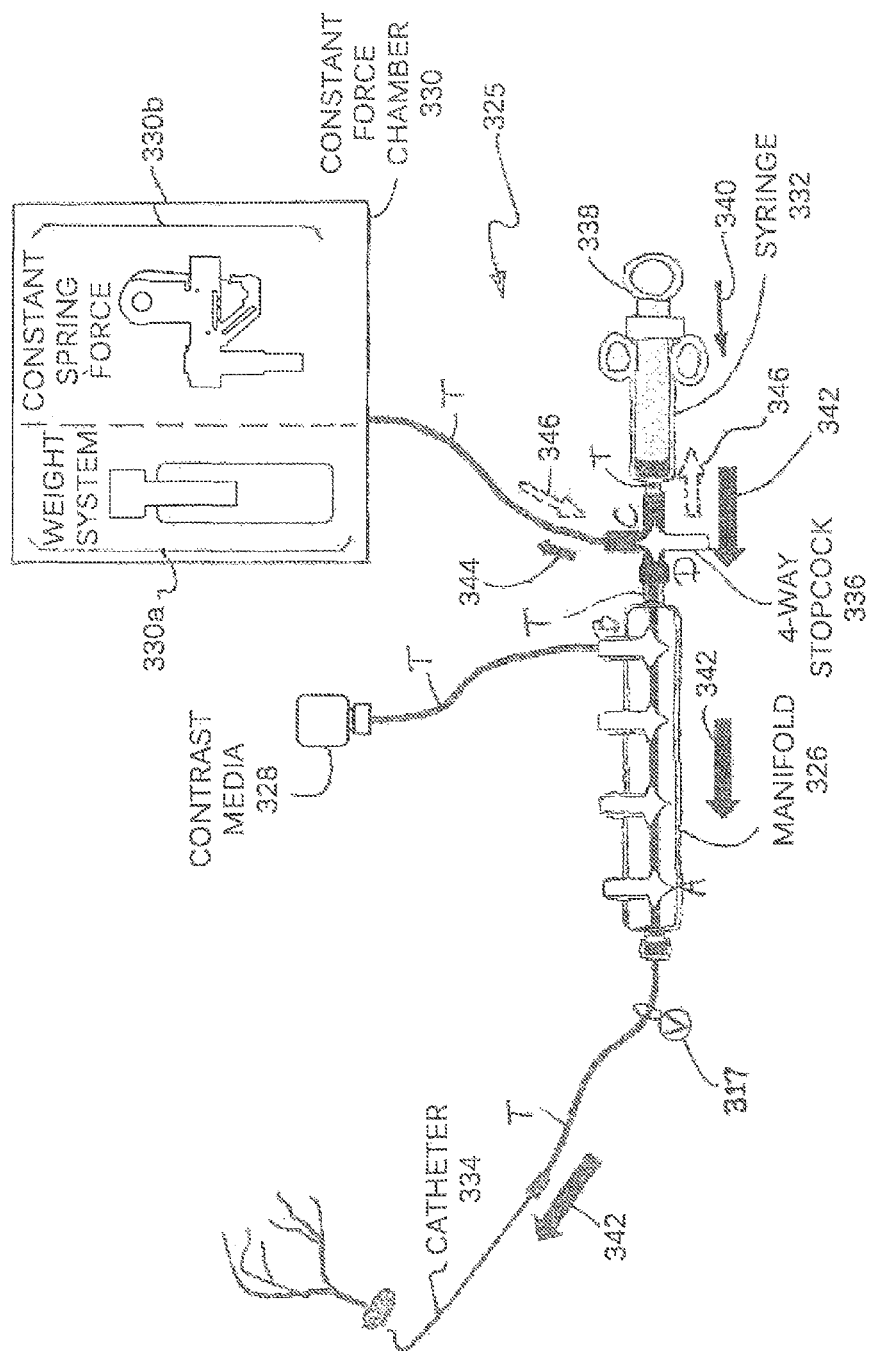

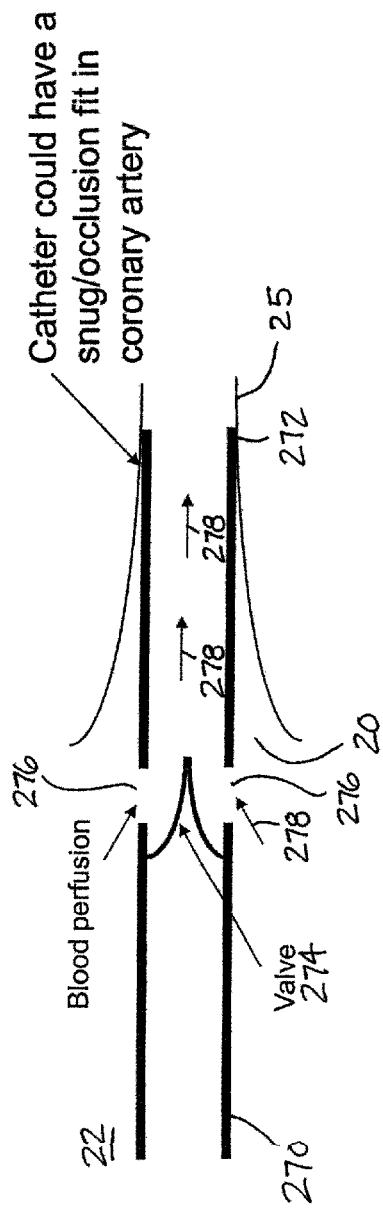
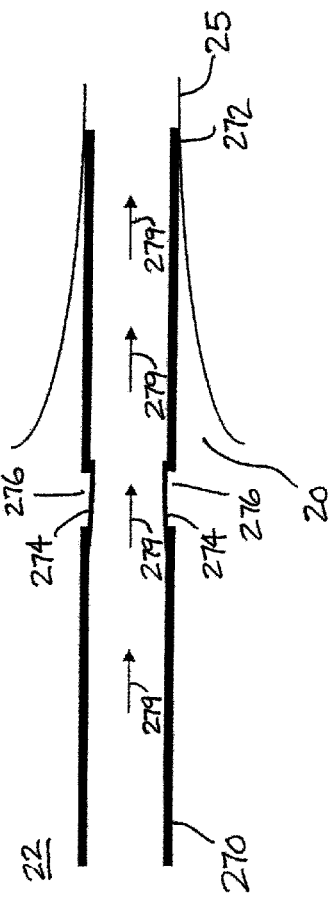
FIG. 25A
Example: Distal Valve with Perfusion Orifice(s) – No Injection, Valve Closed
FIG. 25B
Example: Distal Valve with Injection – Orifice(s) Occluded, Valve Open

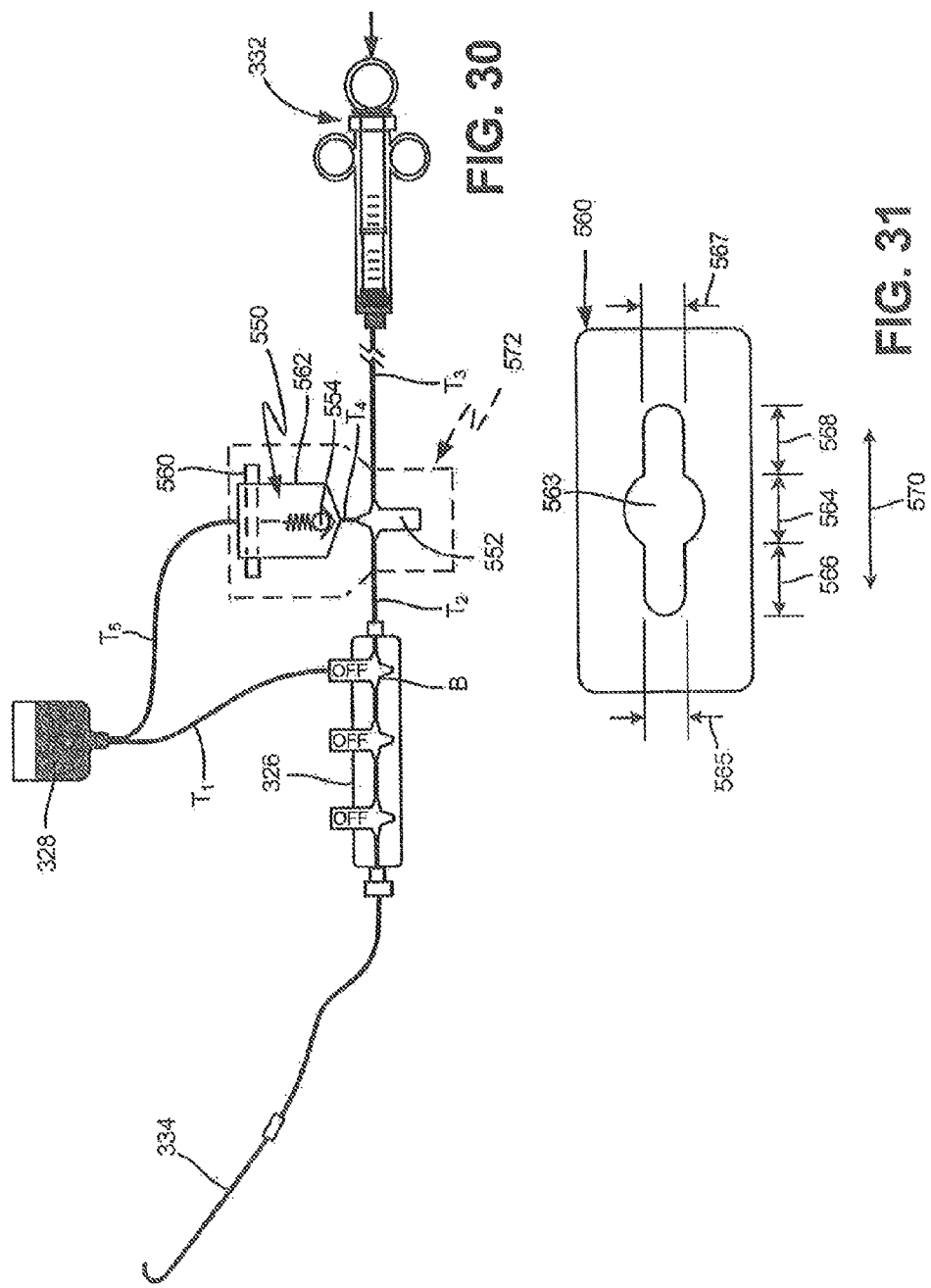

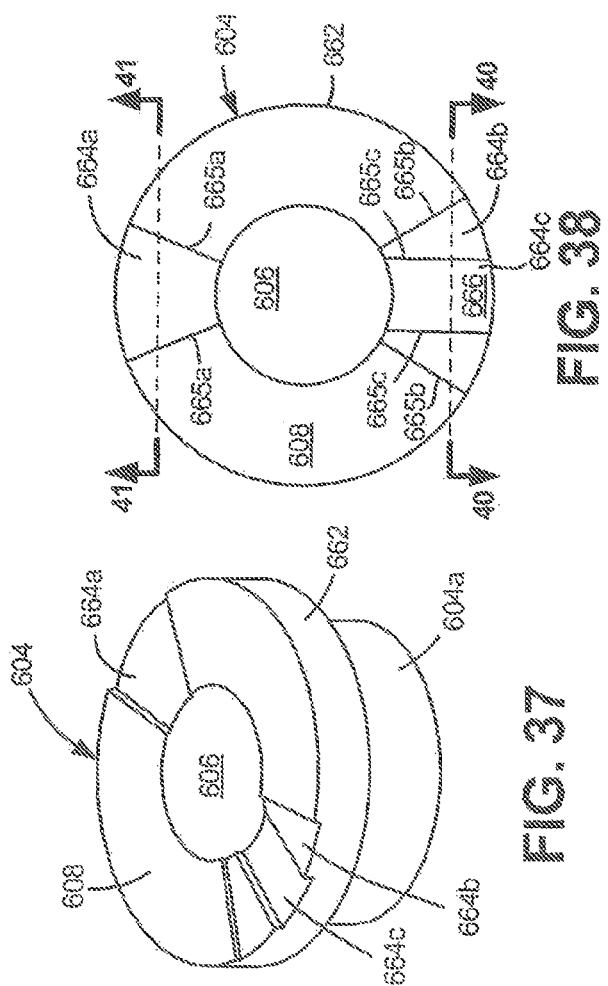
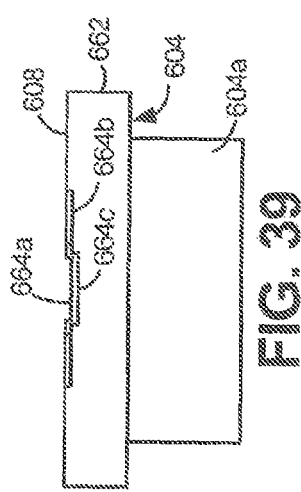
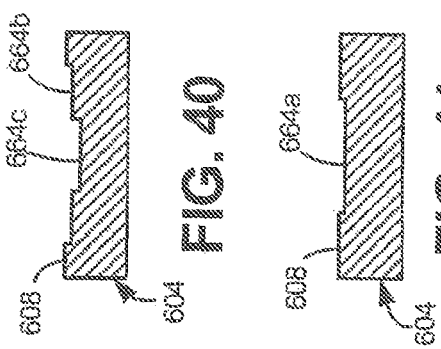
FIG. 37
FIG. 38
FIG. 39
FIG. 40
FIG. 41

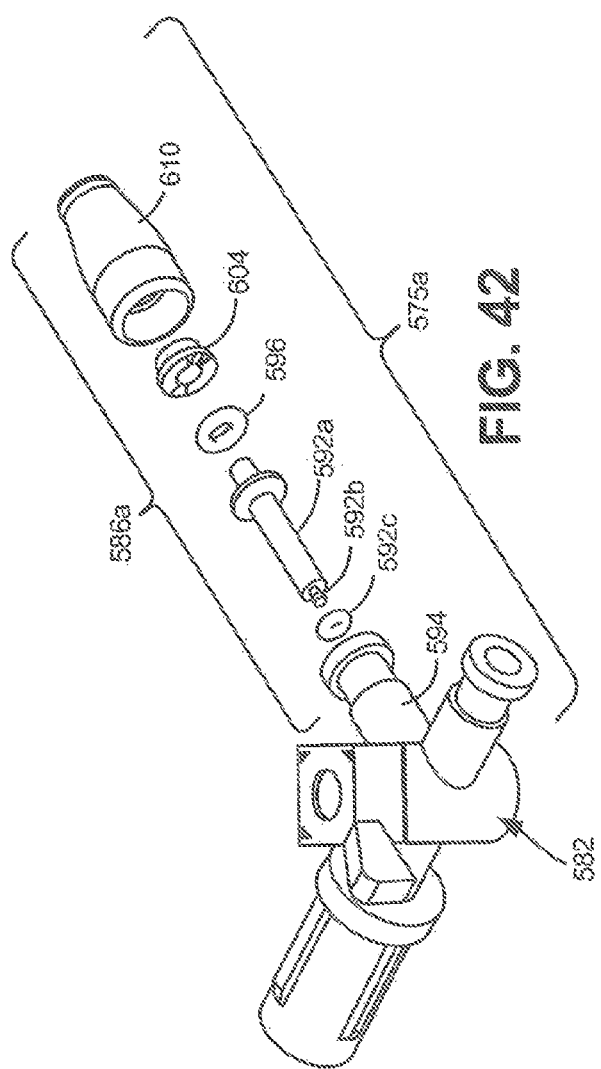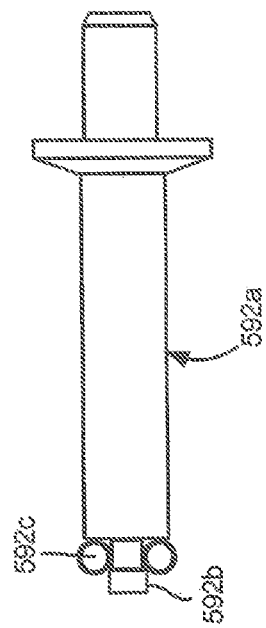

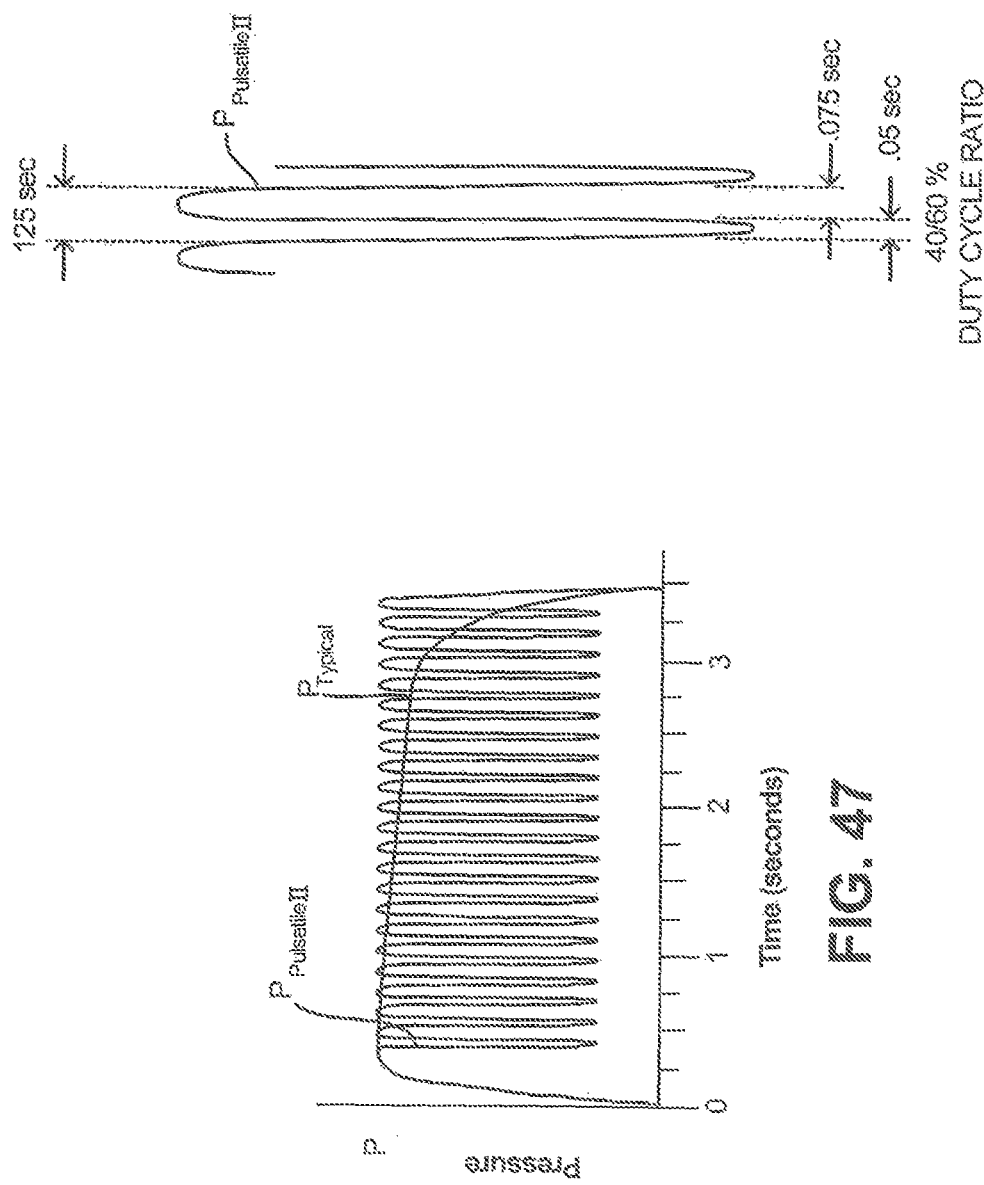

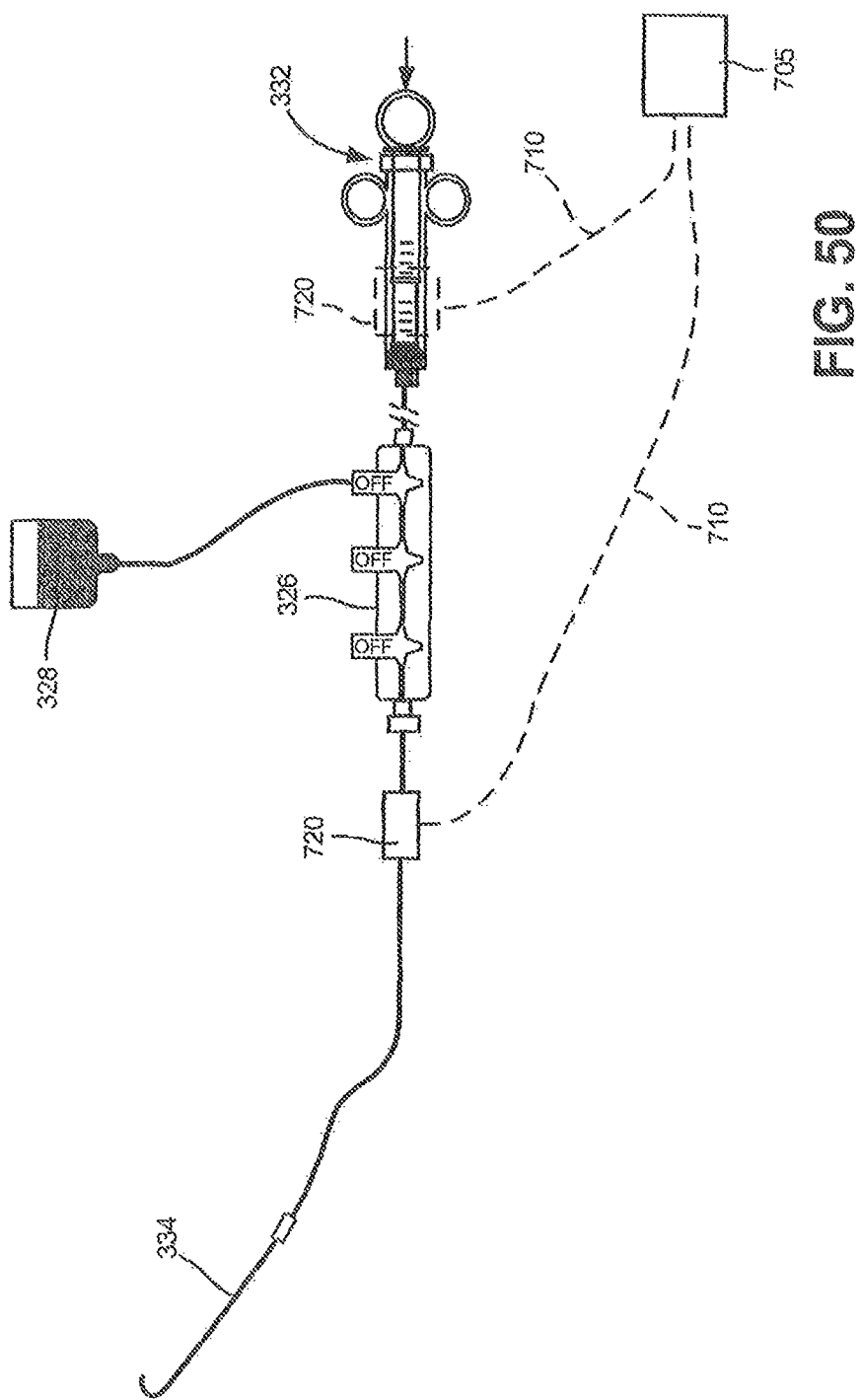

Flow diagram of Figs. 6

Simple Parallel Resistance
with Diversion

Flow diagram with Check Valve with Diversion

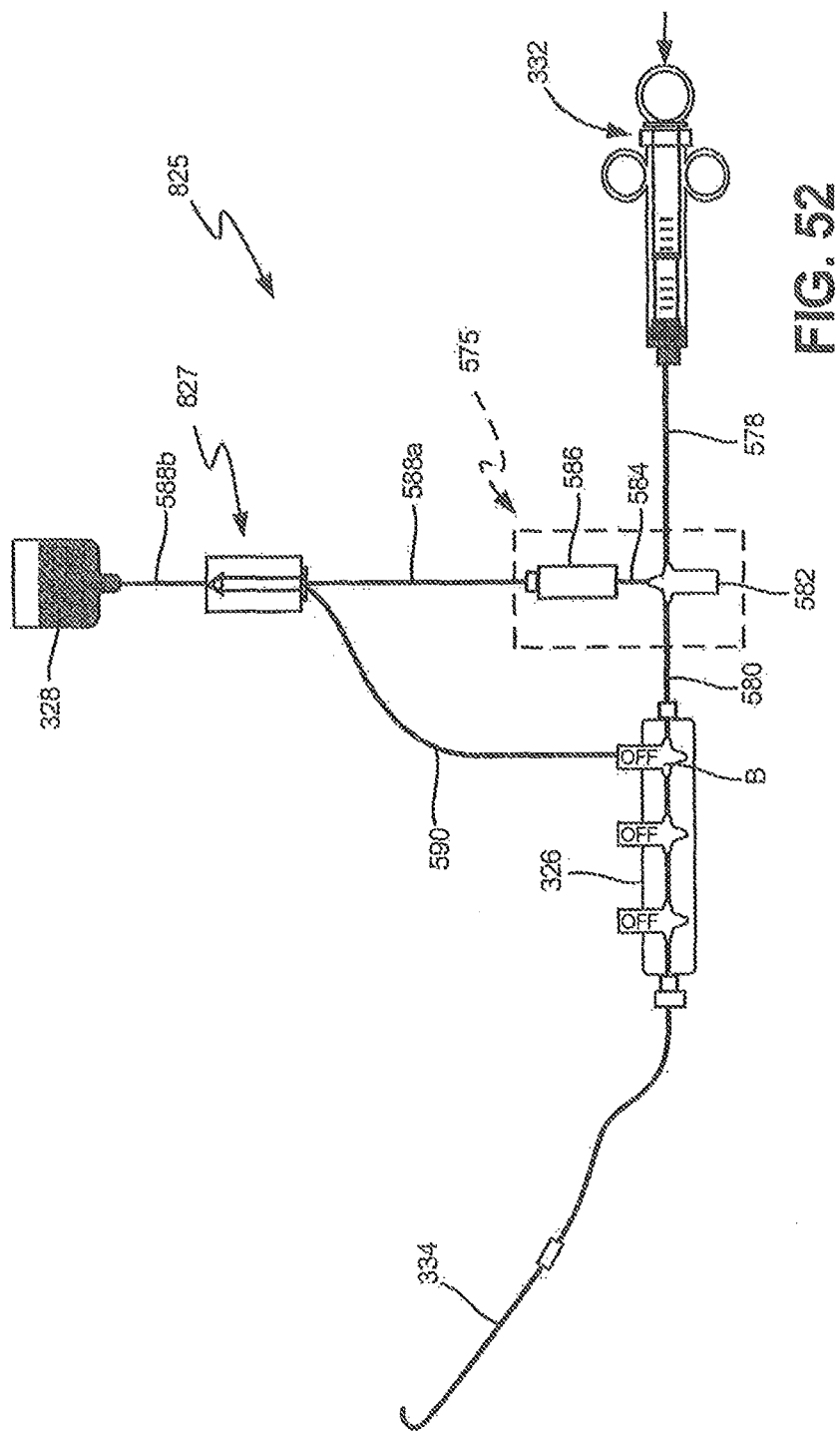

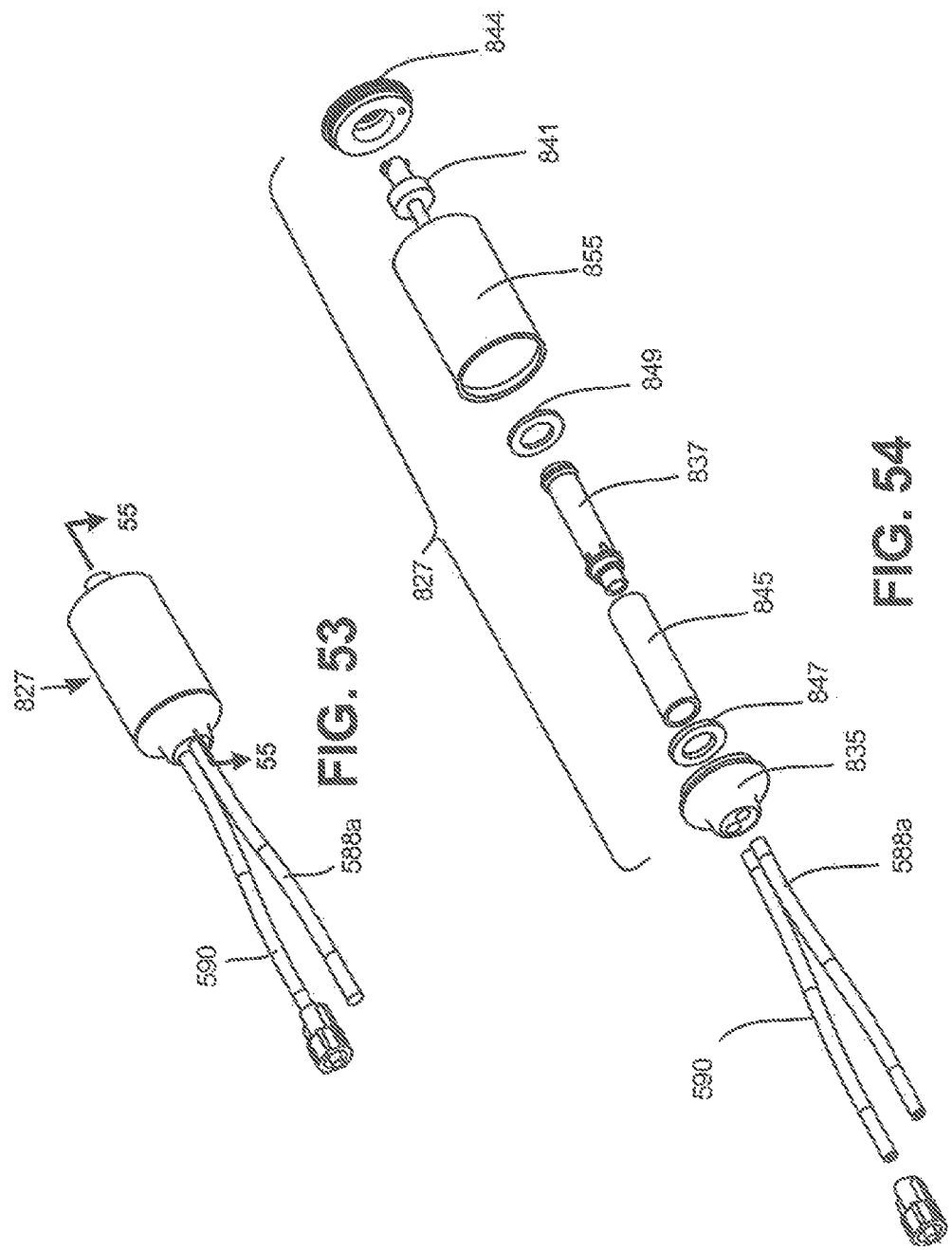

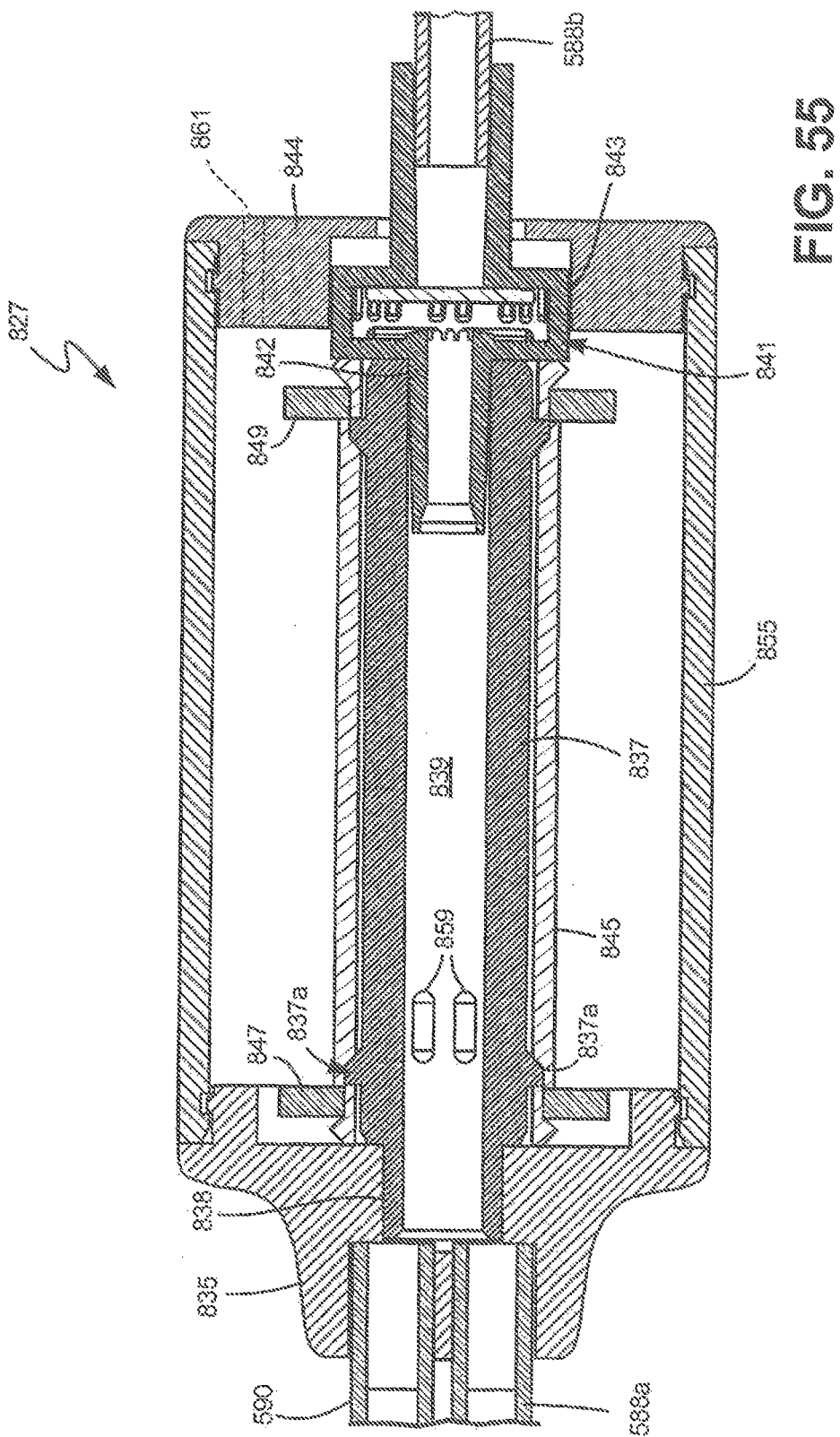

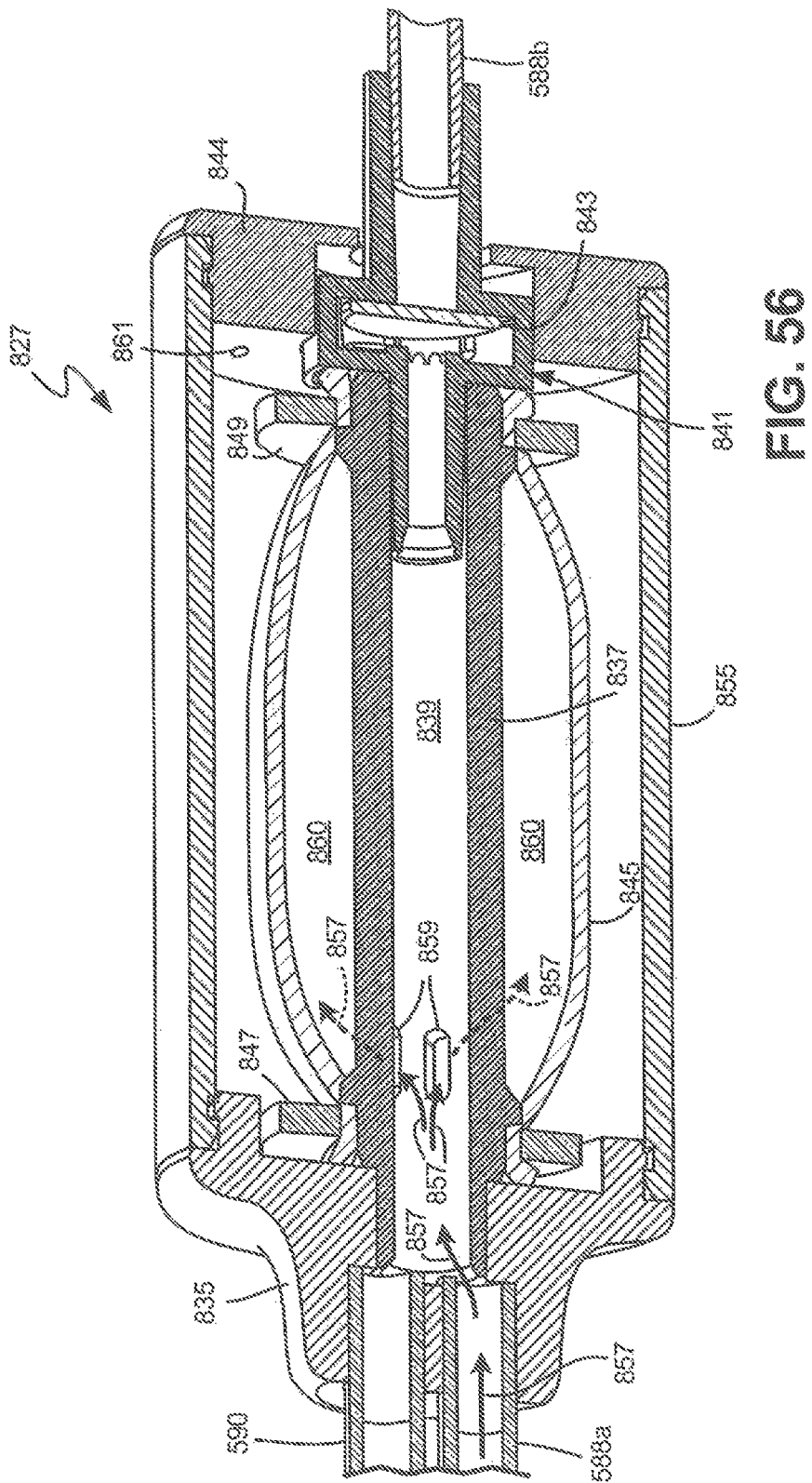

ADJUSTABLE MEDIUM DIVERTER

CROSS-REFERENCE TO RELATED APPLICATION(S)

This application is a continuation in part of U.S. patent application Ser. No. 13/839,771, filed on Mar. 15, 2013, for "Devices and Methods for Modulating Medium Delivery", which claims the benefit of priority from U.S. Provisional Patent Application No. 61/694,137, filed Aug. 28, 2012 for "Devices and Methods for Modulating Medium Delivery" and this application claims the benefit of priority from U.S. Provisional Patent Application No. 62/048,974, filed Sep. 11, 2014, for "Devices and Methods for Modulating Medium Delivery," and U.S. Provisional Patent Application No. 62/082,260, filed Nov. 20, 2014, for "Devices and Methods for Modulating Medium Delivery", the contents of all of these priority applications are hereby incorporated by reference in their entirety.

BACKGROUND

There are numerous occasions in the diagnostic, prophylactic and treatment practice of medicine wherein an agent, medicant, or medium is preferably delivered to a specific site within the body, as opposed to a more general, systemic introduction. One such exemplary occasion is the delivery of contrast media to coronary vasculature in the diagnosis (i.e., angiography) and treatment (i.e., balloon angioplasty and stenting) of coronary vascular disease.

SUMMARY

In one aspect, a system for modulating delivery of a fluid medium to a selected site within a patient's body is disclosed. The system comprises a syringe for injecting the fluid medium, a delivery catheter comprising a conduit for delivering the fluid medium from outside of the body to the selected site within the body, and a flow diverter assembly disposed in a fluid medium flow path between the syringe and the delivery catheter. The syringe comprises a chamber for receiving the fluid medium therein. The flow diverter assembly is configured to simultaneously divert at least some of the fluid medium within the chamber of the syringe away from the delivery of the medium through the delivery catheter conduit during injecting with the syringe, and wherein the flow diverter assembly creates increasing medium fluid flow resistance with increasing pressure level of the fluid medium within the flow diverter assembly.

In another aspect, a method for modulating fluid delivery of a fluid medium to a selected site within a patient's body is disclosed. The method comprises injecting the fluid medium from a syringe through a fluid delivery catheter to deliver the fluid medium to the selected site, and simultaneously employing a flow diverter assembly disposed in a fluid medium flow path between the syringe and the delivery catheter. The flow diverter assembly resides outside the patient's body and is configured to divert at least some of the fluid medium within the syringe away from the delivery of medium to the delivery catheter conduit during injection of medium, and wherein the diverter assembly is configured to increase medium fluid flow resistance with an increase in pressure level of the fluid medium within the flow diverter assembly.

This summary is provided to introduce concepts in simplified form that are further described below in the Detailed Description. This summary is not intended to identify key features or essential features of the disclosed or claimed subject matter and is not intended to describe each disclosed embodiment or every implementation of the disclosed or claimed subject matter. Specifically, features disclosed herein with respect to one embodiment may be equally applicable to another. Further, this summary is not intended to be used as an aid in determining the scope of the claimed subject matter. Many other novel advantages, features, and relationships will become apparent as this description proceeds. The figures and the description that follow more particularly exemplify illustrative embodiments.

BRIEF DESCRIPTION OF THE DRAWINGS

The disclosed subject matter will be further explained with reference to the attached figures, wherein like structure or system elements are referred to by like reference numerals throughout the several views.

FIG. 1 illustrates in graphic form, the exemplary pulsatile nature of left coronary artery blood flow and blood pressure.

FIG. 2 is a graphic representation of an exemplary blood flow rate profile for a left main coronary artery.

FIG. 3A illustrates an exemplary coronary artery treatment system.

FIG. 3B illustrates a distal portion of the exemplary treatment of FIG. 3A.

FIG. 3C illustrates a proximal portion of the exemplary treatment system of FIG. 3A.

FIG. 4A illustrates graphically an exemplary injection profile (flow rate) of agent for the treatment system of FIG. 3.

FIG. 4C illustrates graphically an exemplary improved constant injection profile (flow rate) of agent for achieving opacification.

FIG. 4D illustrates graphically the exemplary agent injection profile of FIG. 4A relative to the exemplary blood rate flow profile of FIG. 2.

FIG. 5A illustrates an exemplary flow of injection in the distal portion of the exemplary treatment system of FIG. 3B.

FIG. 5B illustrates an alternative exemplary flow of injection in the distal portion of the exemplary treatment system of FIG. 3B.

FIG. 6C illustrates the single chamber flow modulator of FIGS. 6A and 6B disposed in the proximal portion of the treatment system of FIG. 3.

FIG. 7 sets forth exemplary fluid flow equations (laminar) that may be used in modeling a conduit fluid flow.

FIG. 13 illustrates graphically an exemplary agent injection profile (flow rate) synchronized with the exemplary blood flow rate profile of FIG. 2.

FIG. 16A illustrates an exemplary synchronized agent delivery with indirect modulation, adjacent a distal portion of a treatment system therefor.

FIGS. 17A, 17B, 17C and 17D illustrate exemplary delivery catheter distal constructions.

FIG. 19 illustrates, in chart form, exemplary medium delivery modulation control factors and/or elements, the features of which may be combined, in part or in whole, to achieve the advantages of minimizing over-introduction of agent into a patient, pursuant to the teachings disclosed herein.

FIGS. 20-22 illustrate an exemplary constant force modulator system, in different stages of flow control.

FIGS. 25A and 25B illustrate another exemplary arrangement for passive valve control of blood flow and medium flow adjacent a medium delivery site.

FIG. 30 illustrates an exemplary flow diverter assembly.

FIG. 31 illustrates a switch plate for the flow divert assembly of FIG. 30.

FIG. 37 is a perspective view of an exemplary compression plate for the valve of the automatic flow diverter assembly shown in FIGS. 33-36.

FIG. 38 is a plan view of a proximal face of the compression plate of FIG. 37.

FIG. 39 is a side view of the compression plate.

FIG. 40 is a sectional view, as taken along lines 40-40 in FIG. 38.

FIG. 41 is a sectional view, as taken along lines 41-41 in FIG. 38.

FIG. 42 is an exploded perspective view of an alternative automatic flow diverter assembly.

FIG. 43 is a side view of a movable diffuser and check valve O-ring thereon for the automatic flow diverter assembly of FIG. 42.

FIG. 47 illustrates graphically an injection profile (pressure) of agent for the treatment system of FIG. 3 in a typical injection ($P_{Typical}$) and an alternative pulsed medium injection profile ($P_{Pulsatile\ II}$).

FIG. 48 illustrates an enlarged view a segment of the pulsed injection profile $P_{Pulsatile\ II}$ of FIG. 47.

FIG. 50 illustrates an exemplary arrangement for direct application of pulsed pressure to the medium being manually injected via a catheter.

FIG. 52 illustrates an exemplary medium management system.

FIG. 53 is a perspective view of an exemplary medium diversion reservoir.

FIG. 54 is a perspective exploded view of an exemplary medium diversion reservoir.

FIG. 55 is a cross-sectional view of the exemplary medium diversion reservoir in a first configuration, taken along line 55-55 of FIG. 53.

FIG. 56 is a cross-sectional view of the exemplary medium diversion reservoir in a second configuration, taken along line 55-55 of FIG. 53.

Figure 4B:
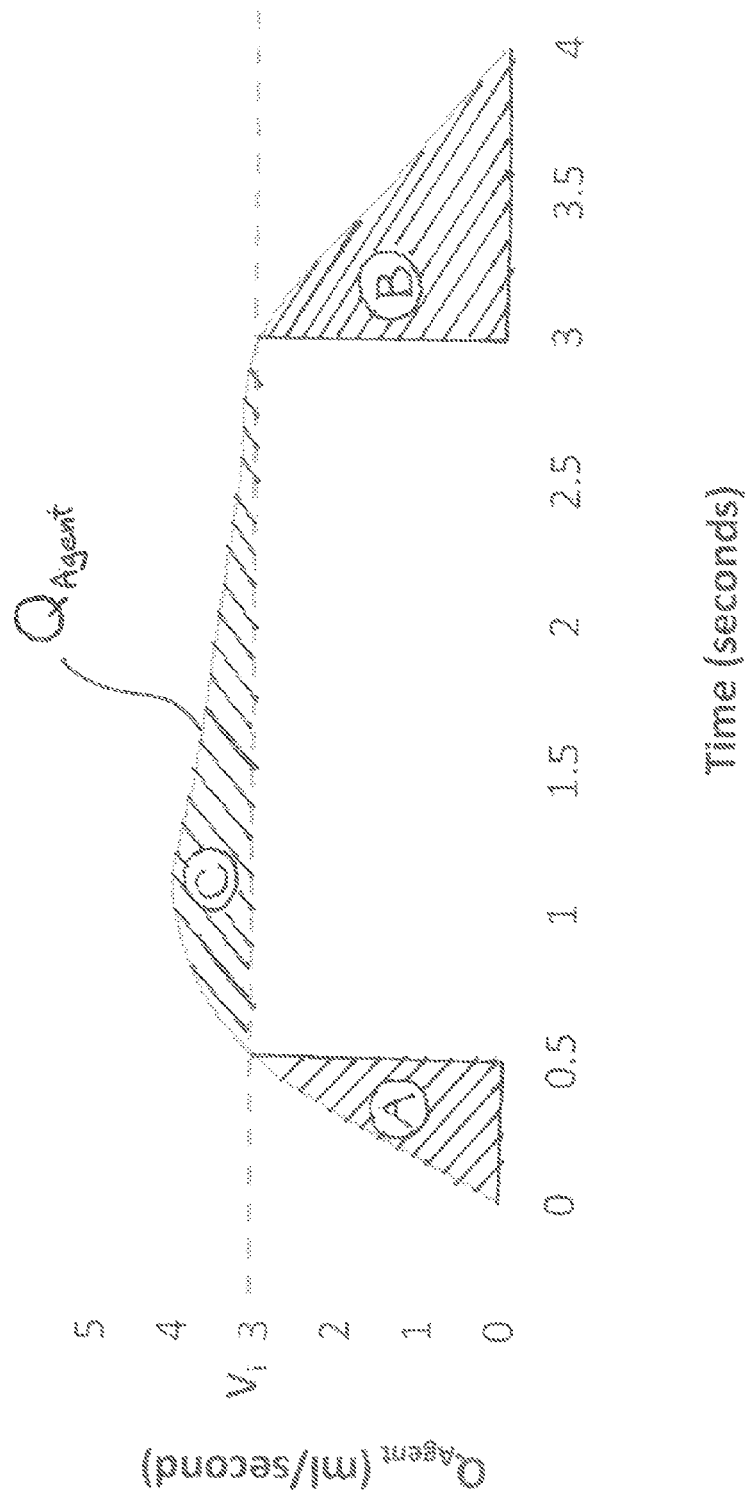
FIG. 4B illustrates graphically an injection profile (flow rate) of agent for the treatment system of FIG. 3, identifying under-injection and over-injection volume areas of media for opacification purposes.

While the above-identified figures set forth one or more embodiments of the disclosed subject matter, other embodiments are also contemplated, as noted in the disclosure. In all cases, this disclosure presents the disclosed subject matter by way of representation and not limitation. It should be understood that numerous other modifications and embodiments can be devised by those skilled in the art which fall within the scope and spirit of the principles of this disclosure.

The figures may not be drawn to scale. In particular, some features may be enlarged relative to other features for clarity. Moreover, where terms such as above, below, over, under, top, bottom, side, right, left, etc., are used, it is to be understood that they are used only for ease of understanding the description. It is contemplated that structures may be oriented otherwise.

DETAILED DESCRIPTION

This disclosure pertains to devices and methods used to control, transform or otherwise modulate the delivery of a substance, such as radiopaque contrast, to a delivery site. More specifically, it is the intention of the following devices and methods to modulate the delivery of media to a vessel, vascular bed, organ, or/and other corporeal structures so as optimize the delivery of media to the intended site, while reducing inadvertent introduction (or reflux) of the media to other vessels, vascular beds, organs, and/or other structures, including systemic introduction.

The terms medium (media), agent, substance, material, medicament, and the like, are used generically herein to describe a variety of fluidal materials that may comprise, at least in part, a substance used in the performance of a diagnostic, therapeutic or/and prophylactic medical procedure and such use is not intended to be limiting.

The description, as well as the inventive devices and methods described herein, may be used in modulating contrast media delivery to the coronary vasculature in prevention of toxic systemic effects of such an agent; although, one skilled in the art would recognize that there are many other applications wherein the controlled delivery of a media to a specific vessel/structure/organ/site of the body may also benefit from the devices and methods disclosed herein. For simplicity, these devices and methods may be described as they relate to contrast media delivery modulation. As such, they may be used in the prevention of Contrast Induced Nephropathy; however, it is not intended, nor should it be construed, so as to limit the use to this sole purpose. Exemplary other uses may include the delivery/injection/modulation of: cancer treatment agent to a tumor; thrombolytic to an occluded artery; occluding or sclerosing agent to a vascular malformation or diseased tissue; genetic agent to a muscular bed, neural cavity or organ; emulsion to the eye; bulking agent to musculature and/or sphincter; imaging agent to the lymphatic system; anti-biotics to an infected tissue; supplements in the dialysis of the kidney; to name but a few.

Exemplary Use—Prevention of Contrast Induced Nephropathy

Contrast Induced Nephropathy (CIN) is a form of kidney damage caused by the toxic effects of dyes (radiopaque contrast media) used, for example, by cardiologists to image the heart and its blood vessels during commonly performed heart procedures, such as angiography, angioplasty, and stenting. In general, the dye is toxic and is known to damage kidneys. Although most healthy patients tolerate some amount of the "toxicity," patients with poor or non-functioning kidneys may suffer from rapidly declining health, poor quality of life, and significantly shortened life expectancy. Potential consequences of CIN include: irreversible damage to the kidneys; longer hospital stays; increased risk of heart disease; increased risk of long-term dialysis; and, ultimately a higher mortality risk. For patients who acquire CIN, their risk of dying remains higher than others without CIN, and this risk continues even after five years of their procedure. CIN has a significant economic burden on the healthcare system and currently there is no treatment available to reverse or improve damage to the kidneys, once a patient develops CIN.

To date, there have been attempts in reducing the toxic effects of contrast media on patients who undergo procedures involving dyes, especially those patients who are at high risk for developing CIN. Some of these efforts have been to: change the inherent toxicity (chemical/molecular nature) of the dyes; reduce the total amount of contrast agent injected (through injection management and/or dye concentration); remove media through coronary vasculature isolation and blood/contrast agent collection systems, to name a few. These methods and/or devices used in the control of the toxic effects of contrast agents have had their inherent compromises in effectively delivering a contrast media specifically to a target site while minimizing the systemic effects. As an example, changing the composition of a dye and/or injection concentration may help reduce a contrast agent's inherent toxicity at the expense of the contrast agent's ability to perform its intended function (e.g., visualization of vasculature). Conversely, the ability to "collect" contrast agent laden blood "downstream" from the visualization site may ensure visualization, but requires the complexity of placement and operation of a collection system.

Other attempts to manage the amount of contrast agent delivered to a patient have employed automated (versus manual, syringe injected) contrast media injection systems. Close monitoring and control of the total quantity of contrast agent injected may have a positive impact in the incidence of CIN. However, these injection systems are expensive (including capital equipment and disposables), cumbersome to use within a cath lab, and take additional time and expertise to set-up and operate properly. Improper use could negate any benefits seen by better management of the quantity of the contrast agent delivered to a patient, and the additional time required to set-up such a system may also add significant complexity to a procedure.

Exemplary Use—Coronary Blood Flow and Management of Agent Delivery

Many of the vascular structures and capillary beds of the human body perfuse with enriched, oxygenated blood as a result of the blood being pressurized by the cyclical driving force of the heart during contraction (systole) and decompression (diastole). Most vascular blood flows peak in the body in response to the heart's contractile phase. Because of the cyclical flow of blood in the vasculature, optimization of delivery of any contrast agent to a vascular delivery site may be enhanced through the coordination of an injection's pressure and flow to coincide more closely with that of the vascular site receiving the contrast agent.

Although similar flow principals may apply, the flow of coronary blood is unique in that the perfusion of the heart coronary arteries principally peak during the diastolic (relaxation) phase of the ventricular cycle. As seen in FIG. 1, the pressure of blood in the aorta (from the heart) peaks during ejection (b). However, the flow of blood into the coronary arteries (left coronary artery/left main, as an example) actually peaks after this, during the relaxation/decompression of the heart (i.e., during diastole (c)). Thus, blood flow through the coronary vasculature, in a normal functioning heart, peaks when aortic blood pressure has diminished. This phenomenon appears contra to what one would expect for arterial heart vessel filling. The flow of blood through the coronary vasculature is not necessarily, or completely, "driven" by a high pressure gradient in the aorta into the coronary arteries. In fact, normally the filling of the coronary arteries peaks when the pressure in the aorta is substantially lower than the peak systolic pressure.

It is believed that this phenomenon is derived from a backward travelling, "driving force" or "suction" force of blood that is generated by the relaxing of the myocardium (as well as myocardial microvasculature) during diastole—in essence, during the decompression of the heart. The decompression of the heart in diastole results in a driving wave caused by the relief of the myocardial compression. This force is actually created through a pressure gradient wherein the low pressure of the aorta is actually higher than the vacuum created in the coronary capillary beds—thus, a gradient created from the aorta to the microvasculature.

Further description of this phenomenon may be found, for example, in "Evidence of a Dominant Backward-Propagating 'Suction' Wave Responsible for Diastolic Coronary Filling in Humans, Attenuated in Left Ventricular Hypertrophy" (Circulation. 2006; 113:1768-1778), which is incorporated by reference in its entirety herein.

A challenge in the delivery of contrast agent to the coronary arteries is the cyclical nature of the flow in the arteries (quantity and rate). As further seen in FIG. 1, the pulsatile blood in the arteries may change significantly in flow rate over a single cycle of the heart. In addition, the variation in flow rate transpires over a very short period of time—in many cases, this takes place in less than a second.

FIG. 2 illustrates an example of a blood flow pattern that may be found within a left main coronary artery of a human heart. The illustrated profile of blood flow rate ($Q_{Blood}$, or blood volume flow rate) represents about four cycles of the heart over a period of time that is less than four seconds. The average flow rate of blood (e.g., mean $Q_{Blood}$) in this example averages about 3.7 ml/sec over a single cycle of the heart, and may vary significantly during each cycle from about 1.3 ml/sec to about 6.5 ml/sec. In this example, the left main is approximately 4.4 mm diametrically and has a length about 5 mm before it bifurcates into the left anterior descending artery and the left circumflex artery. It should be noted that this is only an example and any physiological, anatomical, or fluid flow characteristics described may vary significantly between patients, as well as within the same patient. These variations may occur as a function of age, vascular and/or coronary disease, vascularity and collateralization of the heart, metabolism, blood pressure, patient activity, stress level, functional status of various patients' organs, patient weight, vasodilatory and/or constrictive medicants, and chemical or biochemical mediators, to name but a few of the involved variables. Therefore, the example is intended to help elucidate the disclosure of the devices and methods herein, and is not intended to limit their use.

In further illustrating the inventive devices and methods herein, an example of a use of the system will involve the delivery of contrast agent to the left arterial system of the heart during the performance of a treatment procedure (e.g., stent delivery). However, this exemplary use should not, in any way, limit the use of the devices and methods described.

Referring to FIG. 3A, a catheter, therapy, or treatment system 10 is shown that may be used in the treatment of an occlusion in a coronary vessel. FIG. 3B further highlights the distal portion of the catheter system, proximate a left coronary artery ostium. As seen in FIG. 3B, the system 10 includes a system delivery catheter 12 (e.g., guide catheter) and occlusion treatment devices (e.g., balloon catheter 14 with stent 16 and guide wire 18). The distal end of the guide catheter 12 is placed proximate an opening 20 (ostium) of the aorta 22 to the left coronary artery 24 (left main), off of the aortic root 26. The system 10 may be placed by percutaneous advancement of the system 10 from the femoral artery (not shown) to the aortic root 26. FIG. 3C further illustrates a proximal portion of such an arterial occlusion treatment system 10 (including a balloon catheter with stent, guide wire, connectors, etc.) shown in FIGS. 3A and 3B. Typically, there is a guide catheter connector 28 that may have a Tuoy-Borst compression fitting 30 attached to a proximal portion of the connector 28. The treatment devices may be passed axially through an outlet of the connector 30 and into a primary lumen 32 of the connector 28, and then into the guide catheter 12. The fitting 30 of the connector 28 may be adjusted so as to allow passage of the treatment devices through connector 28, but resist back flow of fluid out of the guide catheter 12 and connector 28. In addition, the connector 28 may have a secondary lumen 34 displaced laterally of, and in communication with, primary lumen 32. Secondary lumen 34 may terminate in luer-fitting 36. A manifold assembly 38 with multiple ports (e.g., ports 38a, 38b) may be attached to luer fitting 36. These additional ports of the manifold 38 may be used to infuse various media through the guide catheter 12 (e.g., within a flow conduit defined by an inner lumen of the guide catheter, and the outer proximities of any treatment system components 14, 16, 18 therein). Such infusions may include, for example, radiopaque contrast, medicaments, or saline for flushing the guide catheter 12.

The treatment system 10 described in FIGS. 3A-3C may be comprised of components that may be used in such a procedure, such as a 6 F guide catheter having an approximate length of 100 cm and an inner diameter of approximately 0.070 inch. Further, the treatment devices (e.g., balloon catheter, stent, guide wire, etc.) might have an outer diameter of 3.2 F proximally and 2.7 F distally. The delivery of the treatment devices may be accomplished by passing the balloon catheter through the guide catheter and over a guide wire of 0.014 inch in diameter. The injection of contrast agent for the visual assessment of the vasculature may be performed by activating an injection device 40 (such as an injector or syringe), as seen in FIG. 3C. In this case, the contrast agent may pass from the injection device 40, through a tubing connector 42 (i.e., between injection device 40 and manifold 38), the manifold 38, the guide catheter connector 28, and ultimately through the co-axial conduit defined between the guide catheter inner diameter and the treatment catheter system (e.g., balloon catheter) outer diameter.

This example is illustrative of a treatment procedure and should not be limited to the various assemblies that may be deployed for any given procedure, or by any specific physician. The various infusions of the given example may be introduced through the manifold connections by numerous means, to include manual injection (i.e., syringe), automatic injection with an injection machine, or a "gravity fed" injection arrangement. How perfusions/infusions of various substances may be administered may depend on the medium and the intended therapy. In FIG. 3C, a syringe is shown connected to the manifold with a tubing connector, providing means to hand-inject contrast medium through the manifold and to the distal outlet of the guide catheter. Conversely, a power injector may be attached to the manifold to perform the injection, as an alternative configuration.

Moreover, the example described is illustrative of a treatment procedure comprising a "guide catheter" in conjunction with a treatment system. However, there are a multitude of constructions of conduits that may be capable of delivering, or otherwise mediating the delivery, of substance from a proximal portion of a system (outside of a body) to an intended corporeal site. And thus, reference to a "guide catheter" or "catheter" in the example could be described as a tube, delivery catheter, or any other conduit used in mediating the delivery of a substance; and as such, should not be limited to the various assemblies for the exemplary procedure.

FIG. 4A illustrates an exemplary hand-injection flow rate profile ($Q_{Agent}$) of contrast media that may be delivered through a catheter treatment system such as described above. In the example of FIG. 4A, flow rate ($Q_{Agent}$) is described. However, it should be apparent to those skilled in the art that a pressure profile could have been used to describe the concepts herein since there is a direct relationship between the flow rate (Q) and the pressure drop (dP or ΔP) over a conduit.

In the example of FIG. 4A, an injection profile of $Q_{Agent}$, as delivered to the distal tip of the guide catheter, represents approximately 10-12 ml of contrast media injected over approximately 3-4 seconds. This may be a fairly typical hand-injection for illuminating the left coronary vasculature over 2 to 5 cycles of the heart (while performing a stenting procedure); although, such injections may vary significantly (e.g., from 3 ml to 30 ml over periods of 1 to 8 seconds). It should be noted that some clinical investigators (and injector manufacturers) have suggested using around 5 ml/second flow rate of agent ($Q_{Agent}$) for a left heart injection. However, these recommendations may have been derived solely on the optimization of vessel opacification, with little regard for over-use of contrast media. Over-injection may result in unnecessary delivery of contrast media systemically. It is the objective of at least some of the embodiments herein to modulate systemic contrast induction, and therefore minimize "over-injection" (injection that is greater than necessary for the contrast agent to effectively perform its opacification function).

In a coronary angiography procedure, a hand-injection is normally administered with increasing pressure, and thus volume, until contrast media is "seen" filling the coronary vasculature radiographically. At this point, the administration continues for about 3 seconds until the quantity of contrast media (e.g., approximately 10 ml) within the injector is used. For an automatic injector, typically the pressure or volume may be set (e.g., 5 ml/sec) and then the operator may activate the automatic injector with a hand-held actuator for several cycles of the heart.

The exemplary injection profile $Q_{Agent}$ shown in FIG. 4A reveals an increasing injection (flow rate, which is directly related to pressure). $V_i$ on the graph of FIG. 4A represents a minimum level of injection flow rate that may be necessary for the operator to "see" vascularity as a result of visualizing the contrast medium. In essence, $V_i$ is an injection rate of media that may be delivered to a vessel, or organ, wherein $V_i$ is a level known, or believed to be, an acceptable concentration of the substance to provide its intended function. In this case, $V_i$ is the level of delivery wherein the concentration of contrast media injected to the left main is of sufficient quantity to opacify the vasculature, on the average, over several cycles of the heart. $V_i$, as shown in this example, is approximately 3.0 ml/second. That is to say, with an injection of a constant 3.0 ml/second of contrast media the operator may effectively visualize the vasculature, while not over-injecting contrast media. In this exemplary context, an injection meaningfully less than $V_i$ will not provide adequate opacification. The exemplary injection of profile $Q_{Agent}$ in FIG. 4A results in a total volume of approximately 11 ml of contrast media delivered.

Referring to FIG. 4B, various areas are shown which may have (by definition of $V_i$) injection flows that are either insufficient to opacify the vessel appropriately (areas A and B), or are of a magnitude greater than is necessary for opacification, and may thus result in the over-delivering of contrast agent (area C). That is to say, if the injection had been controlled in the delivery of the contrast agent to obtain $V_i$ (identified as a rectangle within the injection rate profile $Q_{Agent}$ of FIG. 4B), approximately 3 ml less of contrast (25% to 30%) might have been used to achieve the same result (e.g., to sufficiently visualize the artery over the same period of time). Therefore, an injection flow rate profile $Q_{Improved}$ shown in FIG. 4C may outline an "improved" constant flow rate of injection for $V_i$ (i.e., wherein the injection flow rate may be held at a constant rate sufficient for visualization).

As a practical matter, and in further illustration of the complexity in efficiently delivering contrast agent into the dynamic environment of a coronary artery, some operators of the injector (a syringe, for example) may try to mimic a rapid injection so as to minimize the area of A in FIG. 4B through a rapid increase of pressure (and commensurate volume flow rate) with an injection. When sufficient opacification is "seen" radiographically, the operator may then decrease the pressure (and volume flow rate) of the injection. This technique may be helpful in reducing the area of A (quickly reaching $V_i$); however, the operator may "overshoot" the delivery rate required to the vessel for opacification (i.e., $V_i$) and thus increase the amount of over-injection which may be seen by area C in FIG. 4B. It should be noted that a 10 cc (ml) syringe may be capable of injecting at 100 psi or more. This pressure of injection from the syringe could generate flows as high as 4.0 ml/second in the exemplary system described above; whereas, only 75 to 85 psi may be needed to inject 3.0 ml/second, as an example.

FIG. 4D illustrates the exemplary flow of blood in the left main (e.g., left main 24 of FIG. 2), noted as blood flow rate profile $Q_{Blood}$ super-imposed with an exemplary profile of an injection flow rate of contrast (e.g., profile $Q_{Agent}$ of FIGS. 4A and 4B) over-laying the blood flow pattern. In this example, we have additionally assumed that the start of the injection begins at about the same time as systole (compression of the heart with lower blood flow rates). However, from a practical point of view, timing of the beginning of an injection may happen at any time during the heart cycle since it may be difficult to synchronize injections with the vessel blood flow. As can be seen in FIG. 4D, an injection at a constant $V_i$ flow rate (or, as described by $Q_{Improved}$ in FIG. 4C), although notably better than no modulation (e.g., $Q_{Agent}$) may still result in over-injecting contrast media (at times) since the blood flow rate (e.g., $Q_{Blood}$) is less than the rate of injection (e.g., $V_i$ or $Q_{Improved}$). In this case, the areas D in FIG. 4D may indicate such over-injection, where contrast may be injected into the aorta (as an example) rather than into the left main artery.

In describing this example further, the arrows in FIGS. 5A and 5B illustrate flows $Q_{Blood}$ (arrow 50) and $Q_{Agent}$ (arrows 52) during injection of contrast agent during different phases of the heart cycle. When the injection of contrast medium is greater than the blood flow in the vessel 24 (FIG. 5A) there will be a tendency for the contrast media to flow to the least path of resistance. In this case, some of the contrast media may flow to the aorta 22 and, consequently, systemically. Conversely, when the blood flow ($Q_{Blood}$) in the vessel is greater than the injection flow ($Q_{Agent}$), the flow of contrast media may preferentially pass into the vessel 24 (FIG. 5B). In other words, the injection flow rate ($Q_{Agent}$) illustrated by arrow 52 in FIG. 5B will follow the blood flow rate ($Q_{Blood}$) illustrated by arrow 50.

Various embodiments of the inventive devices and methods will now be described in further detail. Many of these embodiments may control, transform or otherwise modulate a pattern of medium, agent, substance, medicament, or fluidal material delivery to a vessel, vascular bed, organ, or/and other corporeal structures so as optimize the delivery of media to the intended site, while reducing inadvertent introduction (or reflux) of the media to other vessels, vascular beds, organs, and/or other structures, including systemic introduction. Some of these embodiments may modulate an injection, such as the example shown in FIG. 4A, by controlling the flow rate profile of an injection to attain a profile designed to reduce inefficient agent use (e.g., areas A, B and/or C in exemplary injection profile $Q_{Agent}$ of FIG. 4B), and to obtain an "improved" injection profile $Q_{Improved}$ in FIG. 4C.

Exemplary Modulation Devices and Methods

Some of the "modulators" in the following examples may be located at various locations proximate the proximal portion of the therapy system 10, as described in FIGS. 3A-3C. For example, a modulation controlling mechanism may be positioned on the injection device outlet, between the injector 40 and the manifold 38, between the manifold 38 and the guide connector 28, as well as between the guide connector 28 and the guide catheter 12. Some other embodiments may also include directly controlling the performance of the injection device 40. The placement of the modulator may also be highly dependent on the diagnostic, prophylactic or therapeutic procedure to be performed and, as such, the positioning should not be limited by the examples used herein.

In addition to locations described above, some inventive embodiments of fluid modulators may alternatively be positioned in, and/or around, and/or proximate the distal portion of the guide catheter/delivery catheter 12.

Furthermore, some embodiments of control devices disclosed herein may advantageously receive a sensor signal so as to coordinate a valving, controlling, or otherwise modulating function on an injection agent before the agent enters an intended target injection site.

Figure 6A:
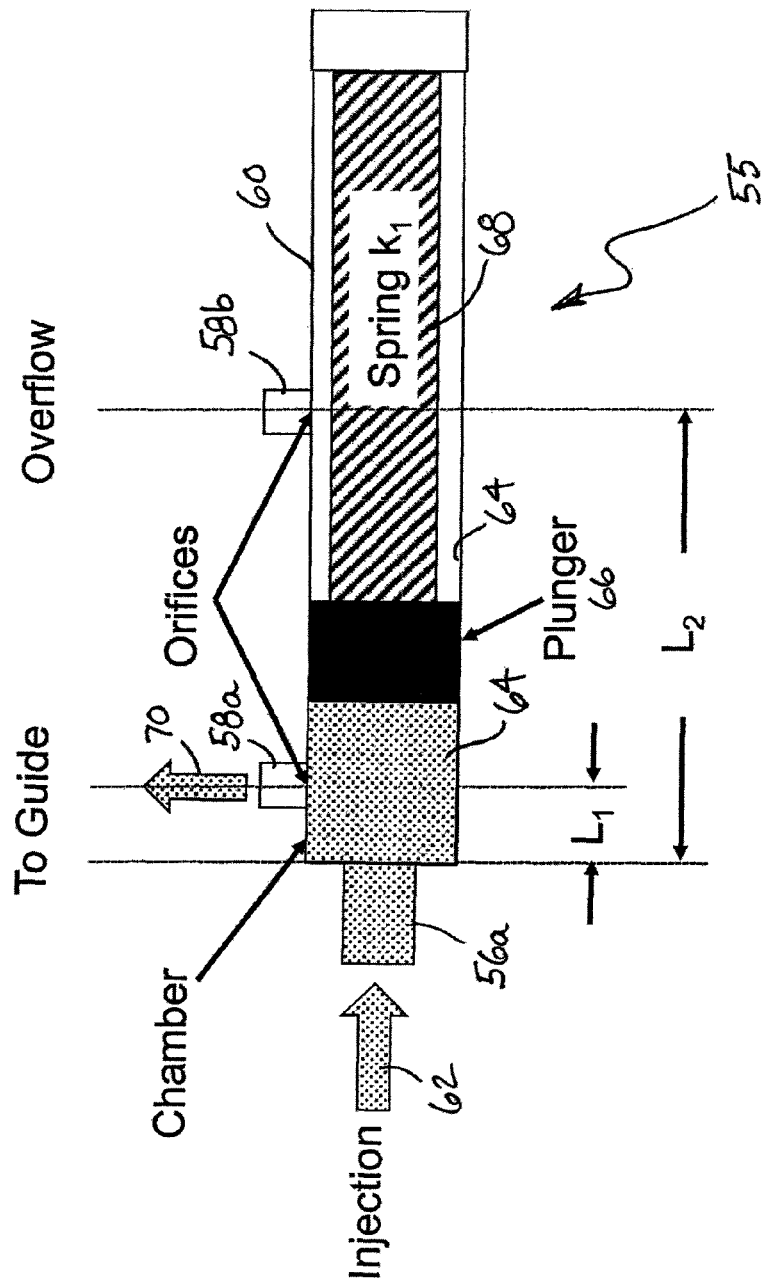
FIGS. 6A and 6B illustrate an exemplary single chamber flow modulator, in different stages of flow control.

One exemplary embodiment of a modulation device 55 is shown in FIG. 6A. Device 55 may be positioned within the exemplary system 10 of FIG. 3C, as shown in FIG. 6C. As such, an "injection" port 56a of modulator 55 has a connector 56 coupled by tubing 42a to injection device 40, and an outlet port 58a of the modulator 55 has a connector 58 coupled by tubing 42b to manifold 38. FIG. 6A shows the exemplary modulator 55 comprising a body 60 having three ports thereon. One of these ports (the "Injection" port 56a) receives an injection of agent from injection device 40. A "To Guide" port (outlet port 58a) delivers agent from device 55 to the manifold 38, and subsequently through the guide 12. An "Overflow" port (outlet port 58b) is activated upon over pressurization by the injector 40 to the modulator 55, so as to release excessive agent out of the system 10 (i.e., out of device 55).

An example of how such a modulator may function may be determined by the injection parameters (i.e., pressure, volume, flow rate, etc.) intended to improve the delivery of the agent. For example, $V_i$ of FIG. 4 (with the exemplary treatment system use as described for and by FIG. 3) may be approximately 3.0 ml/second. Using various flow equations for flow within a conduit (assuming some amount of laminar flow), such as those shown in FIG. 7, an injection pressure level (from the injector, for example) may be derived to provide an agent flow rate delivered from the distal end of the guide catheter. With a set-up and dimensions as described, a pressure of 75 psi (at or around the proximal portion of the guide catheter) may sufficiently produce about 3.0 ml/second of $Q_{Agent}$ delivered to the distal tip of the guide catheter positioned at the ostium to the left main. This example is intended to be illustrative for the purpose of description and, as such, should not be restrictive or limiting in the scope of the devices and methods described and disclosed herein. For example, if the treatment device (e.g., balloon catheter 14, stent 16, and wire 18) described above were to have a different construction (than previously described), such as a proximal and a distal outer dimension of 2.7 F, only 43 psi may be necessary to produce approximately 3.0 ml/second of $Q_{Agent}$. Alternatively, utilizing a guide catheter (e.g., delivery catheter 12) with different inner diameter dimensions might be used in producing a medium flow rate of about 3.0 ml/second, at a lower pressure differential. For example, the guide catheter could be larger (0.076 inch inner diameter/6.5 F outer diameter) in corporeal areas less critical in the performance of the treatment (e.g., descending aorta), while providing advantages of a smaller treatment system (e.g., guide catheter having 0.70 inch inner diameter/6 F outer diameter) in proximity of the treatment region (for example, 30 centimeters of the guide catheter 12 distal portion). Advantageously, agent flow rate of approximately 3.0 ml/second may be accomplished at about 50 psi, while not sacrificing the benefit of a smaller treatment system within the coronary vasculature. In summary, therefore, it is not the intention per se to describe all possibilities of various constructions of treatment systems and improvements thereto, but rather it is to provide examples of how one might construct exemplary devices for use in such exemplary treatment systems as described herein.

Referring to FIG. 6A, injection of agent from an injection device (as indicated by flow arrow 62) may enter a chamber 64 of modulator body 60 having a spring-loaded plunger 66 therein. The plunger 66 in this example (and in others to follow) may be in sealing, but sliding, relationship with the chamber 64—such as one might find in a syringe. Compression spring 68 (providing, e.g., spring constant $k_1$) may be positioned within the side of the chamber 64 opposing the force of injection and configured so as to resist movement of the plunger 66 against the force applied by filling the chamber with agent from the injector. As the agent injection pressure increases in chamber 64, the plunger 66 may move against the compression spring 68. The force generated by the spring 68 against the pressure of injection will be defined by the spring's spring constant (k) and the distance (L) the spring has been compressed, or otherwise displaced from its equilibrium (Hooke's Law, F=−k*L). FIG. 6A shows a displacement of the spring 68 (at plunger 66) within the chamber 64 of a distance greater than $L_1$. In this example, displacement of the spring/plunger equal to, or greater than, $L_1$ may allow passage of the pressurized agent to flow through an orifice in the chamber 64 and then through the "To Guide" port 58a at a minimum, threshold pressure (such as indicated by flow arrow 70). In the example described above, we have hypothetically selected a pressure of about 75 psi to produce the intended flow of agent. That is to say, when the force within the chamber 64 is equal to 75 psi/(cross-sectional area of the plunger/chamber), the force derived from the compression of the spring 68 over a distance $L_1$ should be about equivalent. The spring 68 used in producing such a force would have a spring constant (k) to optimally produce an equivalent force over the displaced length. This modulator construction may advantageously produce an injection flow profile of agent that allows flow to the guide at some intended flow rate that may be radiologically visible (i.e., $V_i$). In our example, $V_i$ may be 3.0 ml/second.

Figure 6B:
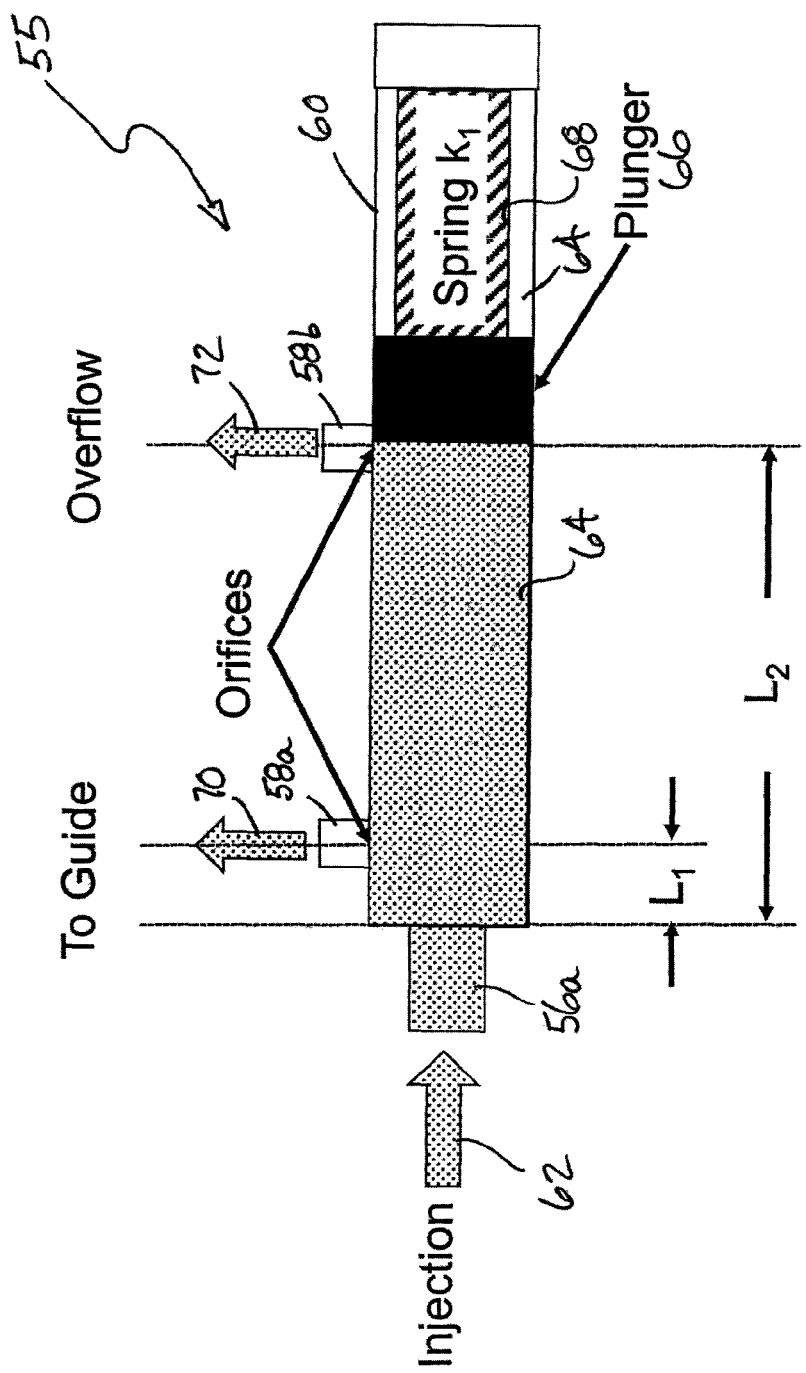

Furthermore, as an injection of agent into the modulator 55 is increased in pressure, the plunger 66 of FIG. 6B may continue compression of the spring 68 along the longitudinal axis of the chamber 64 so as to expose a second orifice in the chamber 64 (e.g., to the "Overflow" port 58b) at $L_2$ wherein the highly pressured agent may be diverted away from introduction into the guide 12 (such as indicated by flow arrow 72 in FIG. 6B). For example, it may be determined that an acceptable working range of a modulator may be 75 psi to 80 psi, to produce controlled injections with flows in the above example of about 3.0 ml/second to about 3.1 ml/second. The displacements of the spring 68 with spring constant $k_1$ at $L_1$ and $L_2$ could define these operating pressures/flow rates. An injection greater than 80 psi will result in the excessive injection being bled-off into the "Overflow" port 58b, and not introduced systemically. Moreover, if the injection should fall below 75 psi, no agent will pass into the system (the plunger would be moved within the chamber by the spring such that both orifices of the chamber would close due to insufficient pressure). The exemplary modulator described may advantageously produce an improved injection flow profile, reducing inefficient agent use as illustrated as areas A, B and/or C in exemplary injection $Q_{Agent}$ profile of FIG. 4B, and resembling (within a working range), an "improved" injection profile $Q_{Improved}$ of FIG. 4C.

Figure 8A:
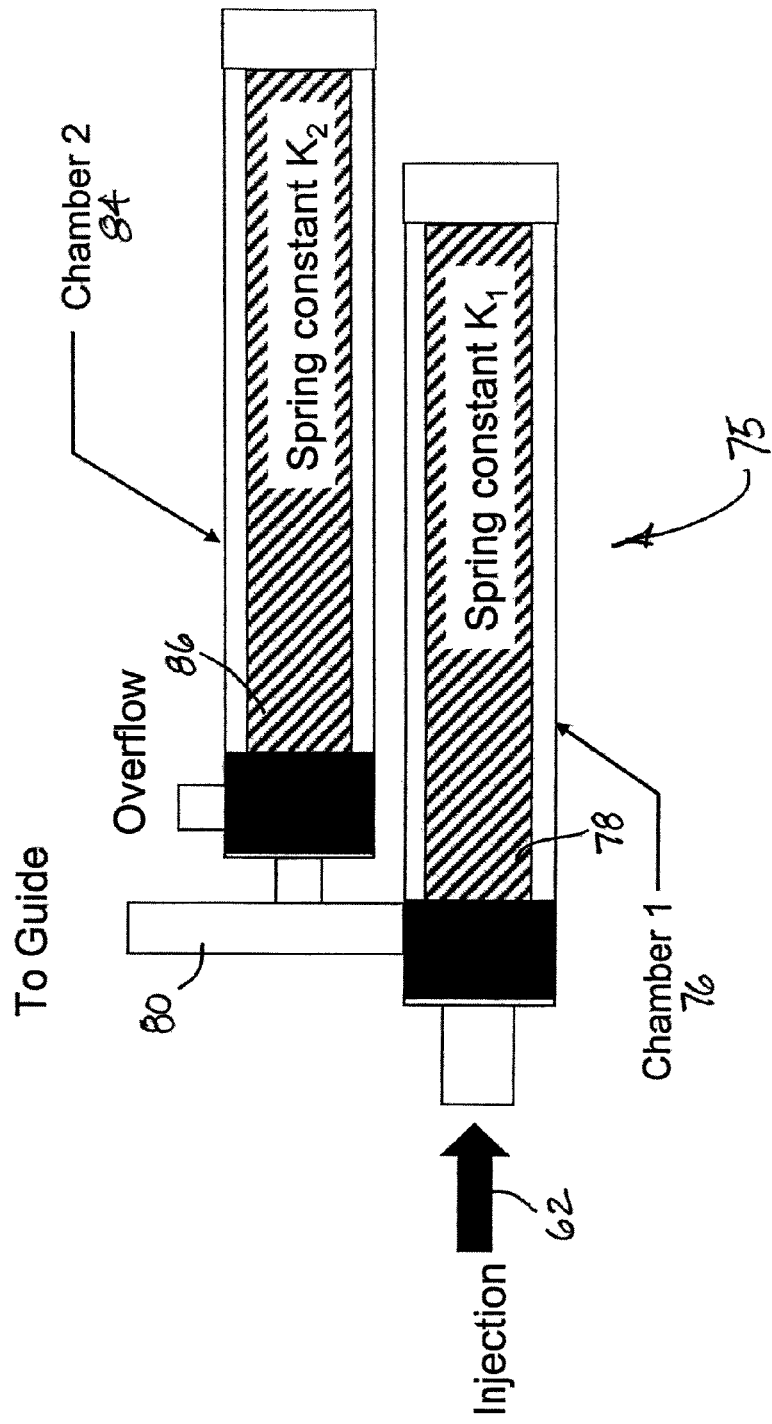
FIGS. 8A, 8B and 8C illustrate an exemplary two-chamber flow modulator, in different stages of flow control.
Figure 8B:
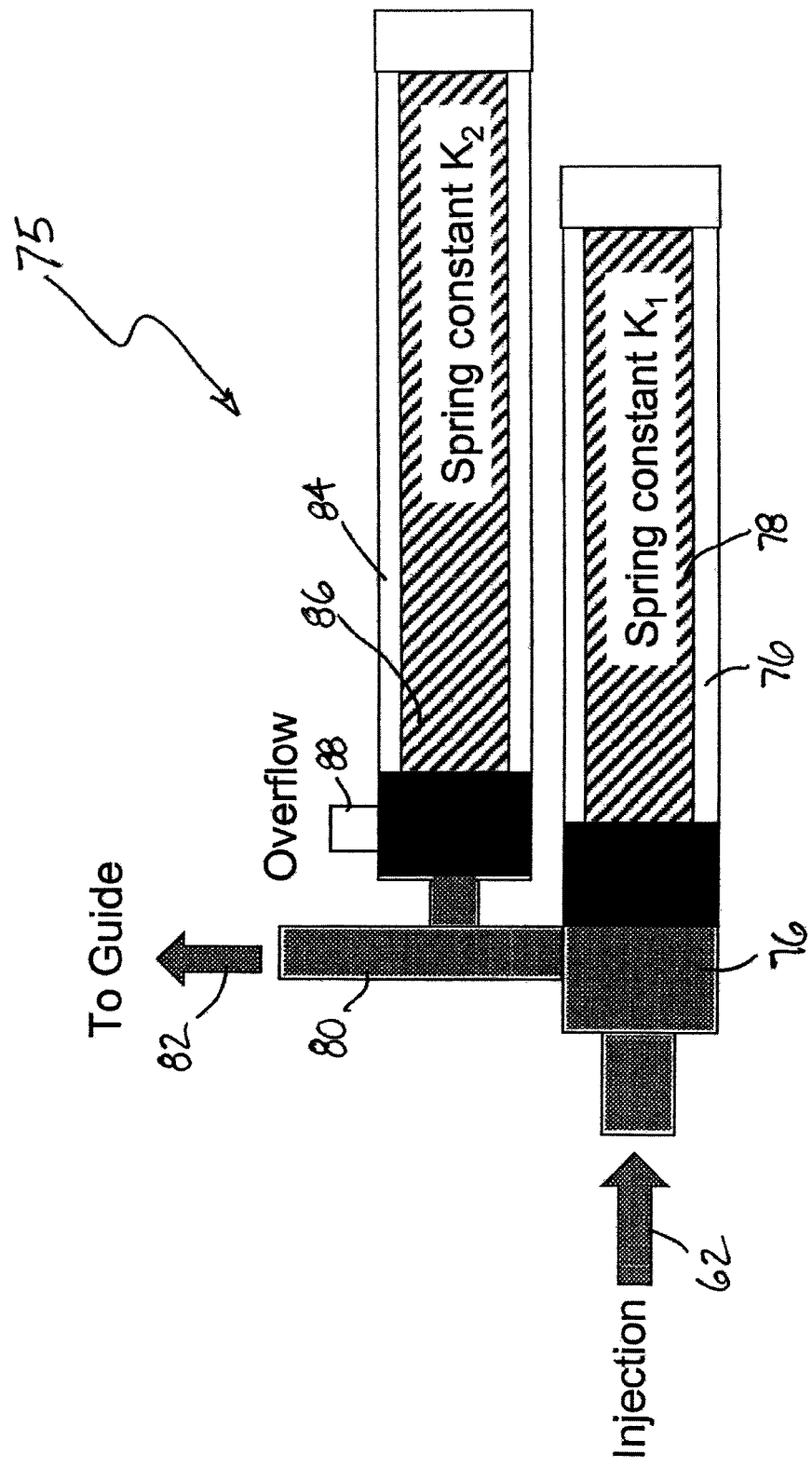
Figure 8C:
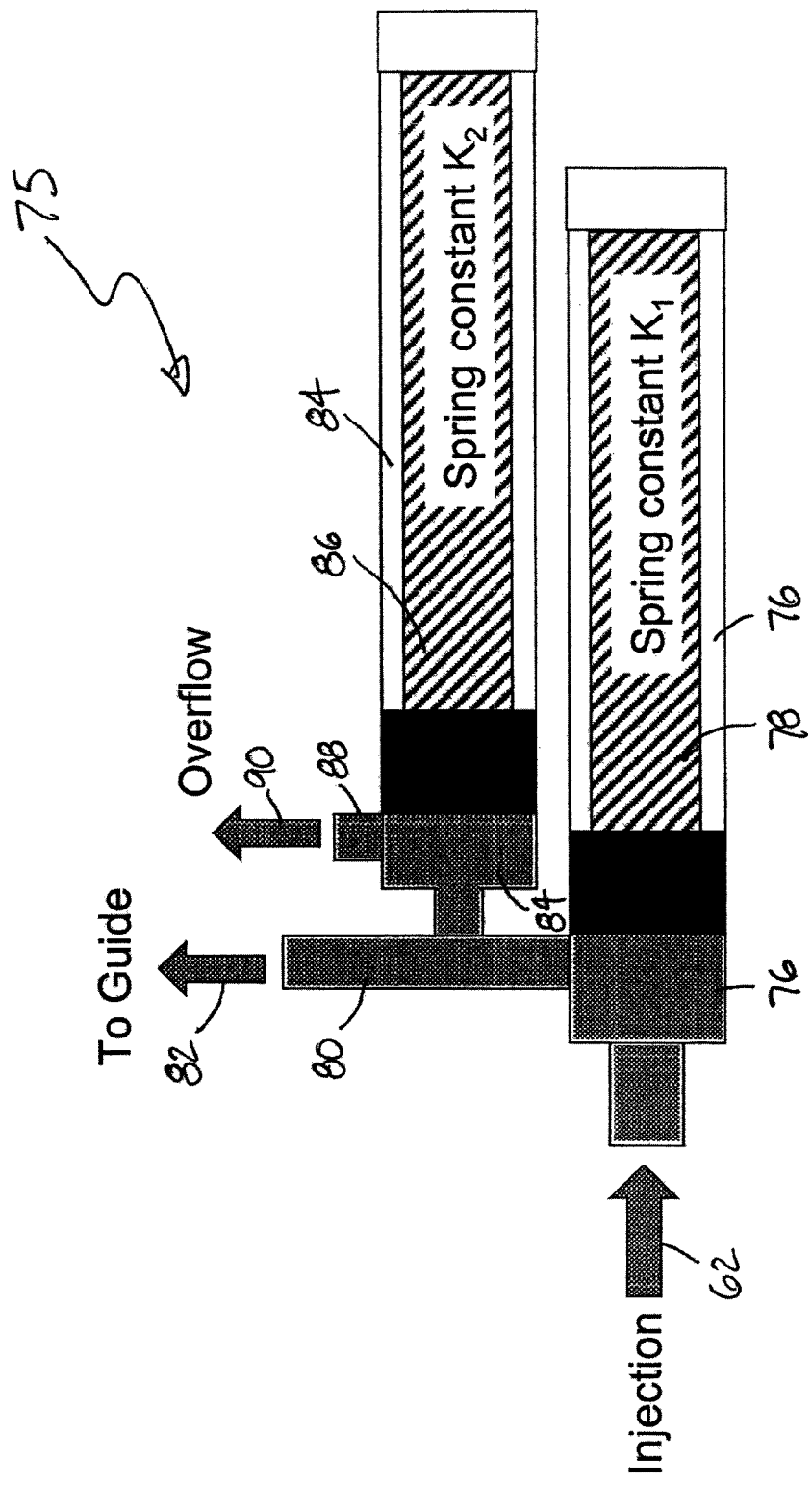

An alternative embodiment of a controlling device 75 may be of the construction as shown in FIGS. 8A-8C. In essence, a single chamber device such as illustrated in FIG. 6 may be replaced by a double chamber configuration so as to provide greater fidelity in the selection of modulator working pressures/flow rates.

As shown in FIG. 8A, there may be two separate tanks or chambers with two compression springs (having spring constants of $K_1$ and $K_2$). Medium from the injection device may be delivered to the device 75 as in device 55 of FIG. 6C (as illustrated by flow arrow 62), or any of the alternative locations described herein. Fluid flow from the injector enters chamber 1 (tank 76) and compresses plunger/spring 78 of chamber 1 until an intended pressure (and commensurate flow rate) is obtained. When the intended pressure/flow is obtained (i.e., $V_i$ at 75 psi of the previous example), the flow of medium passes via an orifice in chamber 1 and out the "To Guide" port 80, as shown in FIG. 8B (such as indicated by flow arrow 82). Chamber 2 (tank 84) is in fluid communication with port 80 and may also be pressurized by the injection. Fluid flow from the injector (via port 80) enters chamber 2 and compresses plunger/spring 86 until another compression level is reached within chamber 2, at which point plunger/spring 86 in chamber 2 will compress to a point that the passage of fluid is allowed, via an orifice in chamber 2, into port 88 (the "Overflow" port). As shown in FIG. 8C, the "decompression" of chamber 2 acts as a "relief valve" and reduces the pressure of the fluid going to the "To Guide" port 82 if the pressure in chamber 2 exceeds an upper-end threshold (i.e., 80 psi in the example of FIG. 6). Any additional pressure/volume will be bled-out of the system via port 88 (such as indicated by flow arrow 90 in FIG. 8C) and not introduced through the guide. In operation, the use of a device such as device 75 with an agent injection system may likewise produce an "improved" injection agent flow profile, reducing inefficient agent use as illustrated as areas A, B and/or C in exemplary injection profile $Q_{Agent}$ of FIG. 4B, and resembling (within a working range) the "improved" injection profile $Q_{Improved}$ of FIG. 4C.

Figure 9A:
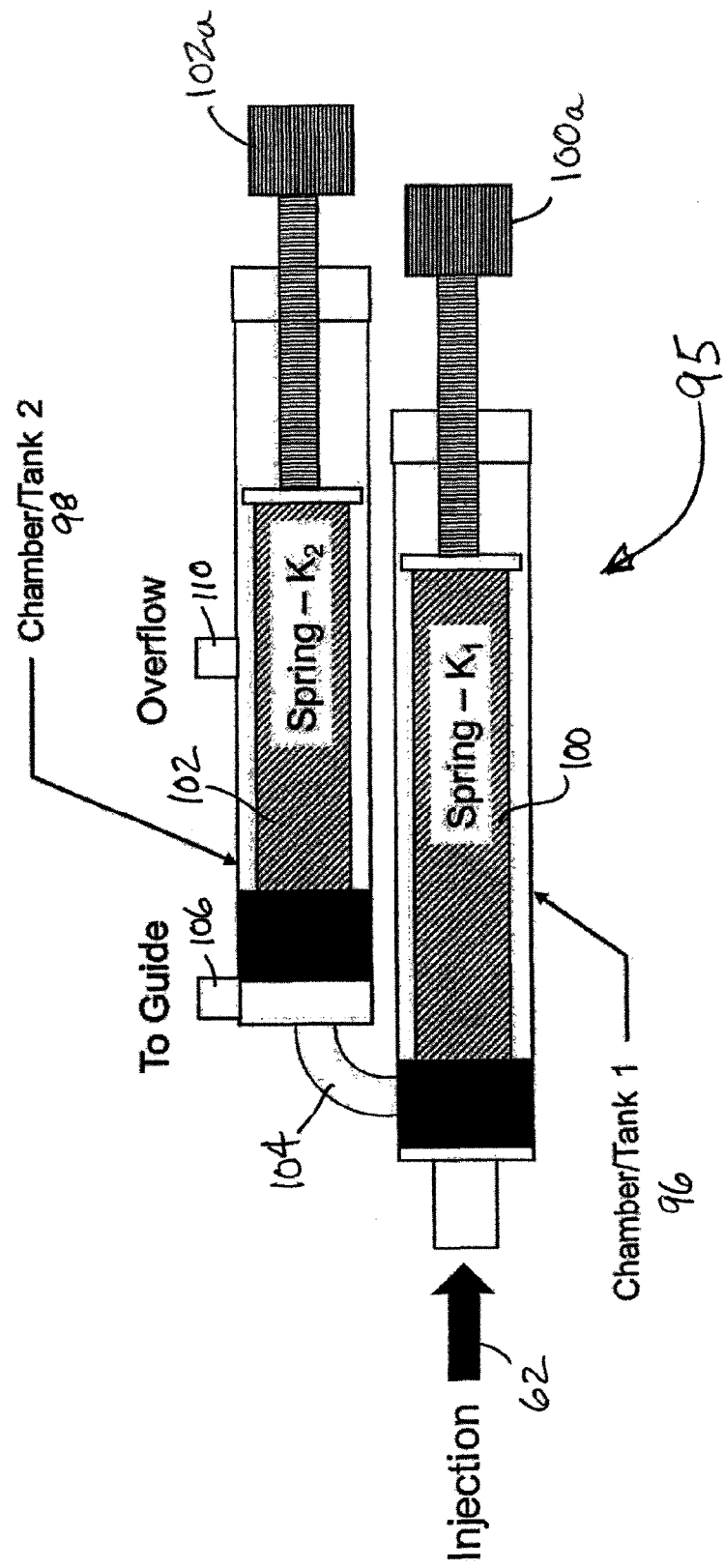
FIGS. 9A, 9B and 9C illustrate an exemplary two-chamber flow modulator with holding chamber, in different stages of flow control.
Figure 9B:
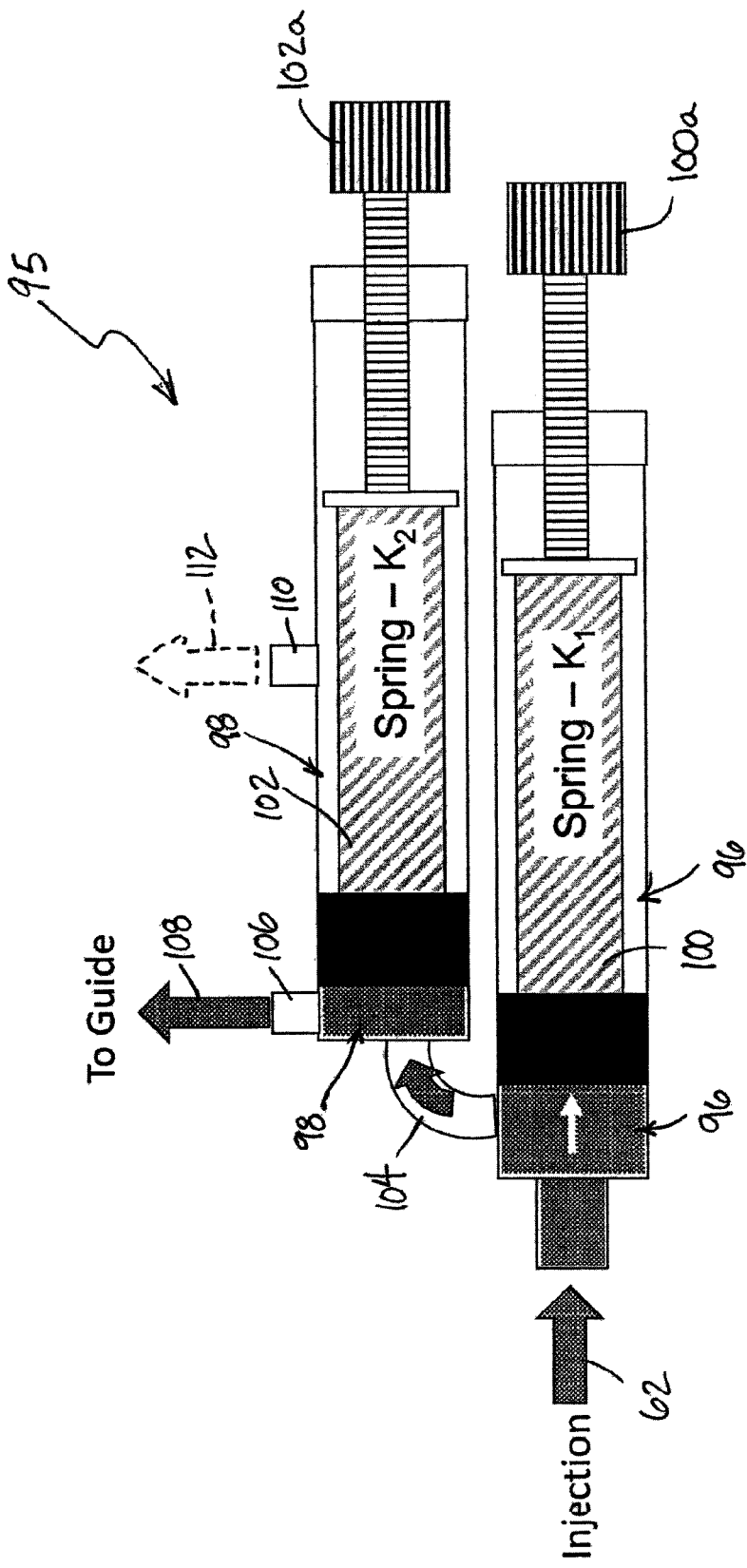
Figure 9C:
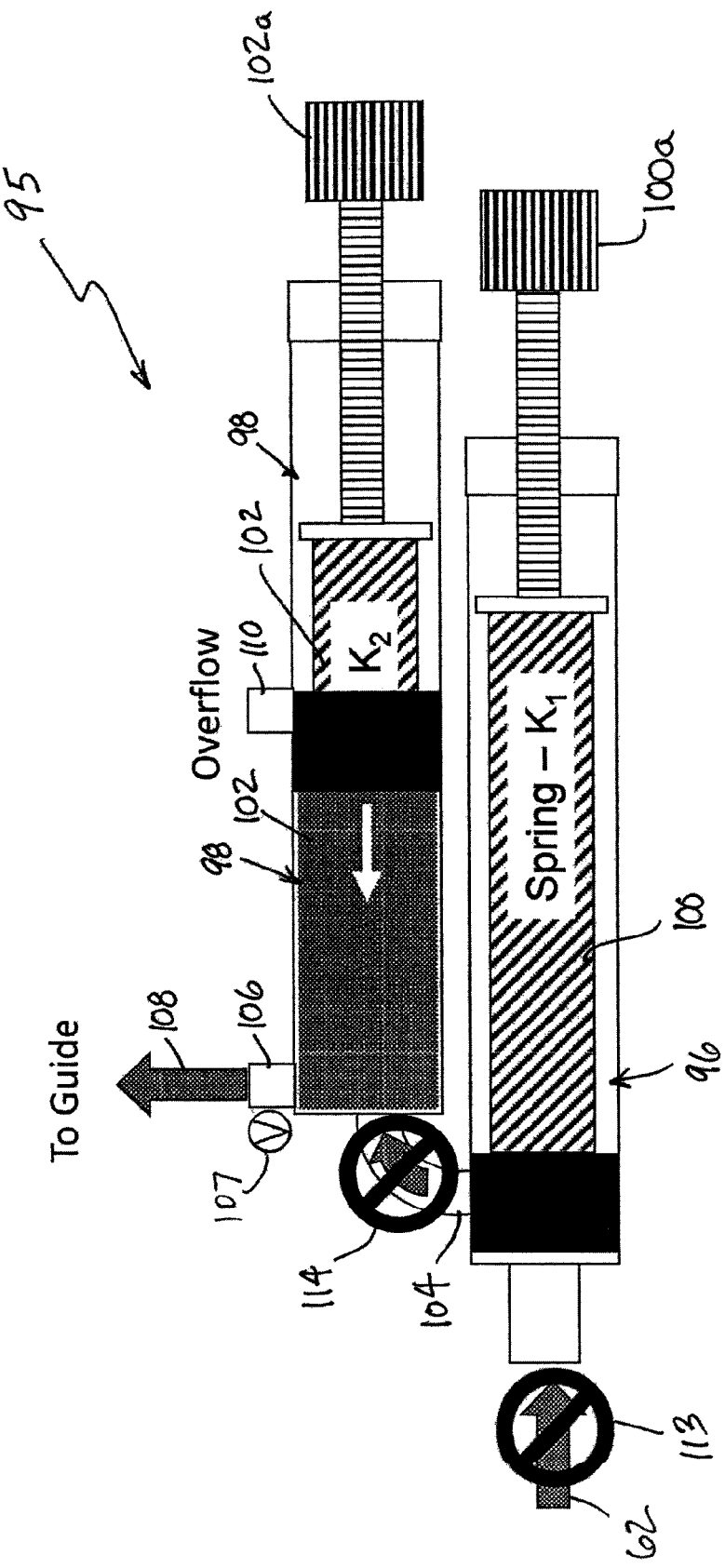

Advantageously, an alternative modulator design, as shown in FIGS. 9A-9C, might also accommodate cessation of injection from the injection device without fully ceasing the injection of medium to the guide. For example in a modulator 95 having two chambers or tanks 96 and 98 such as shown in FIG. 9A, tank 2 might include a compression spring with a lower spring constant than the compression spring in tank 1, but allow more filling of the tank 2 (i.e., greater compression length of its spring), while providing flow to the guide at an intended rate. In essence, tank 2 might act as a "holding tank" of the injection.

In further viewing FIG. 9A, the modulator 95 may comprise two tanks 96 and 98 with two compression springs 100 and 102 (with spring constants of $K_1$ and $K_2$ respectively). Medium from the injection device may be delivered to the device as in the device of FIG. 6B (as again illustrated by flow arrow 62), or any of the alternative locations described. Fluid flow from the injector enters chamber 1 and compresses plunger and spring 100 of chamber 1 until an intended pressure (and commensurate flow) is obtained. When the intended pressure/flow rate is obtained, the flow of medium passes out of chamber 1 via an orifice and into chamber 2 via channel 104, and then out the "To Guide" port 106, as shown in FIG. 9B (as illustrated by flow arrow 108 in FIG. 9B). In essence, chamber 1 provides chamber 2 with a pressurized flow of a value equal to, or greater than, some intended limit (i.e., a minimum threshold, such as 75 psi). If chamber 2 should pressurize with fluid greater than an upper threshold of some working pressure (for example, 80 psi) spring 102 of chamber 2 may compress to a point to allow passage of fluid out of chamber 2 via another orifice and into port 110 (the "Overflow" port) with any additional pressure/volume bled-out of the system, and not introduced through the guide (as illustrated by flow arrow 112 in FIG. 9B). Again, an injection system equipped with a device such as device 95 may aid in producing an "improved" agent injection profile similar to profile $Q_{Improved}$ in FIG. 4C.

Although the previous example describes using device 95 as simultaneously injecting a medium while delivering the medium to/through the guide catheter, the device 95 may also be employed to deliver the medium in a "sequential" fashion. For example, to "sequentially" inject a medium (i.e., fill a chamber with a medium to be delivered, but allow time before release of the injection), or avoid an interruption in the delivery of a medium, the device 95 of FIG. 9C may advantageously continue to deliver medium to the "To Guide" port 106 as spring 102 decompresses. As shown, the cessation of the injection 62 at a minimum level (as illustrated at 113 in FIG. 9C) may result in the cessation of medium delivered via channel 104 from chamber 1 (as illustrated at 114 in FIG. 9C) to chamber 2 since spring 100 has sufficiently decompressed so as to occlude the orifice in chamber 1 into channel 104, thus stopping the flow of medium from chamber 1 to chamber 2.

In this example, tank 2 may "bleed-out" the medium contained within tank 2 while no additional medium is injected into the device 95. The device 95 of FIGS. 9A-9C might also have a "relief" mechanism or one-way valving type system (such as valve 107 in FIG. 9C) attached to the "To Guide" port to assure that a minimum pressure is maintained as chamber 2 decompresses (i.e., a relief valve that only operates above the intended pressure of, say 75 psi and only allows flow to the guide if minimum pressure is maintained). Conversely, the spring of chamber 2 may also be designed to "close" the orifice to the "To Guide" port if a minimum level of pressure is not maintained. FIGS. 9A-9C also illustrate knurled-knob bolts 100a and 102a threadably extending from tanks 1 and 2, and attached to springs 100 and 102, so as to provide a mechanism for independently adjusting the forces delivered by their respective plungers.

Figure 10A:
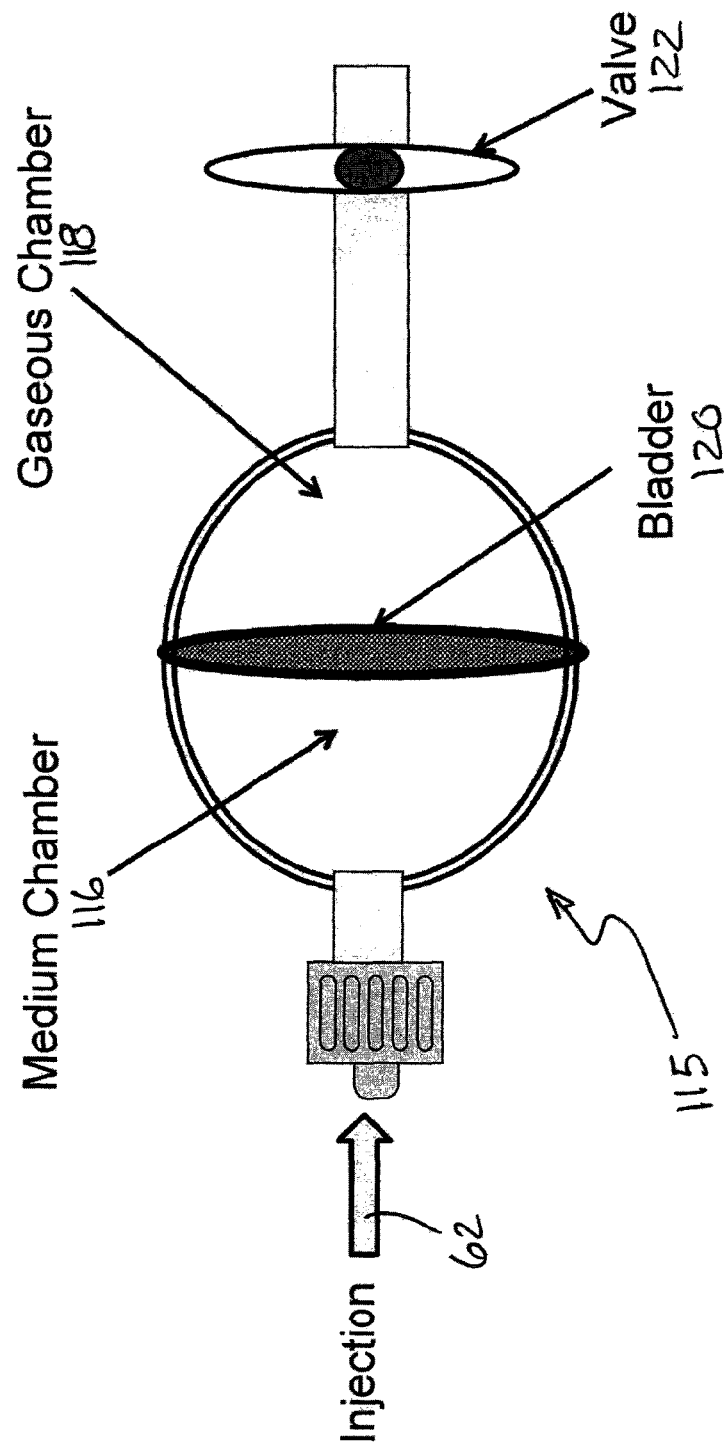
FIGS. 10A and 10B illustrate a capacitance chamber flow modulator (bladder), in different stages of flow control.
Figure 10B:
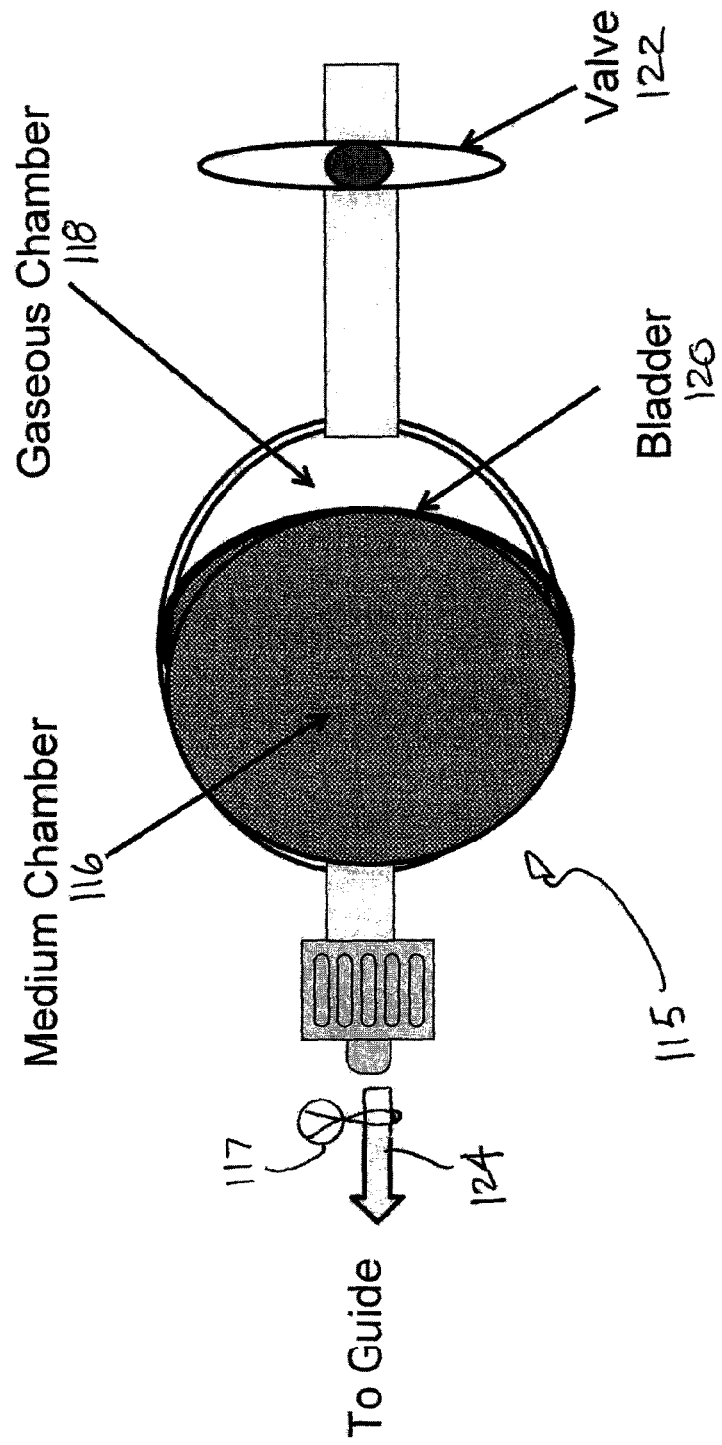

An alternative example of a regulator that could be used for sequential or/and simultaneous injection may be seen in FIGS. 10A and 10B. In this exemplary embodiment, a pressure chamber is filled with a quantity of medium to be delivered. The pressure and volume of the medium to be injected to a guide may be determined when it is introduced into the chamber, or conversely the chamber may be designed to provide/apply pressure upon the medium within the chamber after its introduction. FIGS. 10A and 10B illustrates such a modulator 115 that comprises a compartment (medium chamber 116) defined for a medium to be injected, another compartment (gaseous chamber 118) for receiving a gaseous medium (e.g., air), and a deformable bladder 120 sealingly separating the compartments 116 and 118. As seen in the example, a valve 122 may be used to facilitate the flow of gas in and out of compartment 118 (e.g., to seal the gaseous compartment 118). The medium to be delivered can be introduced into the chamber 116 of the modulator 115 with the gaseous compartment valve 122 closed. During introduction of medium, the start of which is shown in FIG. 10A (fluid filling from the injector as indicated by flow arrow 62), the bladder 120 may deform into the gaseous compartment 118 until the medium obtains an intended pressure for the delivery of the medium to the guide catheter. Not shown in FIG. 10 are the valve mechanisms (such as those found on the manifold 38, for example, of FIG. 3C) to allow the passage of medium, and retention of medium within the modulator 115, until an injection to the guide is warranted. The medium may be released from the chamber 116 by opening, or otherwise activating, a valve (not shown) between the medium chamber 116 and the guide. FIG. 10B illustrates releasing of the medium from the chamber 116 to the guide catheter (as indicated by flow arrow 124).

Conversely, the chamber 116 of FIG. 10A might be filled with injection medium first; and, then pressurized to an intended delivery pressure by introduction of gas into the gaseous compartment 118, thus applying pressure to the medium through the bladder 120.

Although the previous description of device 115 may be illustrated as "sequential" delivery, device 115 may be designed to act as a "capacitor" during simultaneous delivery. In this case, there may be another port (a "To Guide" port configured on the medium chamber 116, not shown), to allow delivery from the device 115 during injection.

A modulator 115, such as example devices of FIGS. 10A and 10B, may advantageously provide a flow profile that resembles the injection $Q_{Improved}$ of FIG. 4C, at least as it pertains to areas A and C of FIG. 4B, since the injection may be delivered quickly to a $V_i$ flow rate, accommodating a quick ramp up and a fairly even flow rate for a short period of time. With respect to area B of FIG. 4B, chamber 116 of FIGS. 10A and 10B may decompress (while delivering flow) to a level that is below an "improved" working range. To compensate for this, a mechanism (such as a one-way value; e.g., valve 117 in FIG. 10B) may be disposed between the chamber and the guide to assure that the medium flow rate delivered meets the intended limits (e.g., minimal flow rate) for the injection, or terminates the flow.

Figure 11A:
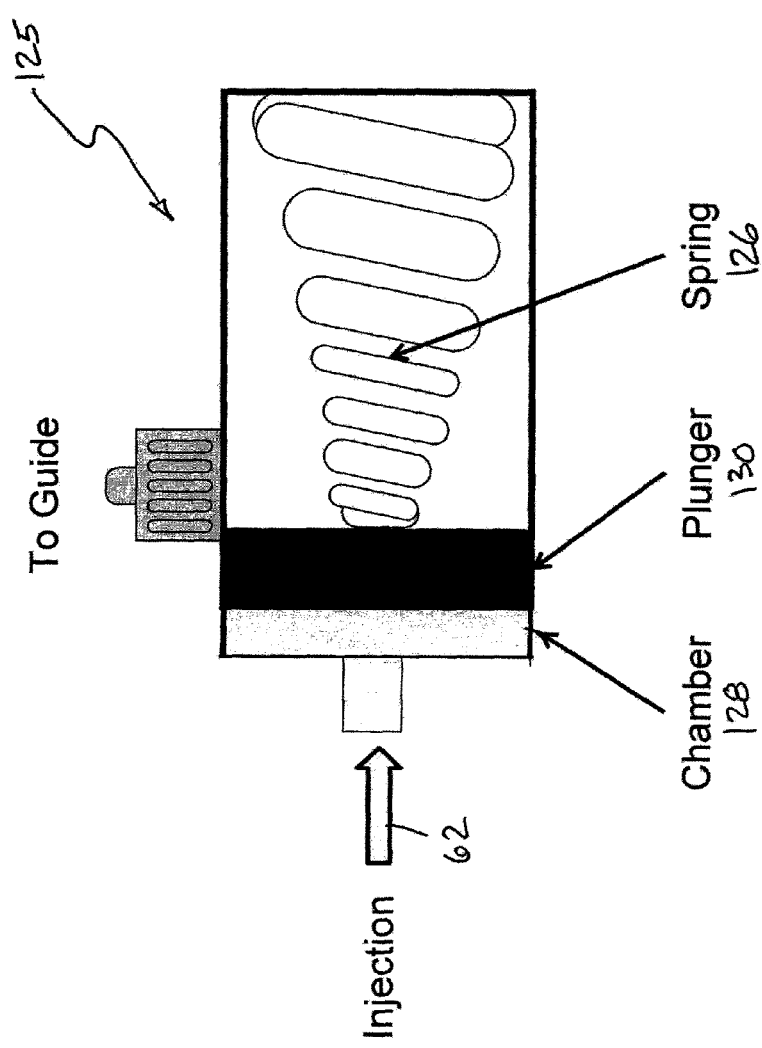
FIGS. 11B and 11B illustrate an exemplary flow modulator with constant force chamber, in different stages of flow control.
Figure 11B:
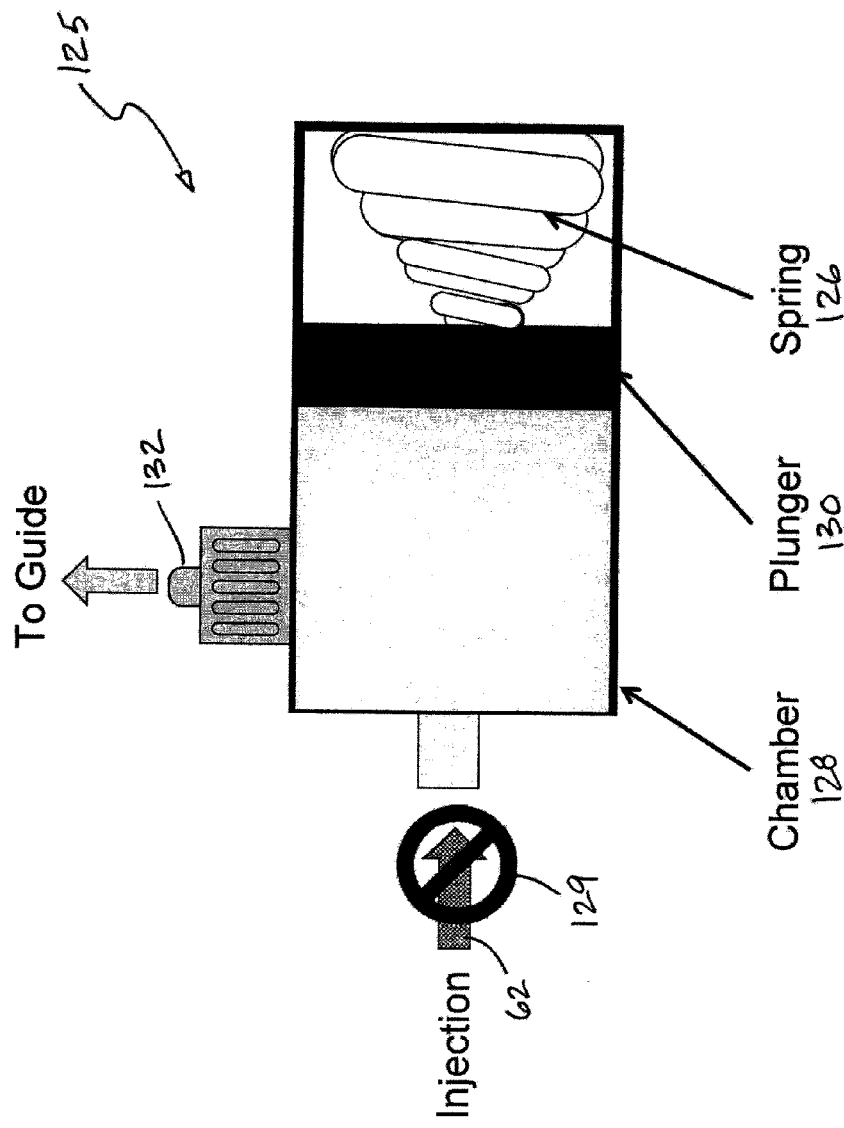

An alternative construction of a modulator may include a chamber constructed with a constant force spring, as shown in FIGS. 11A and 11B. Such a spring, by design, may deliver a constant force on a member (such as a plunger) over its working range (displacement). A modulator 125 of this type may include a conical spring (126 as shown in FIG. 11A) as an example of such a spring that can be made to have a constant force delivered over different compression lengths (displacements from equilibrium). The spring 126 may have variable pitches, with a larger pitch in its larger outer coils and a smaller pitch in its smaller inner coils, thus collapsing/expanding the coils at the same force during compression/decompression. Similar to the other devices described herein, the alteration of an injection's pressure and flow may be performed while delivering media to a delivery site, as well as performed by more than one step/sequence in delivery.

Using such a constant force injection modulator 125 as described, one might inject a quantity of medium into a chamber 128 of modulator 125 (as indicated by flow arrow 62), leading to compression of conical spring 126, as seen in FIG. 11B. Once a desired volume of medium has be received within chamber 128, injection may be stopped and/or back flow of medium from chamber 128 to the injector prevented (such as by manipulation of a valve—not shown), as further illustrated at 129 in FIG. 11B. Upon actuation, or otherwise release, of medium from the chamber 128 (such as opening of a valve to the guide—not shown) a plunger 130 may drive (as urged by compressed spring 126) the medium from the chamber 128 with constant pressure (and commensurate volume flow rate) toward the guide via an orifice in chamber 128 leading to the "To Guide" port 132. It might be advantageous with this modulating system 125 to allow "space" within the chamber 128 for the plunger 130 to close the "To Guide" orifice once a desired volume has been delivered.

An alternative construction (not shown) for the modulation system 125 of FIGS. 11A and 11B might also include mechanically driving a displacement/plunger element at a constant force within/upon a chamber so as to achieve a constant pressure upon the chamber and drive agent at a constant flow rate to the delivery catheter. Such a chamber might have a construction as shown in FIG. 11A. An alternative embodiment for simply providing constant force on a plunger in a chamber might include the placement of a weight upon a vertically-mounted plunger element within the chamber. For example, a syringe-type chamber might be vertically situated with the displacement actuator/element located above (further away from the center of the earth), and the outlet port located below (closer to the center of the earth). After filling the chamber with medium, various weights may be placed upon the displacement element so as to create the intended constant force upon the plunger (e.g., using gravity upon a mass in deriving a constant force). When an injection is needed, the medium may be released (or otherwise actuated to be released) from the chamber by opening a valve (such as a stopcock). The opening of the valve thus allows the medium to exit the chamber as a result of the force placed on the medium from the weight upon the plunger. The measure of the weight might be, for example, similar to the force determined for the constant force modulator 125 described above.

An alternative use of regulator 125 of FIG. 11 might be employing the regulator during the simultaneous injection and delivery of medium to/through the delivery catheter. With this application, injecting medium into chamber 128 with constant force spring 126 may provide a "pre-loaded" resistance to filling of the chamber. Once a pre-set level of pressure is achieved, regulator 125 may allow injectate to pass into chamber 128 and out of the chamber through the "To Guide" port 132. Additional filling of chamber 128 may take place during injection of medium if the injection pressure is greater than the pre-set spring resistance (and assuming sufficient resistance to delivery in the delivery catheter). In addition to filling, the chamber 128 may "discharge" medium (a reduction in volume) at a constant pressure (approximately the pre-set level of pressure) if/when the pressure from the injector is less than the pre-set resistance by constant force spring 126. With this exemplary simultaneous modulation, regulator 125 may act as a "capacitor" (i.e., having the ability to store and discharge a pressurized volume of medium) so as to "level-out" or "smooth-out" the pressure/flow profile of a medium directed to the catheter during injection.

Further to the description of modulator 125, and other media modulators described herein, manual injection (such as a syringe) during delivery media to an injection site might have varied pressures/flows passing to the modulator. Not only might the flows/pressures to the modulator be varied, but it is conceivable (depending on the system construction) that the flow of injection medium might, at times, return into the injector (syringe). As an example, it is possible that an administrator of a syringe might release the pressure placed upon the plunger. Depending on this reduced force, it is possible that the pressure/fluid stored into chamber 128 may be diverted back to the syringe—a function of the "least path of resistance" to the flow from the capacitance chamber 128.

Figure 21:
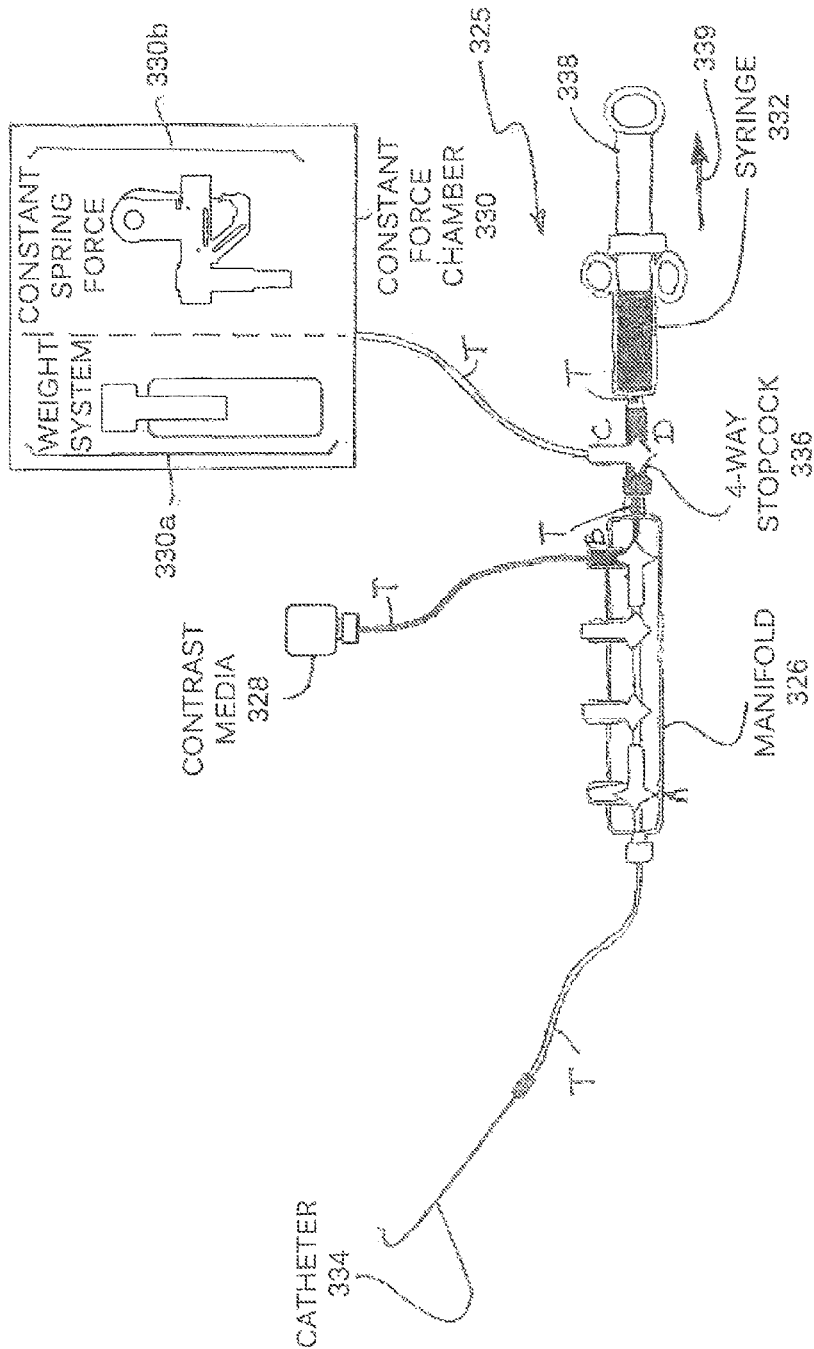
Figure 24A:
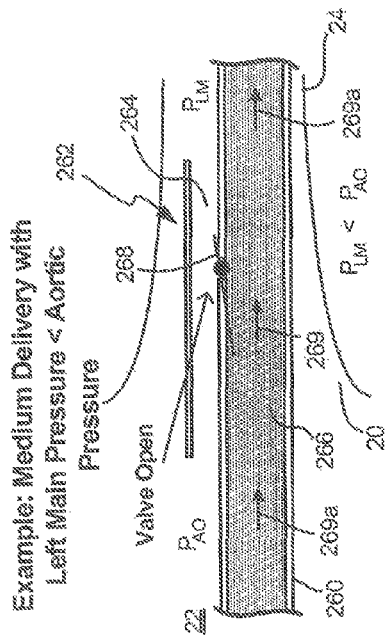
FIGS. 23, 24A and 24B illustrate an exemplary passive blood flow and medium flow valving mechanism operable as a function of a physical attribute in and/or around a medium delivery site.
Figure 24B:
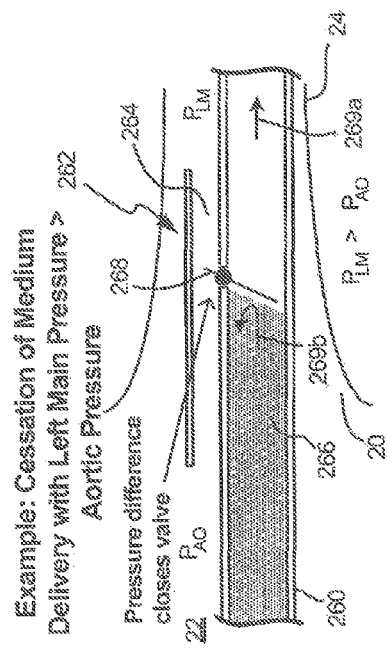
Figure 23:
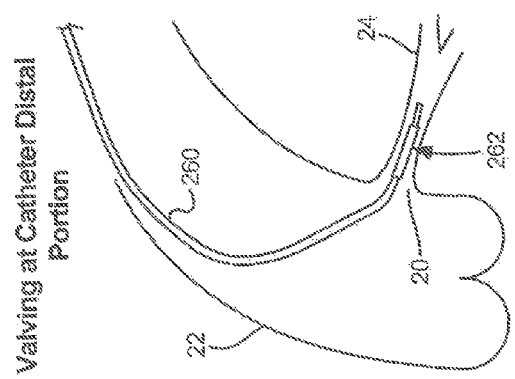

Advantageously, a modulator having a constant force chamber of such construction may be configured to improve a medium injection flow/pressure profile delivered to a delivery catheter. FIGS. 20 to 22 illustrate such an alternative system configuration/construction, and its method of use, which may provide an improved pressure/flow delivery profile. A modulator system 325 of FIG. 20 includes a manifold 326 having several elements attached to the manifold 326 to include: a reservoir or vial 328 of medium (i.e., contrast agent), a constant force chamber 330, an injector 332 (e.g., syringe), a delivery catheter 334, and a 4-way stopcock 336. These elements may be configured so as to be in fluid communication with one another, at times, via suitable tubular members T. Valves A (manifold to catheter), B (medium vial to manifold), C (constant force chamber to manifold), and D (injector to manifold) may allow for opening and closing such fluid communications between the manifold 326 and different elements of 328, 330 332, 334 and 336 of modulator 325. Note that 4-way stopcock 336 may provide the valving functions of valves C and D in lieu of separate valves/attachments. Of further note, the constant force chamber 330 may be configured, as illustrated, to accommodate a weighted force element (discussed previously) or a coiled constant force element, so as to deliver a constant force upon medium in a chamber therein with a displaceable plunger or surface. These are but two examples of how one might configure a constant force chamber and, as such, are to be illustrative but not limiting in the various configurations to construct a constant force apparatus.

In the exemplary method of performing an injection modulation, contrast agent from vial 328 is drawn into the syringe 332 by closing valve A (to prevent flow between the manifold 326 and the delivery catheter 334), opening valve B (to permit flow between the medium vial and the manifold 326), closing valve C (to prevent flow between from the constant force chamber 330 and the manifold 326), and opening valve D (to permit flow between the manifold 326 and the syringe 332), as represented in FIG. 21. The syringe 332 may be filled with injectate medium by drawing on a plunger 338 of the syringe 332, as represented in FIG. 21 by arrow 339, to thus draw medium from vial 328 into syringe 332. Valve B (between medium vial 328 and manifold 326) may be closed when sufficient medium has been drawn into syringe 332.

Whether a construction having a weighted force element acting upon a plunger (such as illustrated by weight system 330*a*), a construction employing a constant force spring acting on a plunger (such as illustrated by constant spring force 330*b*), or an alternative constant force contrivance, a load is determined to be deployed upon the constant force chamber 330 (and its fluid contents) sufficient in regulating medium flow to be delivered by the delivery catheter 334. For the sake of elucidation only, say a pressure of 50 psi is wanted at the manifold 326 (e.g., into the proximal port of the delivery catheter 334) to create an improved medium delivery flow through the catheter 334. Constant force chamber 330 may be configured so as to generate approximately 50 psi upon a fluid within, entering, or exiting, the constant force chamber 330 when valve C is opened (i.e., open to permit flow from constant force chamber 330 into the modular system 325).

When an injection of medium to an injection site is warranted, valves A (to catheter 334), C (to chamber 330) and D (to syringe 332) may be opened and the plunger 338 of the syringe 332 depressed (in direction of arrow 340 in FIG. 22). As the plunger 338 of the syringe 332 is quickly depressed, the fluid ejected from the syringe 332 will want to travel towards the least path of resistance, simultaneously driving fluid to the catheter 334 (as represented in FIG. 22 by medium flow arrows 342) while passing into the constant force chamber 330. Rapid introduction of medium by the syringe 332 will allow the pressure within the manifold apparatus to quickly obtain 50 psi, and allow for filling the constant chamber force 330 with medium (via flow of arrow 344) when pressure is greater than 50 psi. Thus, constant force chamber 330 acts as a capacitor as it takes on more medium at, or above, a pressure of approximately 50 psi; while, also allowing the delivery of medium to the catheter 334 at approximately 50 psi (via flow arrows 342). In essence, the flow delivery profile of the modulator 325 may reduce the "wasted" contrast due to ramping-up pressure/flow (area A of FIG. 4B); as well as, reduce the "wasted" contrast from over-injecting into the delivery catheter (area C of FIG. 4B) by maintaining a more constant pressure within the manifold.

In the example shown in FIGS. 20 to 22, once the operator has filled the constant force chamber 330 with contrast medium to some degree, the constant force chamber 330 may continue to discharge the wanted 50 psi to the delivery catheter 334 even if the injection flow is diminished, thus facilitating a "smooth" injection to the delivery catheter 334.

When it is determined that sufficient medium has been delivered by the syringe 332, releasing the plunger 338 (e.g., allowing the plunger 338 on the syringe 332 to negatively displace with no loading) may allow a rapid drop-off of pressure from the manifold 326 as the pressure within the constant force chamber 330 may be dissipated by discharging flow away from the delivery catheter 334 and into the syringe 332 (e.g., least path of resistance—represented by the phantom arrows 346 in FIG. 22). Thus, the rapid decrease in pressure delivered to the delivery catheter 334 may act to reduce the "wasted" contrast as typically seen at the tail end of an injection (e.g., area B of FIG. 4B). It is also possible to facilitate the rapid termination of the injection by closing valve A (manifold to catheter) before, during, or quickly after an injection is terminated by the syringe 332. The termination of the medium injection also may be enhanced by including other mechanisms (such as a one-way valve) so as to quickly shut-off delivery to the catheter 334 when there is insufficient pressure (e.g., when a selected low pressure threshold is reached). Such a one-way valve could be placed at various locations within the modulator system 325, including its residing between the manifold 326 and the delivery catheter 334, along the tubular connector therebetween, such as illustrated by valve 317 in FIG. 22.

Depending upon the circumstances, it may be desired to change, from procedure to procedure (or even during a single procedure), the load provided by the constant force chamber 330. When the constant force chamber 330 is configured to accommodate a weighted force element (such as weight system 330*a*), this may be accomplished by changing the amount of weight being applied to the plunger. When the constant force chamber is configured as a coiled constant force element (such as illustrated by constant spring force 330b), the load may be modified by changing the coiled constant spring element. However, these approaches may be cumbersome and require a stockpile of alternate components (e.g., sets of weights or springs) to achieve varied loads. A constant force element that may be varied (e.g., the ability to change the constant force delivered) with a platform capable of varying the constant force, such as 402, may be of value.

Figure 26:
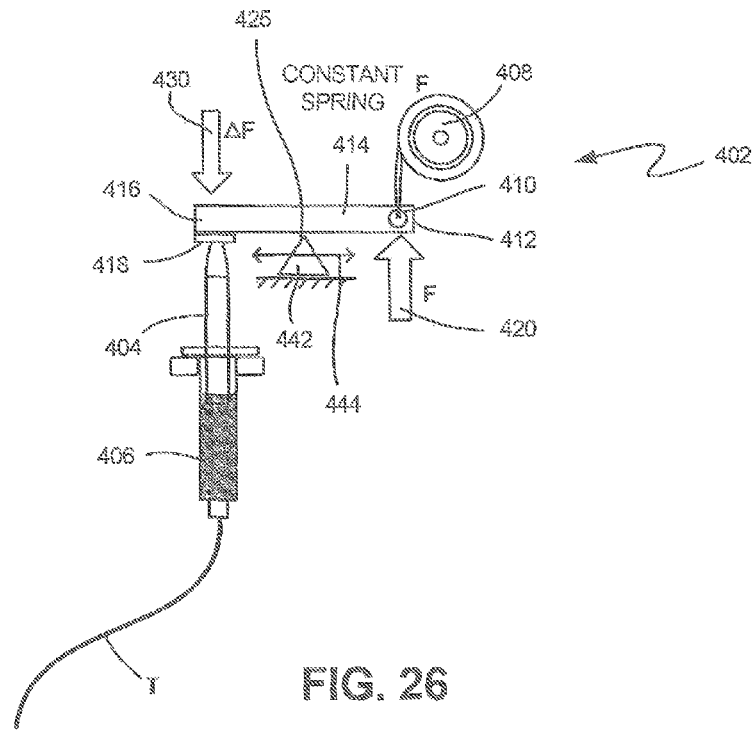
FIG. 26 illustrates an exemplary variable force delivery platform for use in a modulator system.

As illustrated in FIG. 26, a variable force delivery platform 402 for use in a modulation system such as modulation system 325 is provided to act upon a plunger 404 which in turn presents a load to the medium via a force surface within a plunger chamber 406 filled with medium. The chamber 406 thus may act as the pressure chamber within the constant force chamber 330 (such as illustrated in FIG. 22) that may be connected by tubular member T to valve C on stopcock 336.

The platform 402 may include a constant force spring 408, such as the coiled constant spring element illustrated in FIG. 26, which is operably connected at a free end 410 of the spring 408 to a first end 412 of a pivotable lever 414. A portion of the lever 414, adjacent a second end 416 thereof, may be operably engaged with a free end 418 of the plunger 404. The spring 408 may be coupled to the lever 414 so as to provide a constant spring force, such as illustrated by force arrow 420, upon the lever 414 adjacent its first end 412.

The lever 414 may be pivotally coupled to a housing or other support structure as at pivot point 425 in FIG. 26. Thus, the lever 414 may pivot about point 425 due to the application of force 420 adjacent its first end 412 and a corresponding, yet opposite, force 430 being imparted adjacent the second end 416 of the lever 414. The force 430 may be applied via the lever 414 and plunger 404 to the medium in the chamber 406, and is defined by the spring force of the spring 408 as it is transferred via the lever 414 to the plunger 404. The force transfer is dependent upon the pivoting of the lever 414 about its pivot point 425.

The amount of constant force thus applied to the medium in the chamber 406 can be modified by changing the position of the pivot point 425 relative to the lever 414. In other words, by moving the pivot point 425 toward or away from the spring 408, the effective pivotable length of the lever 414 between the spring 408 and pivot point 425 is changed. The amount of force 420 applied to the lever adjacent its first end 412 does not change, but movement of the pivot point 425 will alter the amount of force 430 applied at the second end 416 of the lever 414.

This lever and pivot point arrangement is schematically illustrated in FIG. 26 as a fulcrum 442, which as illustrated, is mounted on suitable supporting structure of the constant force chamber 330. Leaving all other things equal, movement of the fulcrum 442 and its associated pivot point (e.g., from left to right and vice versa, as seen in FIG. 26) will change the force 430 relative to the plunger 404. This optional directional movement of the fulcrum 442 is illustrated by arrow 444 in FIG. 26. When the fulcrum 442 is moved toward the first end 412 of the lever 414, the effective lever arm distance between the spring 408 and the pivot point 425 is shortened, thus lowering the force 430 applied to the plunger 404. Alternatively, when the fulcrum 442 is moved away from the spring 408 (and toward the second end 416 of the lever 414), the effective lever arm distance between the spring 408 and pivot point 425 is lengthened, resulting in a greater force 430 applied to the plunger 404. Accordingly, the constant force applied to the medium in the chamber 406 can be changed simply by changing the location of the pivot point 425 relative to the length of the lever 414, and in this example, that is accomplished by movement of the fulcrum 442 along its possible travel movement trail represented by arrow 444. Advantageously, this may allow for incremental adjustment of the constant force applied to the medium in the chamber 406.

Figure 27:
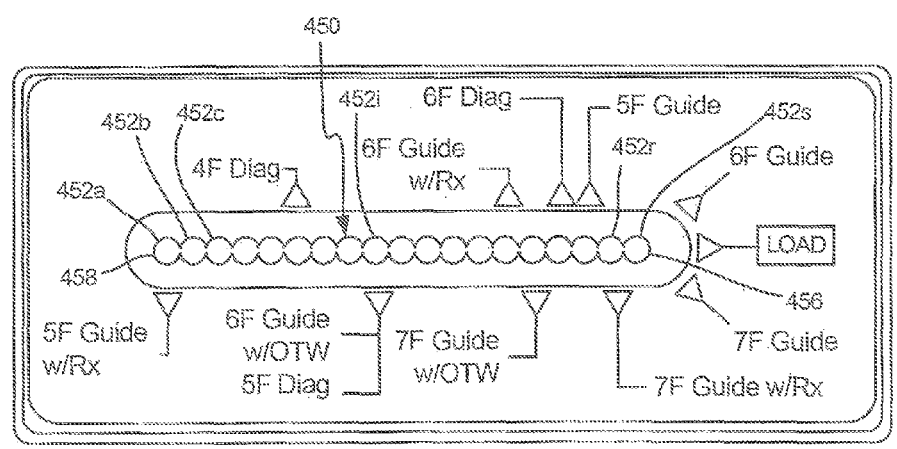
FIG. 27 illustrates a force pin selection guide for use in connection with a variable force delivery platform.
Figure 28:
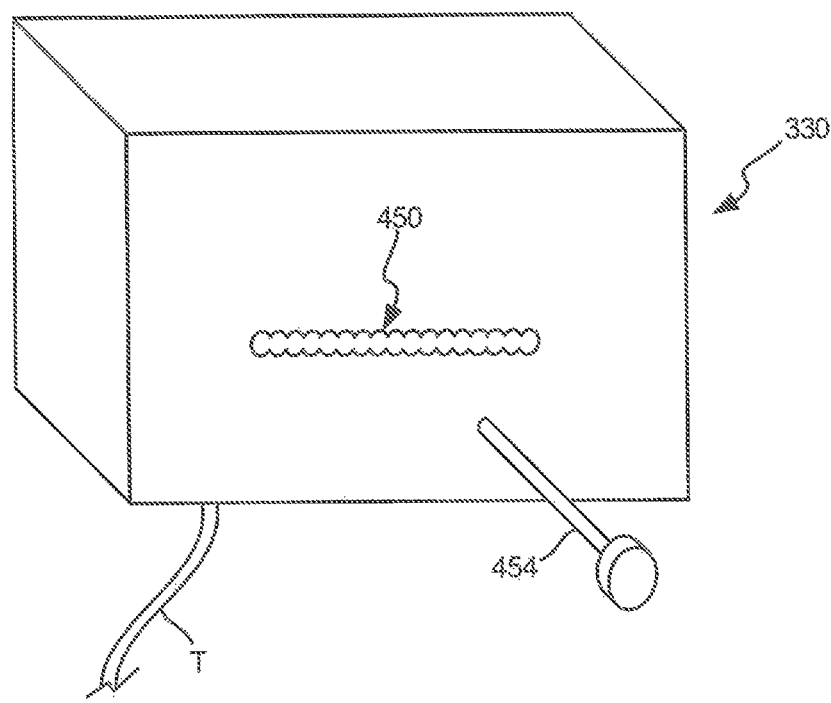
FIG. 28 illustrates an exemplary pin and its associated pin location slot, as used with a variable force delivery platform.

In one example, the position of the fulcrum 442 is determined by placement of a "pin" along a "pin slot" having a discrete number of pin locations. Each pin location relative to the pivoting lever 414 thereby defines the fulcrum 442 position, which in turn defines a pre-established load to be placed on the medium in the medium chamber 406 depending upon the force of the constant force spring 408. An exemplary pin location slot 450 is illustrated at FIGS. 27 and 28. The slot 450 may be further defined by a connected line of circular pin receiving holes 452 (illustrated in FIG. 27 as "pin receiving holes" 452a to 452s, as viewed from left to right). The desired constant force is selected by inserting a pin (such as shown as pin 454 in FIG. 28) into a selected pin receiving hole 452 of the slot 450. The amount of force that will be applied to the plunger 404 may be determined by which pin receiving hole is selected. Selecting a pin receiving hole adjacent a first end 456 of the slot 450 will result in less force being applied to the plunger 404, while selecting a pin receiving hole at a second end 458 of the slot 450 will result in a greater force being applied to the plunger 404. By way of example, in a left main coronary artery setting, for effective medium modulation, less force will be required when a larger guide catheter is deployed. For a six French or a seven French guide catheter, placing the pin 454 in the pin receiving hole 452s may provide sufficient constant force on the medium in chamber 406 to deliver a medium at a desired rate. However, when a seven French guide catheter is used with a treatment ("Rx") catheter, more constant force may be required to deliver a medium, and thus the most appropriate location for the pin 454 is in pin hole 452r. In a further example, if a five French catheter is being deployed which includes a "Rx" catheter, the pin 454 may be placed in pin hole 452a to provide a greater constant force for the medium being supplied by the constant force chamber 330 into the modulator system 325.

Other exemplary constant force "pin" settings for use with different catheter configurations may be seen in FIG. 27. The settings shown are exemplary of a situation wherein one might expect approximately 2 ml/sec of medium delivered with a constant force chamber 330 of approximately 50 psi, as an example. In the context of the example of FIG. 27, these terms may generally mean as follows: "Guide" means a coronary guide catheter, "Diag." means a coronary diagnostic catheter, "Rx" means a coronary treatment catheter, and "OTW" means an over-the-wire coronary treatment catheter.

An exemplary constant force chamber 330 having the slot 450 and its associated pin 454 for manipulating the fulcrum 442, and its associated pivot point 425, is illustrated in FIG. 28. Other arrangements for moving the fulcrum 442 along or about lever 414 and defining their relative positions are also contemplated, such as rack and pinion movement, magnetic couplings, and other like contrivances that may provide the ability to vary a constant force delivered to a pressure chamber 406 thru plunger 404.

Figure 29:
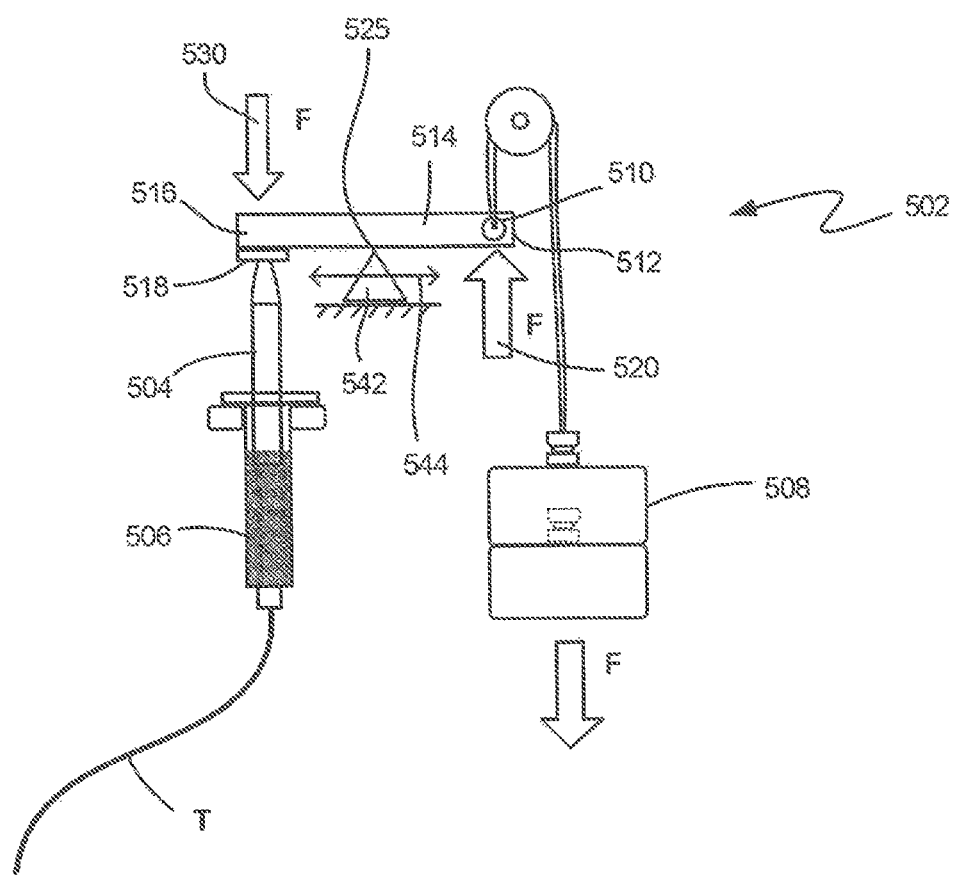
FIG. 29 illustrates an alternative exemplary variable force delivery platform for use in a modulator system.

FIG. 29 illustrates an alternate variable force delivery platform 502, where instead of a constant spring 408, a weight system 508 is employed to define a constant force such as illustrated by force arrow 520. The force from the weight system 508 is transferred to the lever 514 at 510 by suitable means, such as a cable and pulley arrangement as shown. Other than the source of the constant force being a weight system instead of a constant spring, the platform 502 operates in a similar matter to the platform 402 described above. Like elements and features are shown in FIG. 29, indexed upwardly by 100 using reference numerals similar to those illustrated in FIG. 26.

Figure 12A:
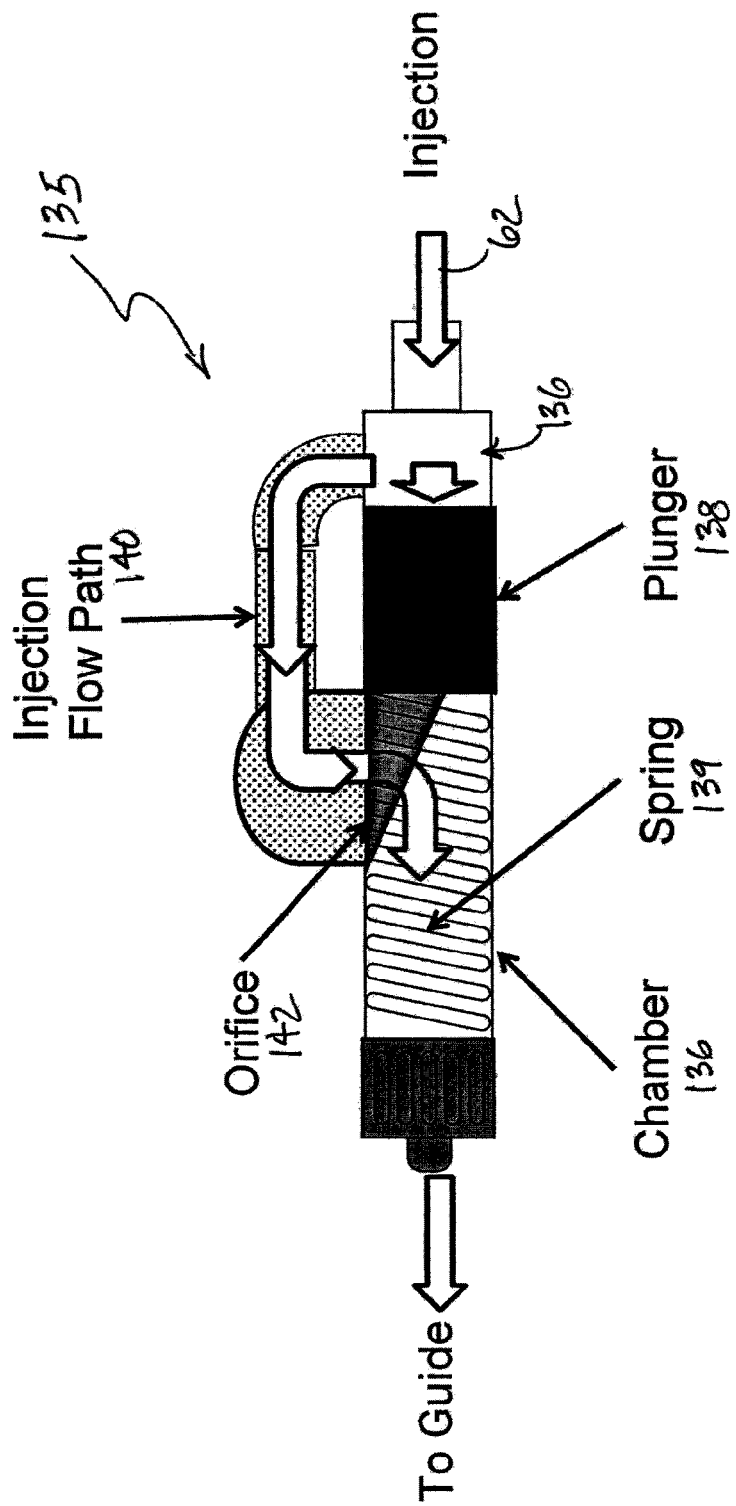
FIGS. 12A and 12B illustrate an exemplary constant flow modulator, in different stages of flow control.
Figure 12B:
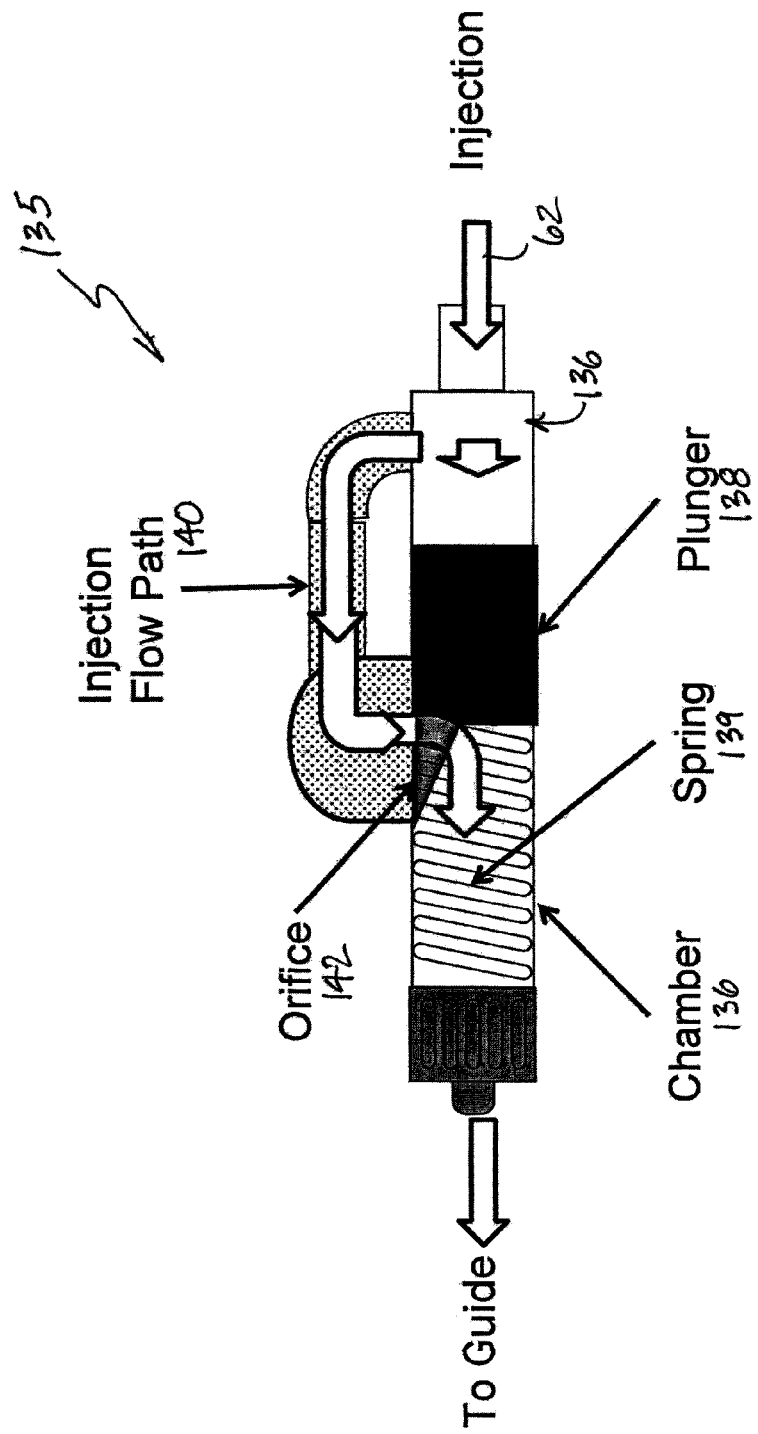

An alternative embodiment in the modulation of flow through a device to control injections may be found in FIGS. 12A and 12B, which illustrate a constant flow rate modulator 135 that may advantageously modulate the flow rate delivered to the guide (or any other delivery device), versus the constant force of modulator system 325. A modulator such as this might be useful for delivering a constant flow rate of a medium to a target site, independent of using different conduit configurations. For example, the resistance to flow of a medium through an angiographic catheter (for diagnostic visualization of an artery) may be different than the treatment system described previously. And, as such, the pressure required to drive constant agent flow through an angiographic catheter typically may be lower than the pressure necessary to drive similar agent flow through the treatment system. Advantageously, a physician may be able to perform an angiographic assessment (with an angiographic catheter) of an artery, as well as a treatment (with a treatment system) with the same modulator delivering similar constant flows of agent. An arrangement as shown in FIGS. 12A and 12B may allow a physician to switch between both agent delivery systems with the same modulator 135. This is in comparison to say, the constant force of modulator system 325, wherein the weight, the constant force coil, or the constant force contrivance may require adjustment of the force to accommodate different system considerations (e.g., guide catheter, treatment catheter, etc.).

Referring to FIG. 12A, the injection device provides an injection (see flow arrow 62) into a chamber 136 of the modulator 135. The injection acts upon plunger 138 (that is sealably and movably disposed within chamber 136, and biased in opposition to initial injection medium pressure by variable force spring 139) with a force derived from the pressure of the medium over the area of the plunger 138. The flow of medium is directed out of chamber 136 along an injection flow path 140, by-passing the plunger 138, and then re-establishing flow within the chamber 136, via an orifice 142, on the guide side of the plunger 138. Depending on the pressure that the medium experiences on the guide side of the modulator 135, the spring-engaged plunger 138 will be driven (by the force of that pressure) to a location along the orifice 142 passing through the wall of the chamber 136. The placement of the plunger 138 (and its associated spring 139, and the bias force of spring 139) and its relationship to the orifice 142 may partially restrict the flow of the medium into the guide portion (i.e., guide catheter side) of the chamber 136. As an example, the orifice is held completely open in the drawing of FIG. 12A, suggesting the pressure of the injection may be nearly the pressure in the guide portion of the chamber 136, with the modulator "opening the flow" of the orifice 142 as much as possible to allow greater flow. The differential of pressure, and thus the forces acting upon both sides of the plunger may be nearly the same in FIG. 12A. An example of this scenario may be when there is relatively high resistance to medium flow in the delivery guide (e.g., when in use with a treatment system).

Conversely, FIG. 12B shows the orifice 142 partially occluding the flow from the injection flow path 140 into the guide portion of the chamber 136. In this case, there may be less resistance (i.e., medium flows more readily) from the guide or delivery catheter and the differential in pressures within the two sides of the chamber 136 have increased. In other words, the injection path has been restricted (driven by the pressure differentials) to drive the fluid in a delivery catheter having less resistance (and, therefore requiring less pressure) in delivering an equivalent flow rate (such as when in use with an angiographic catheter). In both cases presented, the flow rate of medium to/though the delivery catheter may be the same; however, it is the modulator that may be configured to adapt/change resistance to flow in order to accommodate constant flows (delivery of medium with different systemic resistances).

The example of the flow modulator of FIGS. 12A and 12B illustrates a chamber with a single, graduated orifice in performing the constant flow rate modulation function. However, such a function could be performed with a multitude of orifices, as well as with different cross-sectional areas of the orifice(s) to accomplish the same intended function. In addition, other forms of variable pressure restrictors (having constant flow rate modulation) may accomplish the intended function. As such, these alternatives are considered within the scope of the disclosed devices and processes.

It should be also noted that the exemplary descriptions have assumed that the ancillary tubings/connections/channels within and/or between system components/devices, are relatively large and may have negligible "resistive" impact on the overall flows/pressures modulated by the devices. For example, the pressure drop created by the lumen of the channel between chambers 1 and 2 of FIGS. 9A-9C, or within the connective tubings and/or connectors of FIGS. 6A-6C should be minimal. If not, design changes could be made to accommodate for the additional resistances created with such connections without deviating from the scope of the disclosed devices and processes.

Although the various constructions of modulating devices have been described as having chambers with springs therein, it is clear that any passive and/or active biasing or valving mechanisms (or any combination thereof) might also be used to produce similar functions, including apparatuses being significantly smaller than the devices illustrated. For example, hydraulic valves, release valves, one-way valves may perform functions so as to activate or otherwise modulate flow (i.e., allow flow) upon a known/determined flow rate and/or pressure, as well as deactivate (stop or limit flow) once a known/determined flow rate and/or pressure condition has been obtained. Furthermore, passive devices such as fluid flow restrictions (i.e., tubular members) and/or diffusers may also be utilized in modulating the flow. These restrictive devices may not necessarily define an "on-off" (e.g., digitally "there is" or "there isn't" flow based on pressure) restriction, but rather act to affect the flow rate in the catheter based on restrictions to flow in the total system. It is within the scope of the devices and methods described herein to include such alternative devices, or devices in combination, to produce similar injection modulation effects.

Figure 51A:
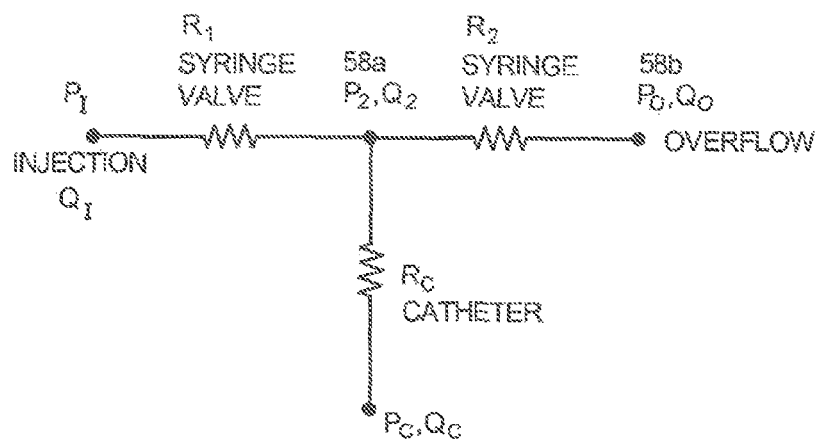
FIGS. 51A, 51B and 51C schematically illustrate alternate flow diversion configurations for agent flow from an injector through a catheter system.

As an example of passive devices that may alter, or modify, the flow of fluid delivered through a catheter, a review of the resistance to flow of the embodiment in FIG. 6 may be seen in FIG. 51A (noting that $Q=\Delta P/R$; where $Q$=fluid flow through a system, $\Delta P$=pressure differential across the systems and $R$=Resistance to fluid flow in the system; see e.g., FIG. 7). In the example shown in FIG. 51A, an injection from a syringe passes into a chamber 64 with pressure $P_I$ and flow $Q_I$. There is initially resistance to flow ($R_1$ of the modulator device 55 "valve") in the chamber 64 from the spring constant $k_1$ of the spring 68. Once the resistance is overcome (say, for example, by injecting over 30 psi), flow is allowed to pass to the catheter through orifice 58a ("To Guide"), at a pressure of $P_2$ and flow of $Q_2$. This pressure/flow might be considered a minimum threshold of delivering flow to the catheter system. Upon increased pressurization from the injection (e.g., from $P_I$), additional resistance $R_2$ to flow will be created by the spring 68 in the modulator device 55 (in addition to the resistance $R_c$ of the catheter/system). Once resistance $R_2$ is overcome through increased pressurization/flow (say, for example, 50 psi), fluid flow will be allowed to flow out of the "overflow" orifice 58b (see, e.g., FIG. 6B) at a pressure of $P_o$ and flow of $Q_o$. This might be considered a maximum threshold of pressure at which the medium may be injected into the guide (e.g., any pressurization above this will result in bleeding or diverting medium out of the system). It should be noted that when the pressure at $P_2$, for example, is high enough to allow flow (e.g., minimum threshold) to the guide, but less than the amount of pressure to overcome $R_2$ (e.g., maximum threshold), the flow of fluid to guide (and out of the catheter) will vary as a result of the pressure. As well as, when the pressurization exceeds the pressure at which the resistance of $R_2$ has been overcome, overflow $Q_o$ from the system will continue to increase with pressurization. As shown in FIG. 51A, the flow exits the catheter system at a pressure $P_e$ and a flow of $Q_e$.

Figure 51B:
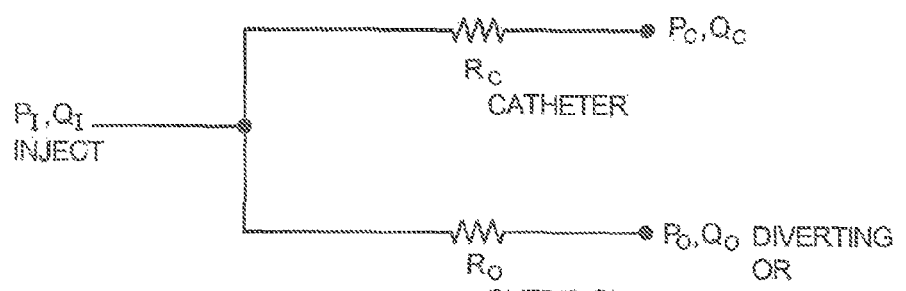

Looking at FIG. 51A, it is possible to alter the flow delivered to the catheter (or guide) system without using the resistance of $R_1$ (derived from the valve from the modulator device 55). The flow diagram of this example may be seen in FIG. 51B, wherein the pressure ($P_I$) and flow ($Q_I$) may be directly delivered to the catheter and an overflow path, in parallel. In this example, $Q_I$ may be split (based on different resistances between the two parallel pathways depending on the amount of flow one might want to direct to the catheter system. As an example, if a flow rate of 3 ml/sec were the maximum one wanted to deliver to the catheter, and the catheter system had a resistance of $R_C$ and possible maximum pressure and flow of (i.e., depending on the syringe, individual strength of the operator, convenience, etc.) $P_I$ of about 60 psi and $Q_I$ of about 5 ml/sec, one could design the constant resistance $R_O$ of the overflow, or diverting, fluid pathway (e.g., tubular member) to allow 3 ml/sec delivered to the guide at about 60 psi $P_I$. This embodiment allows for a simple solution for diverting flow, while modifying the delivered medium, so as not to exceed some approximate injection threshold amount that results in excess contrast being delivered. It should be noted in this configuration that there would be a constant "bleeding" off of the injection, irrespective of the injection pressure. Moreover, it is also possible the resistance of the "overflow" ($R_O$) may be created by alternative constructs, such as: resistance as a result of a tubular diameter or length dimension; resistance created by flowing through a restrictor, resistor, diffuser, filter medium, etc.; resistance created by alteration in the normal fluid path (pinching of the line in a discrete fashion); resistance created by a combination of any, or all, of the above (for example). To this end, overflow resistance $R_O$ of the above example could simply be a "tube" having sufficient resistance (e.g., diameter/length), or the placement of a resistance, such as a narrowing in a tube (e.g., pinching) to establish sufficient resistance.

Figure 51C:
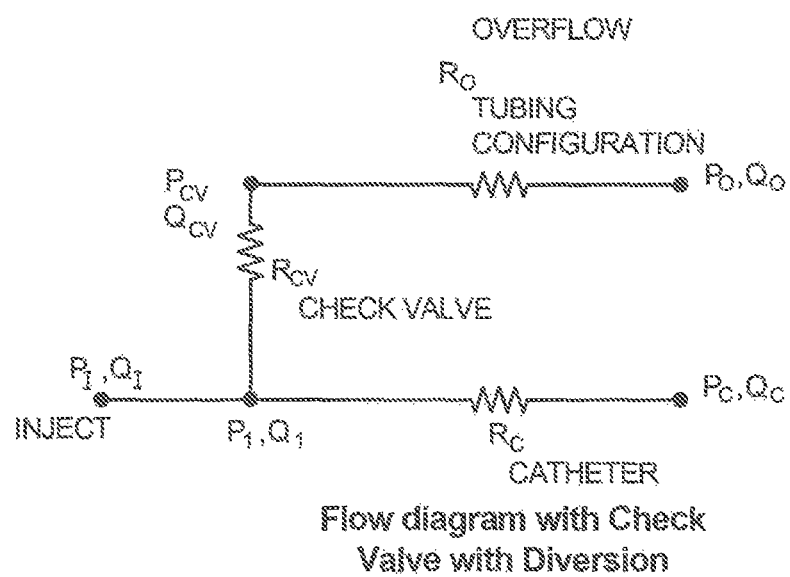

An alternative embodiment of diverting flow can be seen in FIG. 51C. FIG. 51C illustrates a flow pattern wherein the initial flow of $Q_I$ is directly injected to the catheter system, and upon reaching a minimum pressure (e.g., a pressure $P_1$ and associated flow rate $Q_1$), a "check valve" may be employed to start diverting the fluid away from the catheter system. In this case, the check valve resistance ($R_{CV}$) is in addition to, and prior, to the arrangement illustrated in the overflow tubing resistance ($R_O$). In FIG. 51C, the fluid pressure and flow rate exiting the check valve are represented as $P_{CV}$ and $Q_{CV}$. One advantage of this configuration (versus the arrangement illustrated in FIG. 51B) is that this configuration may allow less fluid to be discharged, since it diverts at a higher pressure point. FIG. 30 shows an exemplary device capable of producing the fluid flows as described.

As has been described, one means for producing an operative medium flow rate is to "strip off," "bleed off," or otherwise divert some of the medium flow coming from the syringe away from the catheter system. FIGS. 30 and 31 illustrate one exemplary arrangement for doing so. In this arrangement, syringe 332 may be fluidly coupled to medium reservoir 328 by suitable tubular members $T_1$, $T_2$ and $T_3$, and via manifold 326. For use, syringe 332 may be loaded with medium from medium reservoir 328 and then valve B on manifold 326 is manipulated to prohibit the flow of medium back to reservoir 328 via tubular member $T_1$.

A flow diverter assembly 550 may be positioned in the medium flow path between the syringe 332 and the catheter 334. As can be seen in FIG. 30 the flow diverter assembly 550 may be coupled to a four way stopcock 552 allowing the assembly 550 to be selectively active or inactive in the flow of the medium, if desired. For example, when the syringe 332 is being loaded with medium from the medium reservoir 328, the stopcock 552 may be positioned to permit medium flow between tubular members $T_2$ and $T_3$, but not to tubular member $T_4$ (disposed between the stopcock 552 and the flow diverter assembly 550). When the stopcock 552 is positioned to allow flow into tubular member $T_4$, medium flow may pass into the flow diverter assembly 550 upon pressurization from the syringe 332. Like the exemplary agent flow schematic in FIG. 51C, the flow diverter assembly 550 includes a check valve 554 aligned to prevent the flow of medium into the flow diverter assembly 550 until a certain medium pressure threshold is reached (e.g., 20 psi). Once the threshold pressured is exceeded, the check valve 554 may permit fluid flow into the flow diverter assembly 550. After traversing check valve 554, medium flow may pass distally therefrom via tubular member $T_5$ to a medium reservoir, which may be reservoir 328, as shown. When the pressure of the medium reaching the check valve 554 from the syringe 332 is lower than the threshold pressure, the check valve 554 seats itself so as to prevent back flow (i.e., medium flow out of the flow diverter assembly 550 via tubular member $T_4$).

In one embodiment, the flow diverter assembly 550, upon reaching a threshold pressure, may divert approximately 40% of the medium flow from the syringe 332, thereby allowing 60% of that flow to reach the catheter 334. For example, upon reaching a threshold pressure delivered to check valve 554 of flow diverter assembly 550 from syringe 332, the flow rate delivered from the syringe 332 could be 5 ml/sec.; however, the desired flow rate to the catheter 334 at this pressure may be 3 ml/second. In this case, flow diverter assembly 550 may be designed (i.e., length, diameter, configuration or other restrictive type structures) so as to allow a medium flow rate of 2 ml/sec. to "bleed off" (or, otherwise be diverted through tube $T_5$) from the total amount of medium delivered to the catheter 334. In one regard, this flow diversion arrangement can be considered to form flow resistors disposed in parallel, with one form of resistor being the catheter 334 itself, and the other form of resistor being the flow diverter assembly 550 (see again, e.g., FIG. 51C.). It should be noted that a change in the "catheter resistance" (e.g., change in the delivery catheter system) may require changing the resistances imposed by flow diverter assembly 550 to achieve similar diversion of flow (e.g., 2 ml/second).

In one embodiment, the flow diverter assembly 550 may include a mechanism that allows for selection and changing of a level of flow resistance and/or variation in the amount of medium flow allowed through the flow diverter assembly 550. Advantageously, a variable flow diverter assembly 550 which is capable of changing resistance may allow a user to switch medium delivery systems (i.e., a diagnostic catheter to a guide catheter with a treatment device) without having to change-out or replace the flow diverter assembly 550. In an exemplary embodiment, changing the level of flow resistance of the fluid medium through the flow diverter assembly 550 comprises changing an effective size of at least a portion of the fluid medium flow path through the flow diverter assembly 550. In simplified form, FIG. 31 illustrates a switch plate 560 that is movable between three positions relative to a base 562 of the flow diverter assembly 550 to allow for manual selection of a level of flow resistance of the fluid medium through the flow diverter assembly 550 to provide greater medium fluid flow resistance with higher pressure of injection. The switch plate 560 has an elongated opening 563 therein that may be sized to receive flexible and deformable tubular member $T_5$ therethrough. As illustrated in FIG. 31, the opening 563 may be larger in a first area 564, with a diminished dimension in at least one other direction 565 in a second area 566, and with a further diminished dimension in at least one other direction 567 in a third area 568. The tubular member $T_5$ extending out of the flow diverter assembly 550 and toward the reservoir 328 may extend through opening 563 on the switch plate 560. The switch plate 560 may be movable relative to the base 562 in direction of arrows 570. Switch plate 560 essentially acts as a sliding pinch valve relative to tubular member $T_5$. Accordingly, when the switch plate 560 is aligned with the tubular member $T_5$ in the first area 564 of the opening 563, the greatest amount of flow may be allowed through tubular member $T_5$ by the flow diverter assembly 550 (or, conversely, the least amount of flow to the catheter 334). In one embodiment, this may provide a bleed off of medium flow rate suitable for use with a 6 French guide catheter (or equivalent flow restrictive structure). When the switch plate 560 is moved to align tubular member $T_5$ within the second area 566 of the opening 563, the tubular member $T_5$ may be pinched (or otherwise restricted in cross-section), thereby restricting the amount of medium that may flow therethrough, and back to the reservoir 328 (i.e., the flow in $T_5$ may be more restricted in this configuration than when the tubular member $T_5$ is aligned within the first area 564 of the opening 563). In one embodiment, this may provide a bleed off of medium flow rate suitable for use with a 6 French guide catheter with a coronary treatment catheter therein, or with a 5 French coronary diagnostic catheter, wherein a greater amount of flow may be directed toward the catheter 334. When the switch plate 560 is moved to align tubular member $T_5$ within the third area 568 of the opening 563, tubular member $T_5$ may be further pinched or restricted in cross-section, thereby allowing even less flow of medium therethrough (e.g., through tubular member $T_5$) than either of the previous two positions of the switch plate 560. In one embodiment, this may provide a bleed off of medium flow rate suitable for use with a 4 French diagnostic catheter.

The flow diverter assembly 550 need not include merely discrete alternate variable flow settings via a mechanism such as movable switch plate 560. Instead, the flow diverter assembly 550 could have a mechanism or design that allows variable flow settings including two, three (as shown in FIG. 31) or more selected flow rates for flow diversion from the syringe 332 to the reservoir 328. In one embodiment, flow diverter assembly 550, tubular member $T_4$ and stopcock 552 are configured as one self-contained component (such as illustrated by component 572 in FIG. 30) that can simply be inserted into the medium flow path between the syringe 332 and the catheter 334.

Another means for achieving restriction of the driving medium flow rate from the syringe 332 is to dispose a flow restrictor in line somewhere between the syringe 332 and the catheter 334. Such a flow restrictor would take the form of, for example, a tubular member constrained in size to restrict flow therethrough, a flexible tubular member pinching mechanism, or a check valve.

Figure 32:
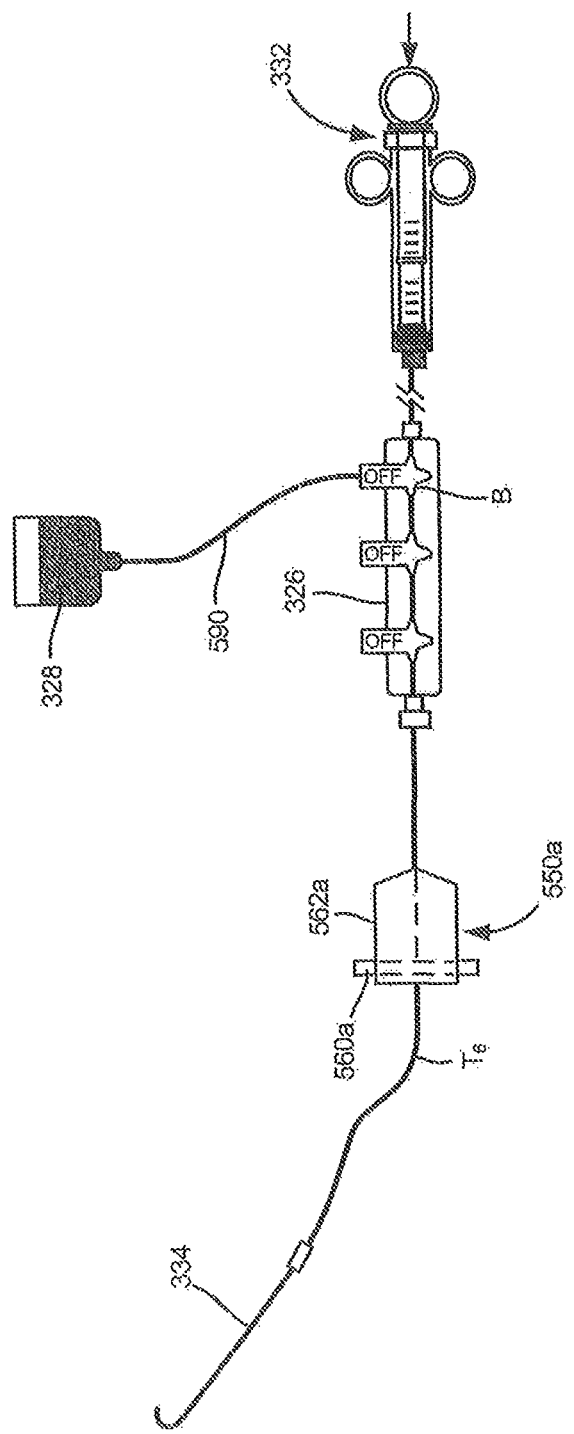
FIG. 32 illustrates an exemplary flow restrictor assembly.

One in-line flow restrictor arrangement is illustrated, for example, in FIG. 32. In this embodiment, flow restrictor assembly 550a is disposed distally of the manifold 326 and may be similar in configuration to flow diverter assembly 550 of FIG. 30. As shown, no check valve may be provided therein, or in association with the medium flow therethrough; however, a check valve could also be provided. Flow restrictor assembly 550a of FIG. 32 is aligned in series along the medium flow path between the syringe 332 and the catheter 334. In one embodiment, the flow restrictor assembly 550a may include a switch plate 560a which is movable relative to a body 562a, in the same manner as described above with respect to switch plate 560 and base 562. Accordingly, tubular member $T_6$ extends from the flow restrictor assembly 550a and is selectively pinched by manipulation of the switch plate 560a in order to selectively restrict medium flow distally from the flow restrictor assembly 550a, and toward the catheter 334. This arrangement could provide an in-line flow resistor along the medium flow path between the syringe 332 and the catheter 334. In one desired arrangement, a minimum flow rate of 2.5 ml/second delivered to the catheter may be necessary to attain the desired opacity of the medium in the vasculature.

While the medium flow rate modulation schemes illustrated and discussed above with respect to FIGS. 30-32 provide additional means for inhibiting the introduction of excess medium into the patient over, and during, an injection profile of such medium, they may be constrained by design to preselected flow diversion or restriction relations of the overall flow of medium from the syringe to the catheter (e.g., splitting that flow into a 40%-60% relation, as an example). Although the flow diverter assembly 550 illustrated in FIG. 30 does allow preselected variations in the flow rate of medium through the flow diverter assembly 550 (by means of the manipulation of switch plate 560), such variations are achieved by manual manipulation of the switch plate 560. The flow diverter assembly 550 of FIG. 30 may not automatically compensate for different pressures or injection flow rates introduced by the syringe operator, as may be seen with the exemplary constant flow modulator 135 illustrated in FIGS. 12A and 12B.

FIGS. 33-37 illustrate an alternative flow diverter assembly 575 that may compensate for a user injecting short (e.g., one second), hard "puffs" of medium (e.g., during catheter navigation) versus long (e.g., two seconds or longer), sustained injections (e.g., during vascular visualization/assessment). Advantageously, diverter assembly 575 may also allow an operator to change the injection delivery system (i.e., guide catheter, stent delivery system, angiographic catheter, etc.) while automatically adjusting the flow of the medium to be sufficient for opacification (likening the function of the constant flow modulator of FIG. 12). The flow diverter assembly 575 may change the resistance to flow rate depending upon changes in the pressure applied to the medium by an operator via the syringe. As resistance is modified to the diverted medium flow rate, the un-diverted flow rate (i.e., the flow rate to the catheter 334) likewise is modified. This arrangement may be useful for minimizing the amount of medium diverted when a syringe operator is attempting to introduce a quick "puff" of medium into the patient. By using a very fast syringe squeeze for that purpose, the operator will tend to achieve opacity in this arrangement more readily than, for example, the arrangement of the flow diverter assembly 550 of FIG. 30. Therefore, flow diverter assembly 575 may be able to reduce the size of area A in FIG. 4B, as compared to flow diverter assembly 550 of FIG. 30. With a long, sustained injection, flow diverter assembly 575 may act similarly as the flow diverter assembly 550 of FIG. 30, in diverting flow away from introduction to the catheter 334.

Figure 33:
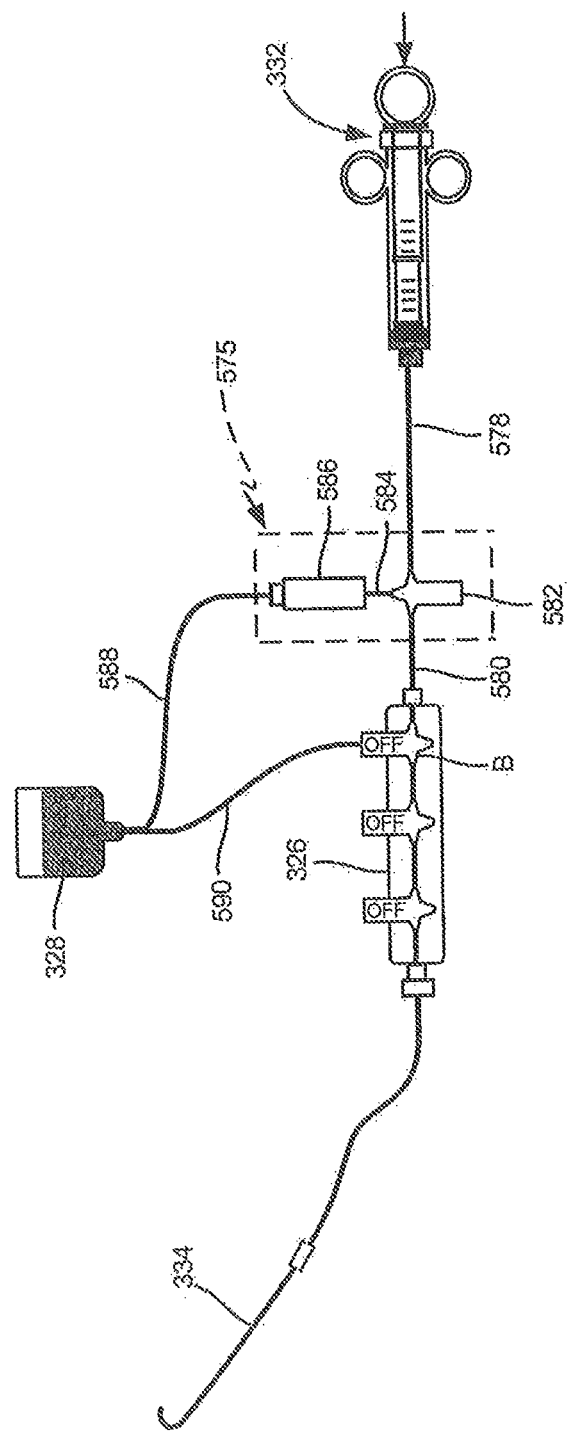
FIG. 33 illustrates an exemplary automatic flow diverter assembly.

The flow diverter assembly 575 may be disposed in the medium flow path between the syringe 332 and the catheter 334, as seen in FIG. 33. In one embodiment, the flow diverter assembly 575 may be positioned between the syringe 332 and the manifold 326, fluidly coupled thereto by tubular members 578 and 580, respectively. Tubular members 578 and 580 may be connected to the fittings of a four way stopcock 582, which in turn is connected by a further tubular member 584 to a valve 586. The stopcock 582 is disposed between the syringe 332 and the delivery catheter 334 in the fluid medium flow path. The stopcock 582 is operably connected to the syringe 332 such that manipulating the stopcock 582 allows a user to selectively activate and inactivate the flow diverter assembly 575. Valve 582 is operably connected to stopcock 582. In one embodiment, the stopcock 582 and valve 586 may be separate components, coupled via the tubular member 584. In another embodiment, the stopcock 582, tubular member 584 and valve 586 are configured as one self-contained component that can simply be inserted into the medium flow path between the syringe 332 and the catheter 334. In either configuration, another tubular member 588 extends from the valve 586 to a medium overflow and/or re-use reservoir 328. In one embodiment, the medium reservoir 328 may also serve as the supply reservoir for loading the syringe 332 with medium. In that arrangement (as illustrated in FIG. 33), syringe 332 is fluidly coupled to medium reservoir 328 by tubular members 590, 580 and 578, coupling those components together via a fluid coupling element or assembly. In an exemplary embodiment, the fluid coupling element or assembly includes manifold 326 and stopcock 582. The manifold has a manifold lumen therethrough and includes a first medium port fluidly coupled to the flow diverter assembly 575, a second medium port fluidly coupled to the medium reservoir 328, and a third medium port fluidly coupled to the delivery catheter 334. When the syringe 332 is being loaded with medium from the medium reservoir 328, the stopcock 582 may be positioned to permit medium flow between tubular members 580 and 578, but not to tubular member 584 disposed between the stopcock 582 and the valve 586. Once the syringe 332 is loaded with medium from medium reservoir 328, then valve B on manifold 326 may be manipulated to prohibit flow back to medium reservoir 328 via tubular member 590, and the stopcock 582 may be positioned to allow flow through the tubular members 578, 584, 580 and manifold 326.

Figure 34:
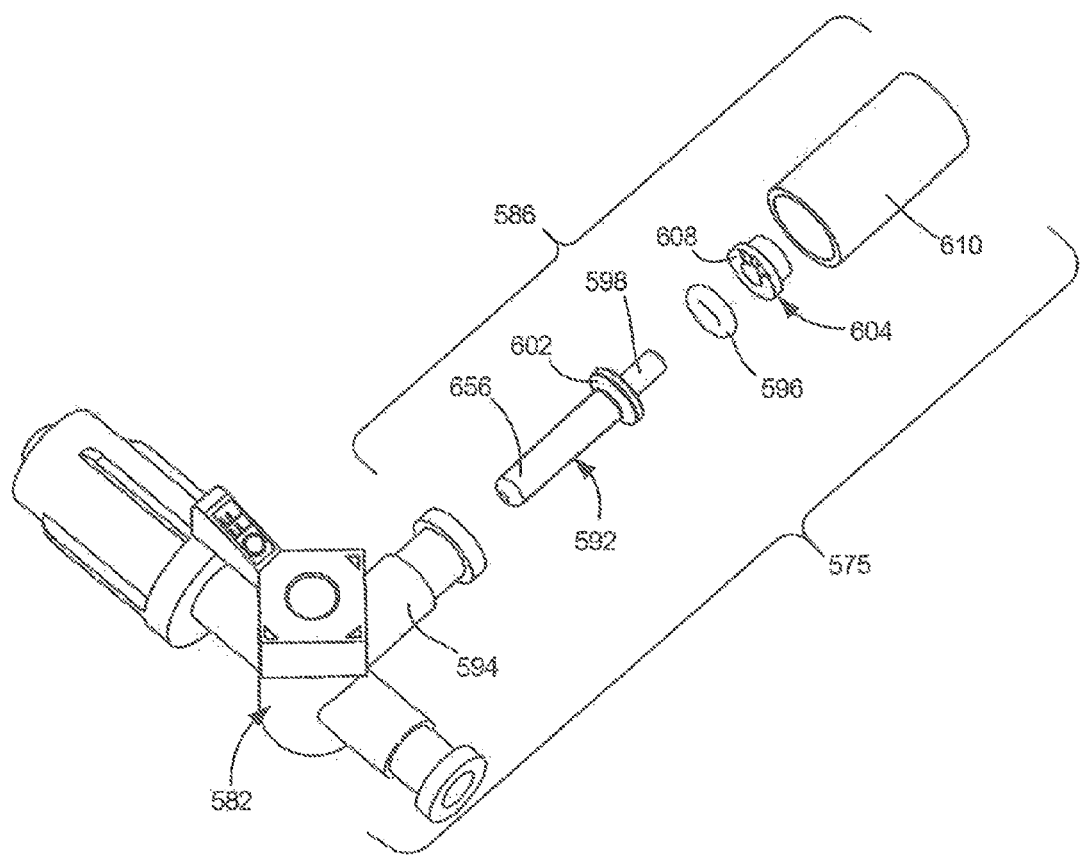
FIG. 34 is an exploded perspective view of the automatic flow diverter assembly of FIG. 33.
Figure 35:
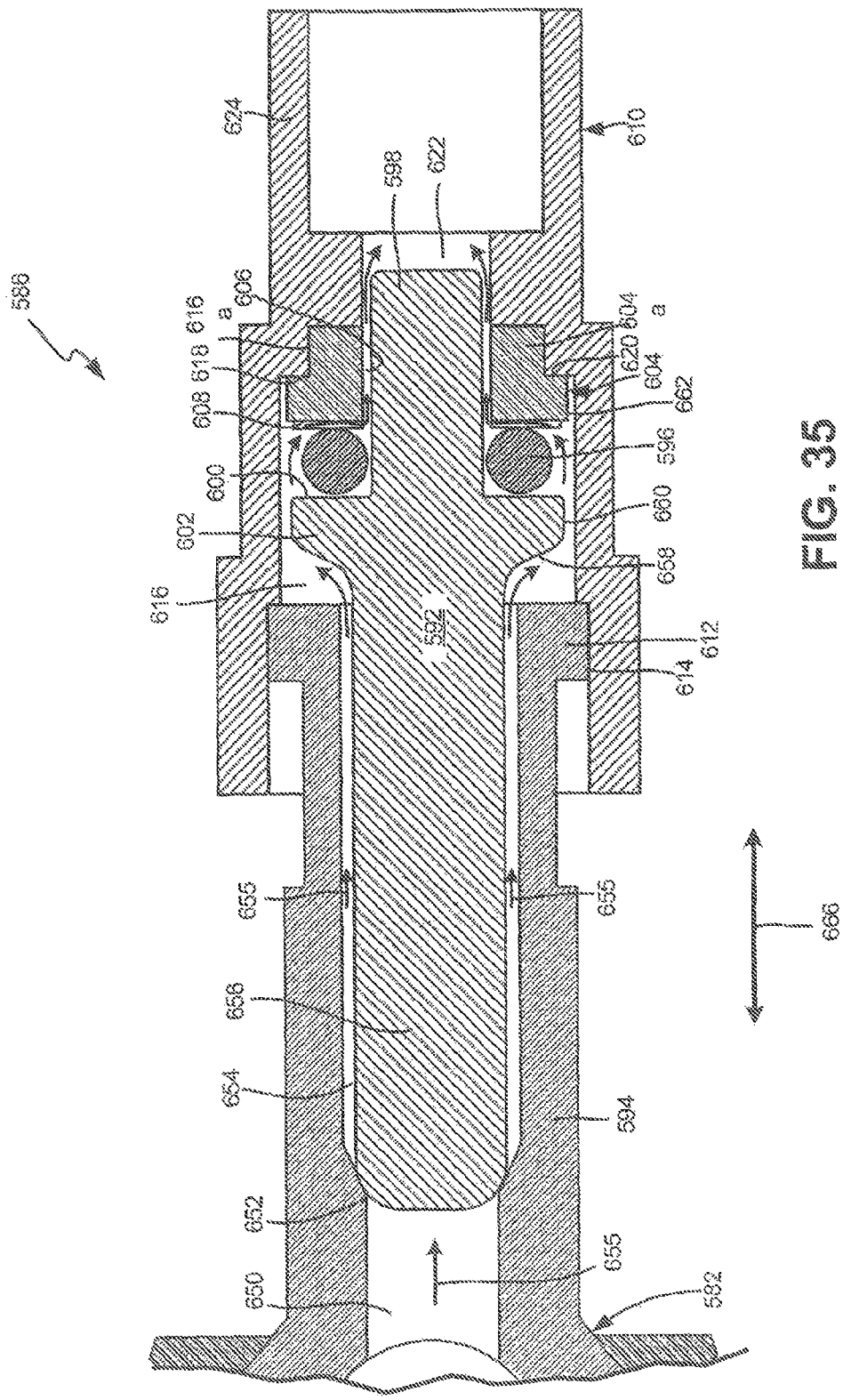
FIG. 35 is a sectional view of a valve in the automatic flow diverter assembly of FIGS. 33 and 34.
Figure 36:
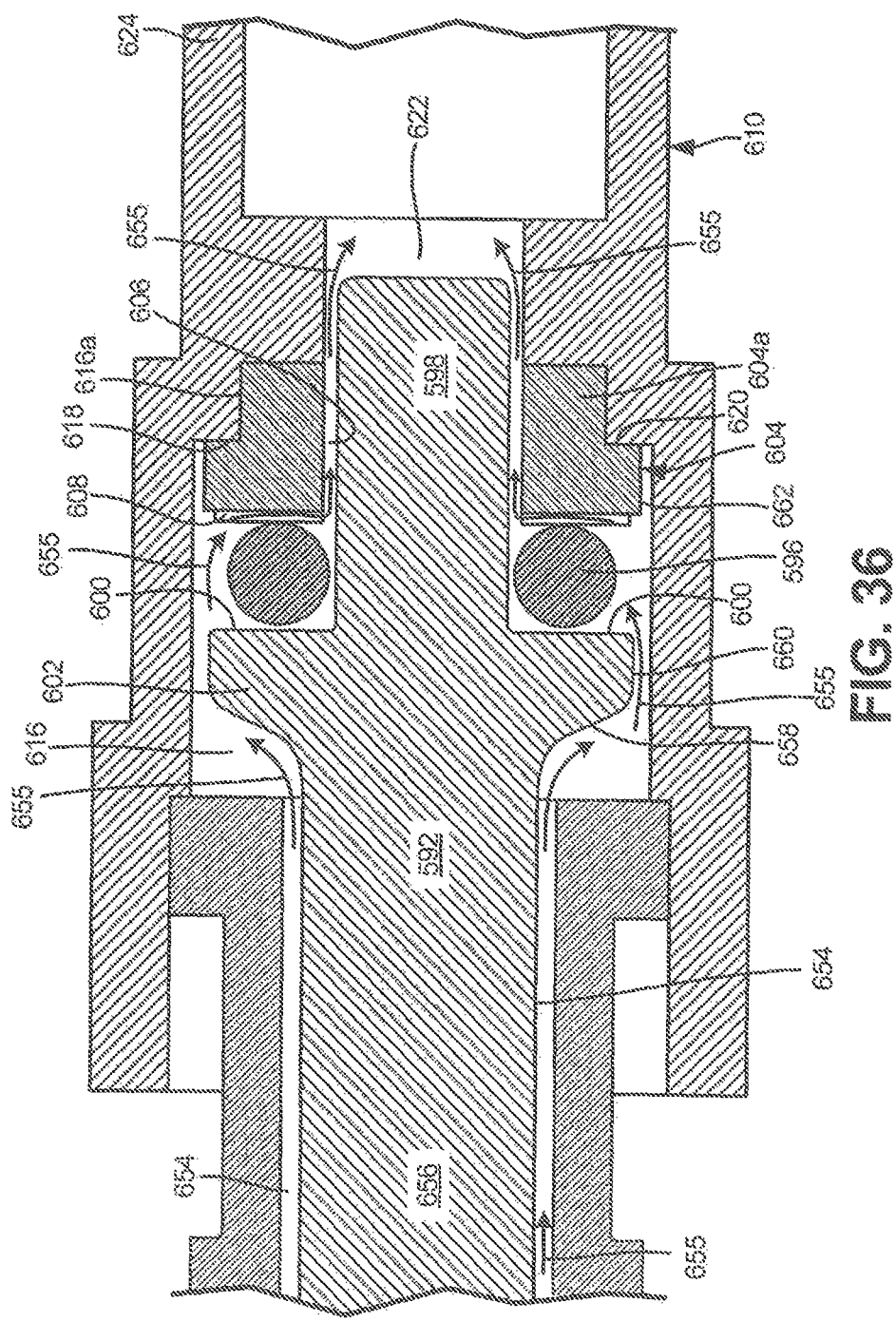
FIG. 36 is an enlarged perspective view of a portion of FIG. 35.

One embodiment of the flow diverter assembly 575 is illustrated in FIG. 34, with the components of the valve 586 shown in exploded axial relation relative to the stopcock 582 thereof. FIG. 35 is a sectional view of the assembled components of the valve 586 and the stopcock 582 illustrated in FIG. 34, while FIG. 36 is an enlarged sectional view of a portion of FIG. 35. The valve 586 includes a diffuser 592 which may be at least partially received within a tubular diverter arm 594 of the stopcock 582. The movable diffuser 592 is activated to move with pressure, and the diverter arm 594 is capable of increasing or decreasing a medium flow resistance through the diverter arm 594. The diffuser 592 comprises a radial shoulder 602, and the valve 586 comprises a deformable O-ring 596 disposed between the radial shoulder 602 and a face 608 of a valve compression plate 604. The valve 586 includes a deformable and resilient O-ring 596 that extends over a cylindrical extension 598 of the diffuser 592, until it is seated against a radially extending face 600 on a radial shoulder 602 of the diffuser 592. A generally disc-shaped valve compression plate 604 has a central cylindrical bore 606 therethrough which is larger than the outer diameter of the cylindrical extension 598 of the diffuser 592. The compression plate 604 (as shown in FIG. 35 as being disposed over the extension 598) has a first face 608 that abuts the O-ring 596. The diffuser 592, O-ring 596 and compression plate 604 are all retained on the diverter arm 594 of the stopcock 582 by a valve housing 610. In an exemplary embodiment, the valve housing 610 is attached to the diverter arm 594, and the valve housing 610 and the diverter arm 594 define an internal chamber 616 therein, the internal chamber 616 having longitudinal axis therethrough. The valve housing 610 is sealably coupled to a distal end 612 of the diverter arm 594, as at area 614, to form a single component serving as flow diverter assembly 575. The valve housing 610 has a first internal chamber 616 for receiving the compression plate 604, O-ring 596 and a portion of the diffuser 592, including radial shoulder 602. The first internal chamber 616 includes a radially extending face 618 that abuts in generally planer engagement with a face 620 of the compression plate 604. The first internal chamber 616 also includes a cylindrical socket 616a sized to receive a cylindrical projection 604a of the compression plate 604 therein. The valve housing 610 has a second internal chamber 622 which receives a portion of the cylindrical extension 598 of the diverter 592 therein. The second chamber 622 is in fluid communication with the first internal chamber 616 (via the bore 606 in the compression plate 604), and with a fitting 624 on the valve housing 610. The fitting 624 is configured for fluid connection to tubular member 588 (e.g., see FIG. 33).

As with the flow diverter arrangement illustrated in FIG. 30, a portion of the injected medium flow from the syringe 332 may be diverted away, in this case by the flow diverter assembly 575. In an exemplary embodiment, the flow diverter assembly 575 is configured to divert at least some of the fluid medium within the chamber of the syringe 332 to the medium reservoir 328 when a threshold pressure level of the fluid medium within the flow diverter assembly 575 is reached. The diverted medium flows through a first cylindrical flow channel 650, past an annular check valve seat 652 and into a second larger (in diameter and thus cross-sectional area) cylindrical flow channel 654, all still within an internal chamber 616 of the diverter arm 594 of the stopcock 582 (as illustrated by flow arrows 655 in FIGS. 35 and 36). The valve 586 further comprises a deformable o-ring disposed between an end of the diffuser 592 and the annular check valve seat 652. The annular check valve seat 652, when abutted by the diffuser 592, limits such flow until sufficient pressure (e.g., a flow diversion threshold pressure level) is exerted by the injected medium to move the diffuser 592 off of the annular check valve seat 652 (thereby overcoming the bias exerted by the O-ring 596 on the diffuser 592). Medium flow continues away from the stopcock 582 through flow channel 654 and around a cylindrical portion 656 of the diffuser 592, along a generally tubular flow path. As medium flow exits the flow channel 654, it may enter the first internal chamber 616 of the valve housing 610, and encounter a ramped, radially extending face 658 of the shoulder 602 of diffuser 592. An outer circumferential edge 660 of the shoulder 602 has a smaller circumference than an opposed inner circumference of the first internal chamber 616, so flow may continue past the shoulder 602 between its circumferential edge 660 and an inner wall of the first chamber 616 (see, e.g., along a generally tubular flow path as illustrated by flow arrows 655 in FIG. 36). Medium flow may then continue past the O-ring 596 and encounter the compression plate 604. The face 608 of the compression plate 604 may have one or more grooves radially extending therein, between its inner opening 606 and outer circumferential face 662.

FIGS. 37-41 illustrate an exemplary compression plate 604, with grooves 664a, 664b and 664c therein. While a plurality of such grooves are illustrated in FIGS. 37-41, one groove or some other form of surface discontinuity may suffice to permit fluid flow across the proximal face 608 of the compression plate 604. In the embodiment illustrated in FIGS. 37-41 of the compression plate 604, groove 664a extends radially outwardly across the proximal face 608 of the compression plate 604, from the inner opening or bore 606 therein to its outer circumferential face 662. The groove 664a also becomes wider as it radiates outwardly (so that is it wider at the outer circumferential face 662 than at the inner opening 606), with its groove edges 665a defined by radial lines extending from a central axis of the compression plate 604. In one embodiment, the arc defined by the groove 664a is 40 degrees of the circumference of the compression plate 604. The groove 664b likewise extends radially outwardly from the bore 606 of the compression plate 604 to its outer circumferential face 662 across the proximal face 608 of the compression plate 604. The groove 664b also becomes wider as it radiates outwardly (so that is it wider at the outer circumferential face 662 than at the inner opening 606), with its groove edges 665b defined by radial lines extending from a central axis of the compression plate 604. Groove 664b may be larger than the groove 664a in one embodiment, with the arc defined thereby being 60 degrees of the circumference of the compression plate 604. Groove 664c is disposed, in the illustrated embodiment, entirely within 664b and is defined by a pair of parallel groove edges 665c extending between the bore 606 and the outer circumferential face 662. The groove 664c defines a deeper groove channel 666 within the groove channel already formed by the groove 664b. In one exemplary embodiment, as illustrated in FIG. 38, centerlines for each of the grooves may be collinear.

Viewing FIG. 35 and FIG. 36 again, medium introduced from the stopcock 582 and through the first chamber 616 adjacent the O-ring 596 may flow radially inwardly (between the O-ring 596 and the compression plate 604) via the grooves 664a, 664b and 664c and into the bore 606 which, as noted above, may have a circumference larger than the outer diameter of the distal extension 598 of the diffuser 592. Medium can thus flow along a generally tubular flow path through the compression plate 604 (via its bore 606) and around the portion 598 of the diffuser 592 and into the second internal chamber 622 of the valve housing 610 (see, e.g., flow arrows 655 in FIG. 36). From there, medium can further flow into the tubular member 588 connected to the fitting 624 on the valve housing 610. The medium pressure acting on the compression plate 604 urges its face 620 against opposed radially extending face 618 of the first internal chamber 616, thus creating a barrier to flow by medium past the compression plate 604, except through the bore 606 (e.g., passing along grooves 664a, 664b and/or 664c on face 608 of compression plate 604).

As the pressure is increased in the medium within the flow diverter assembly 575, greater fluid pressure is exerted against the face 658 of the diffuser 592, thereby urging the diffuser 592 against the O-ring 596 and an end of the valve housing 610. This in turn compresses the O-ring 596 against the face 608 of the compression plate 604 and into flow channels defined by each groove thereon, to reduce the effective channel size of the grooves and thereby inhibit the flow of medium across the proximal face 608 of the compression plate 604. As the pressure acting on the face 658 of the diffuser 592 increases, the O-ring 596 is further compressed and further inhibits the flow of medium past the compression plate 604. For instance, with respect to the stepped grooves 664b and 664c, the O-ring 596 may first deform to inhibit flow through shallower groove 664b. Further deformation of the O-ring 596 may cause it to then inhibit flow through deeper groove 664c, progressively. Likewise, as pressure is lessened, the pressure exerted by the diffuser 592 on the O-ring 596 is lessened and more medium is allowed to flow between the O-ring 596 and the compression plate 604 through the flow channels defined by the grooves. The diffuser 592 thus "floats" within the flow diverter assembly 575 in direction of arrows 666 (FIG. 35) and forms a floating valve element that may change the amount of medium flow allowed, depending upon the pressure of the medium flow entering the valve 586. The diffuser 592 is received within the internal chamber 616, the diffuser 592 being movable along the longitudinal axis of the internal chamber 616. The diffuser 592, in combination with the deforming O-ring 596, and face 608 of the compression plate 604, may form a deforming valve that is pressure compensating for medium flow through the flow diverter assembly 575. This arrangement may allow a syringe operator to vary the type of injection of medium using the syringe 332 (e.g., short puff versus a long, sustained injection), but still attain flow diversion characteristics that serve to minimize the amount of excess introduction of medium into the patient.

In one embodiment such as illustrated in FIGS. 34-36, the diffuser 592 of the valve 586 is formed of a material that may deform at its end, adjacent annular check valve seat 652, to serve as a check valve and prevent fluid flow from the flow diverter assembly 575 back into the main flow line between the syringe 332 and the catheter. In an alternative embodiment, such as illustrated in FIGS. 42 and 43, a flow diverter assembly 575a is essentially the same in configuration and function as the flow diverter assembly 575 described above, except for the diffuser in valve 586a. As seen in FIGS. 42 and 43, a modified diffuser 592a may include a O-ring support shank 592b formed to receive and retain a deformable and resilient O-ring 592c thereon. The O-ring 592c is thus provided between the end of the diffuser 592a and the annular check valve seat 652 (e.g., see FIG. 35) to provide the check valve function, described previously.

As may be appreciated, the shapes of the grooves or discontinuities on the face 608 of the compression plate 604 and the compressibility of the O-ring 596 must be compatible to attain the desired flow control characteristics between those components, when the O-ring 596 is compressed against the face 608 of the compression plate 604 by movement of the diffuser 592. Changes in the material forming the O-ring 596 (either being more or less deformable) relative to the same compression plate 604 configuration will change the rate of flow modification depending upon pressure changes in the fluid medium in the valve 586. In addition, while a deformable O-ring in conjunction with a radial face having surface discontinuities is illustrated as one embodiment for forming a pressure compensating valve in a flow diverter assembly 575, other variable flow mechanisms may also suffice. For example, a disc that expands dependent upon pressure over an array of medium flow holes, to progressively cover more holes as more pressure from the medium is applied to the disc or to a related component, will likewise suffice to serve as a flow constrictor. In many cases, full exclusion of medium flow past the compression plate 604 may not be indicated. Valve 586 may allow some medium flow therethrough, at all applied fluid pressures, once a minimum pressure threshold is exceeded (such as, again, e.g., 20 psi).

It is anticipated that valve 586 may be configured to be adjustable by an operator. For example, medium flow through the valve 586 may be changed by modifying the size of the flow channel 654, such as by modifying the diameter of the portion 656 of the diffuser 592 by enlargement/reduction (i.e., mechanically, inflatably, etc.,) thereby changing the effective cross-sectional area of the generally tubular flow path along the diffuser 592. This is but one way that the valve 586 may be configured so as to be adjustable, and should not be construed so as to limit the scope of the invention. The capability of adjusting the valve may allow an operator the ability to make changes mid-procedure (e.g., changing out a diagnostic catheter for a treatment system), as seen, for example, in diverters described in FIGS. 33-43.

FIGS. 52-57 illustrate another medium management system 825 that may include, as shown in the illustrated embodiment, flow diverter assembly 575 and a diversion reservoir 827. In this embodiment, tubular member 588a extends from the valve 586 of the flow diverter assembly 575 to a medium diversion reservoir 827, and tubular member 588b extends from diversion reservoir 827 to medium reservoir 328. Medium from the medium reservoir 328 is permitted to flow away from the medium reservoir 328 and through diversion reservoir 827 via tubular members 588b and 588a, as well as via tubular member 590. In the illustrated arrangement (see e.g., FIG. 52), syringe 332 may be fluidly coupled to medium reservoir 328 by tubular members 588b, 590, 580 and 578, coupling those components together by a manifold 326 and through stopcock 582. When the syringe 332 is being loaded with medium from medium reservoir 328, the stopcock 332 may be positioned to permit medium flow between tubular members 580 and 578, but not to tubular member 584 disposed between the stopcock 582 and the valve 586 of the flow diverter assembly 575. Drawing back the syringe 332 may pull medium from the medium reservoir 328 through tubular member 588b, and/or diversion reservoir 827, and through tubular member 590. Medium from the medium reservoir 328 may then be further drawn, into and toward, syringe 332 through tubular members 580 and 578. Once the syringe 332 is loaded with medium from medium reservoir 328, valve B on manifold 326 may then be manipulated to prohibit flow back to medium reservoir 328 via tubular member 590 (and such flow may be further inhibited by a check valve disposed between diversion reservoir 827 and medium reservoir 328), and the stopcock 582 may be positioned to allow flow through the tubular members 578, 584, 580 and manifold 326.

As noted above with respect to exemplary modulator systems illustrated in FIGS. 33-43, a portion of the injected medium flow from the syringe 332 may be diverted away from the medium flow path to catheter 334 by the flow diverter assembly 575. In the modulation/reservoir system 825 illustrated in FIGS. 52-57, such diverted medium flow passing through the flow diverter assembly 575 flows into the diversion reservoir 827, as opposed to flowing directly into the medium reservoir 328 or some other outflow/overflow reservoir/chamber. Advantageously, the diversion reservoir 827 provides means for collecting overflow medium diverted by the flow diverter assembly 575, for possible re-use as the syringe 332 may be again activated to pull medium into the system (e.g., for introduction into the patient via catheter 334). The use of such a diversion reservoir in this manner, with an associated check valve preventing back flow of medium into the medium reservoir 328, allows for capture and re-use of medium that is already introduced into the system (e.g., in the diversion reservoir 827) while preserving the integrity of the medium disposed within medium reservoir 328 in its original form.

One embodiment of the diversion reservoir 827 is illustrated in FIGS. 53-56. FIG. 53 shows an assembled view of diversion reservoir 827 along with its associated tubular members 588a and 590. FIG. 54 is an exploded view of the assembly of FIG. 53. The system 825 further comprises a second supply conduit 590 in fluid communication with the supply conduit 588b and the diversion conduit 588a, wherein the second supply conduit 590 is fluidly coupled to the fluid medium flow path. Tubular members 588a and 590 are sealably connected to a first end cap or manifold 835 on diversion reservoir 827, as further shown in FIG. 55, which is a sectional view taken through lines 55-55 in FIG. 53. A first end of a through-tube 837 is sealably connected to an interior side of first end cap 835, as at 838. Through-tube 837 includes an inner conduit 839 extending therethrough. Inner conduit 839 is in fluid communication with the interiors of tubular members 588a and 590 via their adjacent couplings in the first end cap 835, as illustrated in FIG. 55. A second end of through-tube 837 is sealably connected to a check valve assembly 841, as at 842, and the inner conduit 839 is in fluid communication with the check valve assembly 841. The check valve assembly 841 is, in turn, in fluid communication with the tubular member 588b. As seen in FIG. 55, the check valve assembly 841 includes a moveable valve plate 843 (or other suitable structure allowing one way flow through the valve) which is operable to permit flow from the medium reservoir 328 via tubular conduit 588b into the inner conduit 839 of through-tube 837, but to inhibit flow in reverse thereof. This arrangement may allow flow of medium from fluid reservoir 328 via tubular conduit 588b, inner conduit 839 of through-tube 837, and tubular conduit 590 to the syringe 332. Moreover, medium flow diverted by flow diverter assembly 575 may also be permitted to flow via tubular member 588a into inner conduit 839 of through-tube 837, but inhibited from flowing back to the medium reservoir 328 by check valve assembly 841. A second end cap 844 on diversion reservoir 827 is secured about the check valve assembly 841.

The diversion reservoir 827 is designed to accommodate such back flow of medium from the flow diverter assembly 575, to collect and hold such medium and then, if desired, urge such collected medium back into the system for use in delivering additional medium to the patient via injection catheter 334. To accomplish this end, diversion reservoir 827 may include an elastic expansion tube 845 disposed about through-tube 837. As seen in FIGS. 55 and 56, expansion tube 845 extends along a portion of a length of through-tube 837. In one embodiment, expansion tube 845 is formed of silicone material sealably secured adjacent each end thereof about the through-tube 837 by first and second retention washers 847 and 849, respectively, or by other suitable sealable and mechanical fastening arrangements. An outer surface of the through-tube 837 may include interference elements such as surface features or an annular interference rim 837*a* (see FIG. 55) to further facilitate the sealing of the expansion tube 845 to the through-tube 837 via the retention washer 847 and 849.

A housing tubular outer shell 855 may be connected between the first end cap 835 and second end cap 844, thereby covering the expansion tube 845 and other diversion reservoir components therein. The shell 855 may serve to protect the components of the diversion reservoir 827 therein, limit the extent of inflation or expansion of expansion tube 845, and/or (if the shell 855 is either transparent or translucent) allow observation of the condition (e.g., expanded state) of expansion tube 845 therein.

FIG. 56 illustrates the diversion reservoir 827 in perspective sectional view (again, as taken along lines 55-55 in FIG. 53) with the expansion tube 845 shown in an exemplary stretched and expanded state, as opposed to its relaxed state shown in FIG. 55. The expansion tube 845 of the diversion reservoir 827 receives medium flow from the flow diverter assembly 575, via tubular member 588*a*. This medium flow, as illustrated by flow arrows 857 in FIG. 56, flows from tubular member 588*a* into the inner conduit 839 of through-tube 837 adjacent the first end of through-tube 837. Flow out of the through-tube 837 is inhibited at its second end by the check valve assembly 841. However, the supply conduit through-tube 837 may have one or more apertures 859 therethrough which allows an interior of the expansion tube 845 to be in fluid communication with the inner conduit 839 and reservoir chamber 860. Medium from the flow diverter assembly 575 can thus flow through apertures 859 and into a medium reservoir or chamber 860 defined by the expansion tube 845. This medium chamber 860 is defined between the inner surface of expansion tube 845 and the outer surface of through-tube 837, whereby the expansion tube 845 forms an elastic bladder disposed around the supply conduit 837, with the walls of expansion tube 845 capable of imparting a force on the fluid medium within the chamber 860. A surface within chamber 860 is capable of imparting a variable or constant force on the fluid medium within the chamber 860, and the surface is defined at least in part by a wall of the elastic bladder of expansion tube 845. The medium chamber 860 thus receives and collects the diverted portion of the flow of medium from the flow diverter assembly 575. The diversion reservoir 827 comprises a variable or constant force biasing member disposed relative to at least one surface within the reservoir chamber 860 to urge the surface against the fluid medium within the reservoir chamber 860. The expandable wall of the expansion tube 845 thus defines a surface within the medium chamber 860 capable of imparting a force (variable or constant) on the fluid medium within the medium chamber 860. In one embodiment, the second end cap 844 includes an aperture 861 therethrough to permit the escape of gas within the cover 855 and thereby readily permit expansion of the expansion tube 845 therein.

In use, as the pressure of medium within the flow diverter assembly 575 increases enough to allow flow therethrough, medium flows from the valve 586 via the tubular member 588*a* to the diversion reservoir 827. Medium then flows within the diversion reservoir 827 as illustrated by arrows 857 into medium chamber 860, thereby stretching the walls of the expansion tube 845 and expanding chamber 860 to accommodate the diverted medium flow. Accordingly, as the medium pressure provided via syringe 332 increases in the system, the flow diverter assembly 575 diverts medium so that the flow to the patient increases as less flow is diverted by the flow diverter assembly 575 into the diversion reservoir 827. The medium contained in the chamber 860 may be available for further infusion into the patient via the modulation/reservoir system 825. As an example, an operator may activate valve B to allow medium flow from the chamber 860 of the diversion reservoir 827 into the syringe 332 (which is being withdrawn to draw such fluid therein). If the fluid needed is greater than the volume retained within the chamber 860, the force of check valve 843 is overcome and further medium is withdrawn from the medium reservoir 328. Once a sufficient amount of medium has been withdrawn from the chamber 860 and/or reservoir chamber 328, valve B may be closed and the modulation/reservoir system 825 may be again in condition for delivery of medium via injection catheter 334, by activation of injection syringe 332 by an operator. As long as the stopcock 582 is disposed to allow flow into tubular members 580 and 584, the flow modulator assembly 575 may automatically activate to divert excess medium, thereby ultimately reducing the amount of medium introduced into the patient via injection catheter 334 (e.g., thus introducing no more medium than necessary to attain operative opacity). Again, as the pressure is increased in the modulator 575, the flow to the patient is actually decreased by operation of the flow diverter assembly 575. The process can be repeated by an operator as many times as deemed necessary to complete the procedure desired. Use of the modulation/reservoir system 825 in this manner may achieve the advantageous reduction of introduction of unnecessary medium into the patient while achieving the necessary amount and flow of medium in the patient for diagnostic or treatment means (e.g., for opacity). In addition, the diversion reservoir 827 may allow re-use of the diverted outflow of medium.

The diversion reservoir illustrated in FIGS. 53-56 presents one form of such a reservoir. Alternative forms are contemplated as well. For example, an alternative form of elastic bladder or elastic surface may be provided that functionally allows the receipt of medium overflow from the flow diverter assembly 575 into an expansion chamber, and then further allows the flow of medium from the medium reservoir 328 through the diversion reservoir 827 and into the modulation/reservoir system 825 for use. An alternative means of placing force on the medium within the chamber in the diversion reservoir 827 may be attained by a bias plunger, such as illustrated schematically in FIG. 57. The diverted portion of the fluid medium flows through a diversion conduit 588*a* away from the flow diverter assembly 575. The system 825 comprises a medium reservoir 328 containing a supply source of fluid medium for the system 825 and a supply conduit 588*b* through the reservoir chamber 834 that fluidly connects the medium reservoir 328 and the diverter conduit 588*a*. The supply conduit 588*b* comprises a check valve 841*a* to prevent the flow of fluid medium from the supply conduit 588*b* into the medium reservoir 328. Diversion reservoir 827a includes a plunger 828 slidably disposed in housing 826 and moveable in a linear fashion relative to the housing 826, as illustrated by movement line 830. Thus, the surface 832 is movable in a linear direction relative to the fluid medium within the reservoir chamber 834. A proximal face or surface 832 of the plunger 828 thus defines a portion of a chamber 834 within the housing 826 for diverted medium that is received therein via the tubular member 588a.

Figure 57:
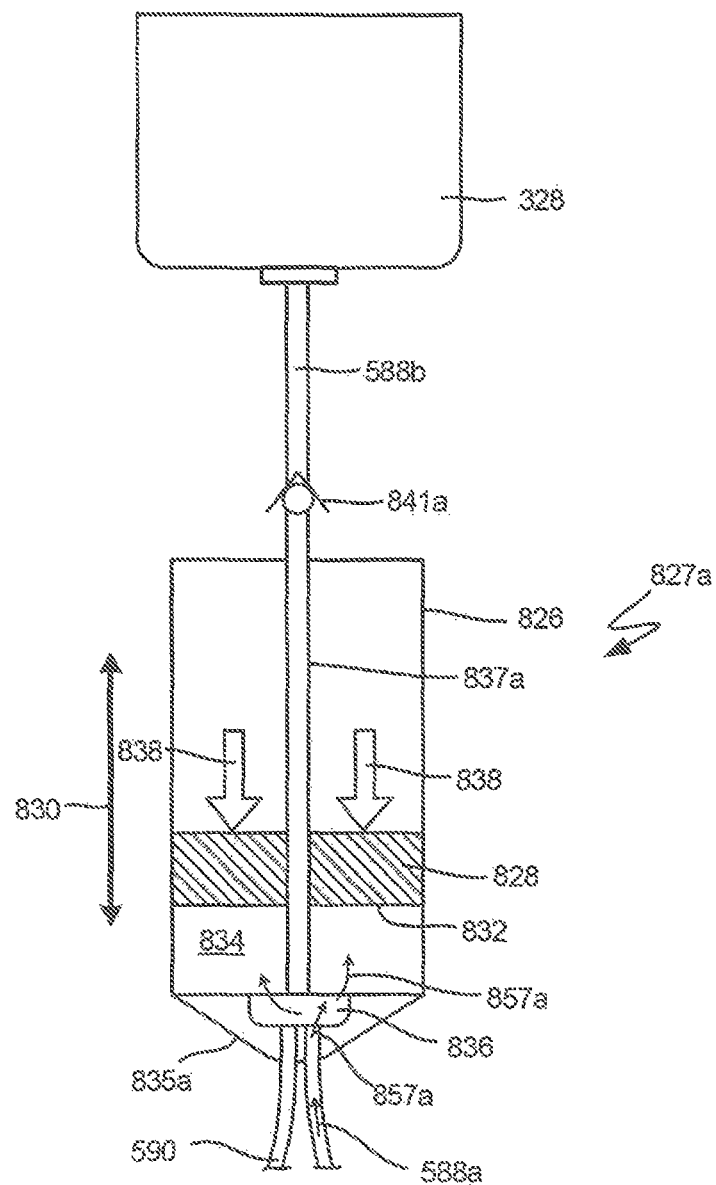
FIG. 57 illustrates another exemplary medium diversion reservoir.

Like the diversion reservoir 827 illustrated in FIGS. 53-56, diversion reservoir 827a may include a first end cap 835a that acts as a manifold for medium flow. Tubular member 588a is connected to first end cap 835a, as is tubular member 590. Chamber 834 is in fluid communication with the interiors of tubular members 588a and 590, such as via manifold 836 within the first end cap 835a, as seen in FIG. 57. A through-tube 837a is also in fluid communication with the manifold 836, and extends through the housing 826 of the diversion reservoir 827a to a check valve 841a. Check valve 841a permits medium flow from medium reservoir 328 via tubular member 588b into through-tube 837a but prevents backflow. Medium from the medium reservoir 328 can then flow from the diversion reservoir 827a into the syringe 332 via tubular member 590.

When medium is diverted by the flow diverter assembly 575 into the diversion reservoir 827a, medium flows as illustrated by flow arrows 857a from tubular member 588a, through manifold 836, and into the chamber 834. The diversion reservoir 827a comprises a variable or constant force biasing member disposed relative to at least one surface 832 within the reservoir chamber 834 to urge the surface 832 against the fluid medium within the reservoir chamber 834. In an exemplary embodiment, surface 832 is planar. The face 832 of the plunger 828 is biased toward the manifold chamber 836, and thus defines a moveable surface 832 for the chamber 834 that can move away and expand chamber 834 as more medium is introduced therein, when the bias of the force acting against it is overcome. This bias may be in the form of a constant or variable force acting on the plunger 828 within the housing 826, as illustrated schematically by force arrows 838, and such force may be achieved by suitable means such as springs, weight distribution, linear actuator, etc. The use of a linearly moving plunger 828 (as its movement is illustrated by arrows 830) may permit more ready measurement of how much medium has actually been diverted by the flow diverter assembly 575 and thereby, by derivation, how much medium has actually been delivered to a patient by the injection catheter 334. The plunger 838 thus provides a linear expansion element (surface 832) that serves to apply force to the overflow medium collected for possible re-use in the chamber 834.

Figure 58:
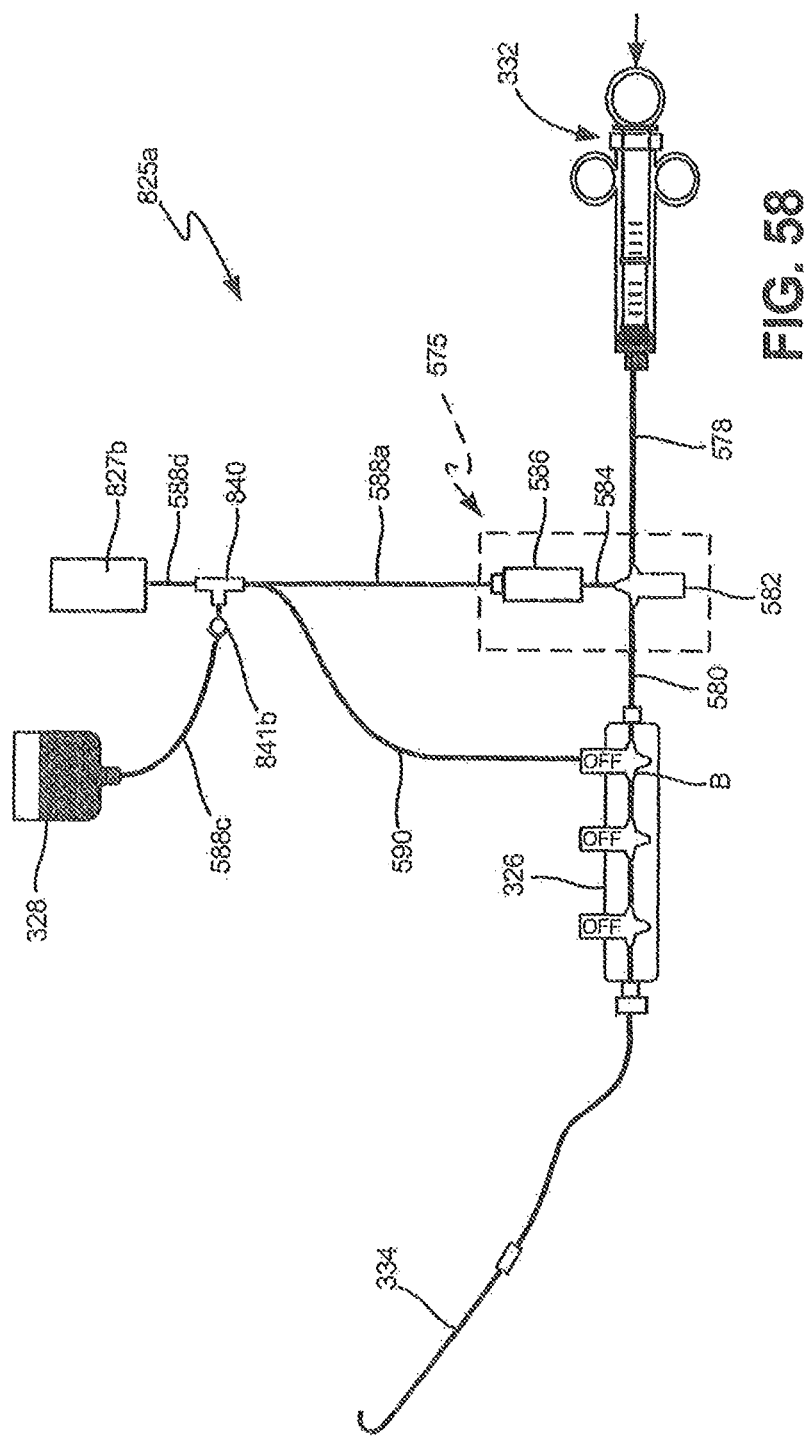
FIG. 58 illustrates another exemplary medium management system.

The diversion reservoir 827a operates in a similar manner to the diversion reservoir 827, discussed above, by providing an expandable chamber for medium diverted by the flow diverter/modulating assembly 575, wherein the chamber (e.g., chamber 834, 860) has at least one surface acting upon it to urge the medium therein back to the flow diverter assembly 575 for possible re-use. Likewise, medium which has been diverted by the flow diverter assembly 575 into the diversion reservoir chamber 834 is not permitted to flow back to the medium reservoir 328, via check valve 841a. In alternative embodiments for modulation/reservoir systems, the diversion reservoir is configured so that flow through it to the medium reservoir is not permitted or necessary. One such arrangement is illustrated in FIG. 58, in connection with a modulation/reservoir system 825a. In these arrangements, there may be no necessity for a through-tube arrangement through the diversion reservoir. The diversion reservoir simply provides an expandable chamber therein for retaining and re-using medium diverted from the flow diverter assembly 575. Such diversion reservoirs 827b may employ a bladder form of chamber or a constant or variable force resistance form of chamber, such as those illustrated and discussed herein, where at least one surface therein is capable of imparting a force on the fluid medium within the chamber. FIG. 58 illustrates an arrangement where the medium reservoir chamber 328 is connected via tubular member 588c to a T-connector 840 disposed between a diversion reservoir 827b (without a through-tube) and the flow diverter assembly 575. The T-connector 840 connects at its first end to the tubular members 590 and 588a, and at its second end to tubular member 588d that leads to the diversion reservoir 827b. A side fitting of the T-connector 840 leads via tubular member 588c to the medium reservoir 328. A check valve 841b is disposed between the T-connector 840 and the medium chamber 328 to prevent back flow of medium from the flow diverter assembly 575 and/or diversion reservoir 827b into the medium container 328. In operation, the configuration illustrated in FIG. 58 may be similar to that described above with respect to FIG. 52. As the pressure of medium within the flow diverter assembly 575 increases enough to allow flow therethrough, medium flows from the valve 586 via tubular member 588a to the T-connector 840. Medium may then flow from the T-connector 840 via tubular member 588d to the diversion reservoir 827b. Medium flowing into the diversion reservoir 827b expands the expandable chamber therein to accommodate the diverted medium flow. Accordingly, as the medium pressure provided via syringe 332 decreases in the system, the flow diverter assembly 575 diverts medium so that the flow to the patient decreases as more flow is diverted by the flow diverter assembly 575 into the diversion reservoir 827b.

In operation, the configuration illustrated in FIG. 58 may be similar to that described above with respect to FIG. 52. As the pressure of medium within the flow diverter assembly 575 increases enough to allow flow therethrough, medium flows from the valve 586 via tubular member 588a to the T-connector 840. Medium may then flow from the T-connector 840 via tubular member 588d to the diversion reservoir 827b. Medium flowing into the diversion reservoir 827b expands the expandable chamber therein to accommodate the diverted medium flow. Accordingly, as the medium pressure provided via syringe 332 decreases in the system, the flow diverter assembly 575 diverts medium so that the flow to the patient decreases as more flow is diverted by the flow diverter assembly 575 into the diversion reservoir 827b.

The medium contained in the expandable chamber within the diversion reservoir 827b may be available for further infusion into the patient via the modulation/reservoir system 825a. To do so, an operator activates valve B to allow medium flow from the chamber within the diversion reservoir 827b into the syringe 332 (which is being withdrawn to draw such fluid therein). If the fluid needed is greater than the volume retained in the chamber reservoir 827b, the force of check valve 841b is overcome and further medium is then withdrawn from the medium reservoir 328. Once a sufficient amount of medium has been withdrawn from the chamber within the diversion reservoir 827b and/or reservoir chamber 328, valve B is again closed and the modulation system 825a is again in condition for delivery of medium via injection catheter 334, by activation of injection syringe 332 by an operator. As long as the stopcock is disposed to allow flow into tubular members 580 and 584, the flow diverter assembly 575 will then again be automatically activated to divert excess medium when a threshold pressure for activation of the flow diverter assembly 575 is attained, thereby ultimately reducing the amount of medium introduced into the patient via injection catheter 334. Again, as pressure is increasing going into flow diverter system 575, the flow through the diverter 575 is relatively decreasing (thus, flow to the patient may be relatively increasing by operation of the flow diverter assembly 575). The process can be repeated by an operator as many times as deemed necessary to complete the procedure desired. Use of the modulation/reservoir system 825a in this manner achieves the advantageous reduction of introduction of unnecessary medium into the patient while achieving the necessary amount and flow of medium in the patient for the desired diagnostic or treatment process. Furthermore, the modulating/reservoir assembly may advantageously allow an operator to change out the injection delivery system (i.e., guide catheter, diagnostic catheter, treatment tools, etc.) without changing the flow modulator. Moreover, the diversion reservoir may allow simplistic re-use of the diverted medium.

Exemplary Modulation Devices and Methods with Synchronization

In addition to modulating injections by reducing inefficient agent use (as illustrated as areas A, B and/or C in exemplary injection profile $Q_{Agent}$ of FIG. 4B), modulation may also advantageously include delivering medium to a vessel in greater quantity when there is greater blood flow, and in lesser quantity when the blood flow is diminished. It is an objective of at least some embodiments described herein to pattern the injection of medium into a vessel to coincide roughly with the pattern of blood flow in that vessel. By way of example, FIG. 13 illustrates an exemplary injection profile delivered by an inventive injection system in which the injection profile coincides roughly with the blood flow within the vessel of FIG. 2. In this case, an average of about 2.8 ml/second of agent (e.g., average of $Q_{Agent}$) may be used to fill the vessel in sufficient quantity (e.g., to perform its opacification function) while not forcing the vessel to fully fill with agent, or otherwise displacing all of the normal blood flow. Thus, the dotted-line in FIG. 13 highlights the profile produced by the injection system in filling the vessel with medium of about 65% to 85% of the normal blood flow, for example. The amount needed for medium concentration (e.g., within in the blood) may vary depending on the agent and the intended function, and it is possible that such concentrations could be provided at as low as 1% of the blood flow rate and at as great as 99% of the blood flow rate without deviating from the intent of the modulation devices and methods described herein.

Synchronized delivery of agent may reduce the risk of "over-filling" the vessels outside of the target vasculature. In addition, such an injection flow rate profile may provide sufficient agent concentration within the vessel for opacification during lower flow. Over-injecting the coronary vasculature (for diagnostic or therapeutic purposes) may be seen arteriographically as "blow back" or reflux, and loads the body with unnecessary agent(s). Examples of synchronization embodiments may involve sensors and controllers utilized to modulate the injection of medium into the target site. Such sensors/controllers might include an EKG (and/or inputs from an EKG) to initiate activation and deactivation, or modulation, of an injector to deliver medium to a vessel as a function of the pulsatile flow of blood in the vessel. Other embodiments may include sensors positioned into, upon, and/or proximate, an injection delivery catheter so as to infer or deduce a parameter of blood flow (pressure, flow rate, temperature, velocity, patient respiration, pH, $pO_2$, etc.) in an effort to coordinate the injection of medium with the flow of blood in the vessel.

Although synchronized delivery will be further elucidated below, coordinating an injection of medium with the flow of blood in a vessel in a varied, or "pulsatile" fashion may not be the only means of using varied flow to reduce the amount of medium delivered to the patient, without compromising vascular opacity. Medium injection may also be reduced through pulsatile flow control methods/devices without synchronization. In this regard, pulsatile flow of medium may be generated by applying rapidly changing pressure (in amplitude over time) to drive a medium delivered to a patient. In this case, the peak amplitude of the pressure wave may be sufficient, or nearly sufficient, to achieve adequate opacity. In a sense, this may be akin to an electrical model of alternating current (AC) versus direct current (DC) in the application of medium to the patient. The pressure applied to the medium for the patient may be varied in amplitude over many cycles during each "pump" of the heart in a coronary artery application. The pressure may be "pulsed" in a variety of wave forms of design, such as: sinusoidal, symmetrical, and asymmetrical, as examples. As well as, the design of the wave may change and/or alternate in frequency, amplitude or wave size. As previously discussed, graphic illustrations of blood flow and injection agent flow have been illustrated relative to flow rates (e.g., FIGS. 2, 4A, 4B, 4C, 4D and 13). However, given the direct relationship of flow (Q) and pressure (P) in our model(s), graphical representation of pressure may also be utilized in characterizing injection medium modulation techniques. Optimization of delivery of medium (such as contrast agent) to a vascular delivery site may be enhanced by control of the medium injection pressure and flow rate.

Figure 44:
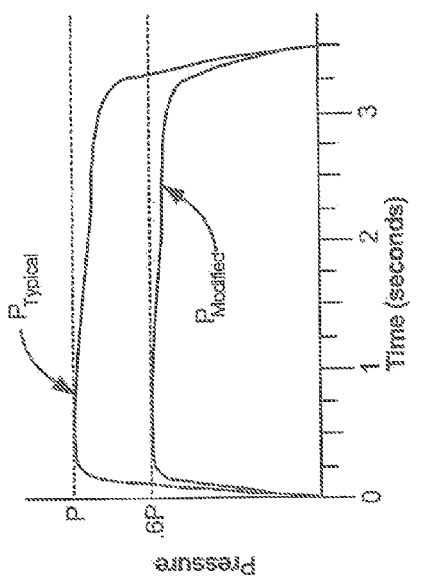
FIG. 44 illustrates graphically a typical injection profile (pressure) of agent with a treatment system of FIG. 3, and an injection profile (pressure) of agent for the treatment system of FIG. 3 as modulated using a variable force delivery platform such as illustrated in FIGS. 26-27.

FIG. 44 illustrates an example of a medium injection pressure profile that may be found within a left main coronary artery of a human heart—this may be a typical profile of injection pressure $P_{Typical}$ illustrating an injection profile made by a doctor with a syringe extending over approximately 3.5 seconds, without any modulization modification pursuant to the disclosure herein. This profile may be similar to the injection profile illustrated in FIG. 4A; however, FIG. 44 graphically represents a pressure (P) profile, whereas FIG. 4A depicts a flow rate (Q), over time. FIG. 44 also illustrates an exemplary medium injection pressure profile $P_{Modified}$ for a medium injection using a modulation system such as disclosed herein by modulation system 325 including a variable force delivery platform 402 (such as illustrated in FIGS. 26-27). As seen in FIG. 44, the peak injection pressure along the modulation pressure profile $P_{Modified}$ may be 60 percent less than the typical peak injection pressure without modulation.

Figure 46:
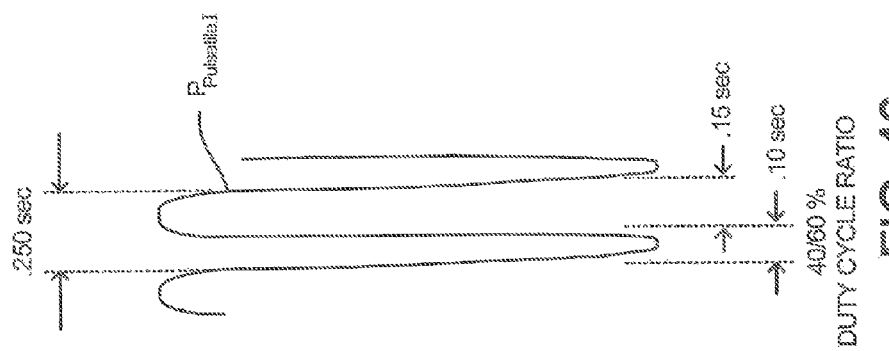
FIG. 46 illustrates an enlarged view a segment of the pulsed injection profile $P_{Pulsatile\ I}$ of FIG. 45.
Figure 45:
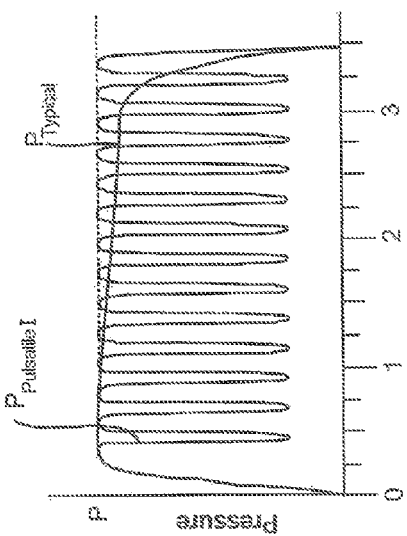
FIG. 45 illustrates graphically an injection profile (pressure) of agent for the treatment system of FIG. 3 in a typical injection ($P_{Typical}$) and a pulsed medium injection profile ($P_{Pulsatile\ I}$).

FIG. 45 illustrates an exemplary pulsatile medium injection profile $P_{Pulsatile\ I}$, again over a typical 3.5 second injection of medium into a patient. The medium injection profile $P_{Pulsatile\ I}$ of FIG. 45 may allow the attainment of full pressure of a typical injection to be realized, but do so at spaced intervals of medium pressurization. In the example illustrated in FIG. 45, the "duty cycle" (time between waves) for the pulsatile pressure profile $P_{Pulsatile\ I}$ may be 0.25 seconds. This is more fully illustrated in FIG. 46, which is an enlarged segment of a portion of the pressure profile $P_{Pulsatile\ I}$. In FIG. 46, the portion of each 0.25 second duty cycle where pressure is applied to attain the peak pressure is 0.15 seconds, whereas the portion of each duty cycle where the pressure is not applied at peak is 0.10 seconds, resulting in a 60% "on"/40% "off" pressurization duty cycle, as an example of pulsatile injection. It is clear that there are a variety of wave shapes, peaks, troughs, duty cycles, etc. that one may use to accomplish a reduction in medium injection without compromising function (e.g., opacification). This is merely one example in the use of a pulsatile injection to modulate the delivery of a medium.

Figure 49:
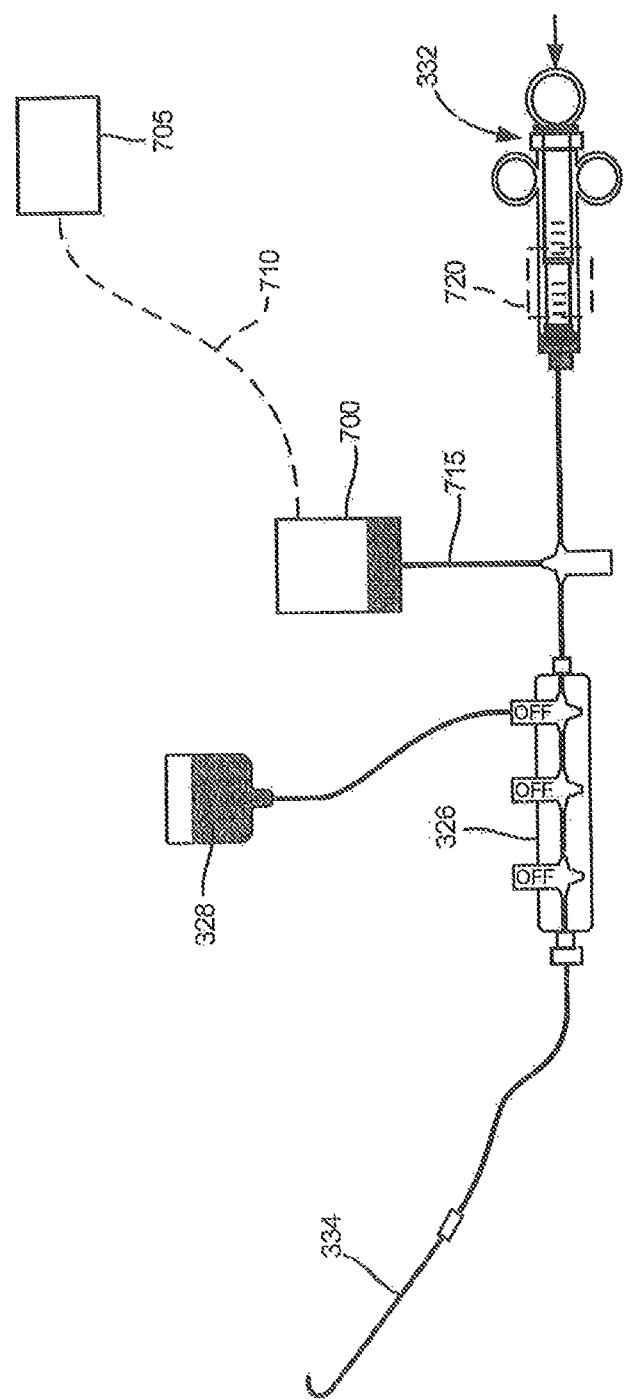
FIG. 49 illustrates an exemplary arrangement for indirect application of pulsed pressure to medium being manually injected via a catheter.

FIGS. 47 and 48 illustrate an alternative medium injection pressure profile $P_{Pulsatile\ II}$ that illustrates an injection pressure profile similar to FIG. 45 but using a different duty cycle for the pulsed medium pressurization. In this case, the duty cycle is 0.125 seconds, resulting in a higher frequency of pulsation but still attaining a pressure P about that of a typical injection $P_{Typical}$. FIG. 48 illustrates an enlarged view, showing the exemplary 60/40 duty cycle ratio between peaks and valleys of the pulsed flow profile $P_{Pulsatile\ II}$. Establishing a pulsatile pressure profile for a medium injection (such as profiles $P_{Pulsatile\ I}$ or $P_{Pulsatile\ II}$) may not depend on the peak pressure being applied (such as pressure P in FIGS. 44, 45 and 47). Pulsation of medium injection pressure could be applied to the medium at any desired pressure so as to reduce the reduce the amount of medium injected without opacity compromise As discussed above with alternative embodiments, modulation of medium delivery to a patient may be achieved in parallel, or in series. FIG. 49 illustrates schematically an arrangement whereby pulsatile medium pressure modulation may be achieved in a "parallel" arrangement (whereby the catheter 334 provides one level of medium flow resistance, and a flow diverter assembly which may include a medium reservoir 700 may, in combination with other diverter elements such as those described above, provide a second resistance to medium flow between the syringe 332 and the catheter 334). One means for modulating the pressure at the catheter is to modulate the bleed off medium pressure via manipulation of reservoir 700. In effect, this is achieved by creating a negative pulse on the diverted flow path, like employing a variable resistor thereon. This may be done, for example, by modulating the volume in the reservoir 700, such as by means of a movable piston, solenoid or membrane, which then has the consequence of changing the frequency of medium pressure applied to the patient via the catheter 334. The volume in the reservoir 700 may be modulated by mechanical forces created by mechanical devices, thereby creating waves or pulses on the medium in the reservoir 700. Such devices can be controlled by a controller 705 coupled to the reservoir 700, either wired or wirelessly via control connection 710. The controller 705 may be located outside the sterile surgical field relative to the patient. Alternatively, a mechanical device may be, by design, formed to define a pulsatile action on the medium in the reservoir 700 without requiring a controller 705. The pulsing of the diverted medium flow in an arrangement such as illustrated in FIG. 49 may be attained by modulating the volume in the reservoir 700, or also by opening and closing a diverter flow path 715 extending between the reservoir and the main flow path between the syringe 332 and the catheter 334. In either instance, using mechanical or controller driven means to achieve such pulsatile activity relative to the medium in the diverted portion of the medium flow results in likewise reduced medium flow to the patient via the catheter 334, as illustrated again by the exemplary medium pressure profiles $P_{Pulsatile\ I}$ (FIG. 45) and $P_{Pulsatile\ II}$ (FIG. 47). Although these examples describe two ways of achieving a "pulsatile" pressure, there are a myriad of means to effect similar waves and these are not outside the scope of this disclosure.

Moreover, with pulsatile forces acting on a medium in the diverted portion of the medium flow path, the syringe operator may not necessarily feel the immediate effects of such pulsation (i.e., by tactile sensation when manually manipulating the syringe). To the operator, the manipulation of the syringe may not feel or function any differently than a typical medium injection pressure profile, such as illustrated $P_{Typical}$ in FIGS. 44, 45 and 47.

As noted above, the pressure profile for medium applied to the patient via the catheter 334 may also be achieved by a pulsatile effect applied to the medium directly (i.e., in series with medium flow to the catheter 334). In this example, a pulsatile generator 720 may be disposed along the medium flow line extending between the syringe 332 and the catheter 334. The pulsatile generator 720 may be designed to create a positive pulse on the medium flowing therethrough to the catheter 334 in order to vary the pressure of the medium to follow a medium pressure profile, such as illustrated by profile $P_{Pulsatile\ I}$ (FIG. 45) or $P_{Pulsatile\ II}$ (FIG. 47). Pulsing of pressure on the medium by the pulsatile generator 720 may be achieved by repetitive pinching of a medium flow line passing through or adjacent, the pulsatile generator 720, or by other suitable mechanical flow pulsing means. Alternatively, the pulsatile generator 720 may be incorporated directly into the syringe 332 so that the fluid flow exiting the syringe 332 is already being delivered in a pulsed state relative to its pressure profile. In either case, the pulsatile generator (whether in line or incorporated into or adjacent the syringe), may be controlled by a controller 705 disposed outside of the sterile surgical field. The controller 705 may be coupled, either wired or wirelessly, via control connection 710 to the pulsatile generator 720, whether the generator is disposed in line or in the syringe 332. It is also conceivable that the pulsatile generator 720 acts independently of any controller.

In many cases of pulsatile flow of medium, the objective is to reduce the amount of medium delivered to the patient, yet still provide sufficient medium to achieve operative function. In the case of contrast delivery, functionality may be determined through opacification of the vasculature upon injection. The advantage of employing a pulsed medium pressure profile such as those illustrated in FIGS. 45 and 47 is that the volume of medium necessary for achieving opacity may be reduced. Also, medium modulation via medium pressure/flow pulsation may not be dependent on the size or form of catheter configurations being deployed in the patient, and thus may provide the ability to further reduce the introduction of excess medium across all such catheter configurations and procedures. Furthermore, the effect of "pulsating" the flow of medium delivered to a site may provide better "mixing" of agent with the blood and this action, in and of itself, may reduce medium use similar to the "mixing" effect described by the device in FIG. 18

Figure 14:
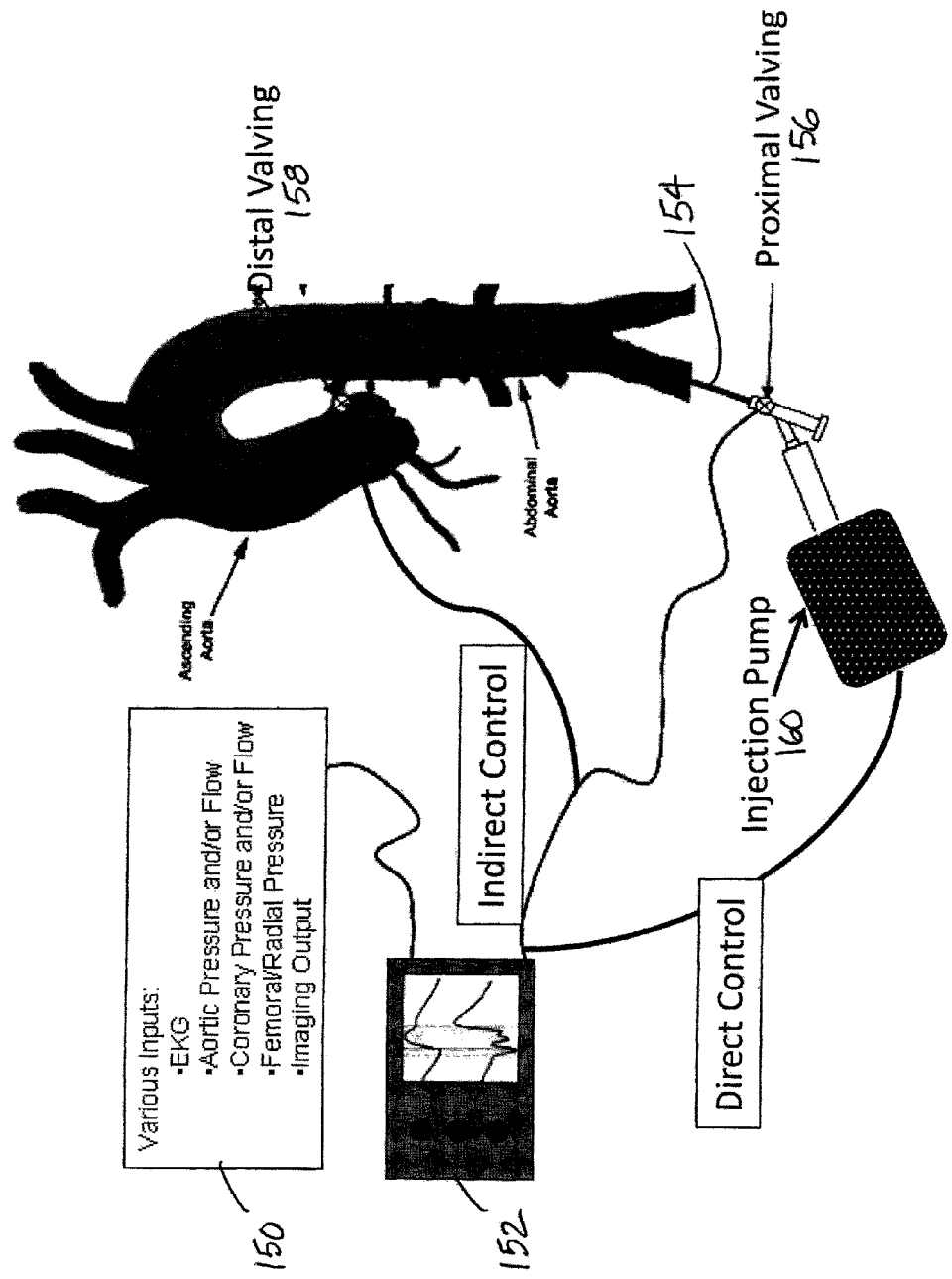
FIG. 14 illustrates exemplary schemas of synchronized agent delivery modulation systems.

Continuing with "synchronizing" an injection with the flow of blood in a vessel, FIG. 14 illustrates exemplary schemas for a synchronized medium injection modulation system. As shown, one or more signal sensors 150 may each receive a signal representing, deducing, or inferring, the status of at least one parameter of flow at the target injection site such as the left coronary arteries of the heart. A controller 152 may receive the signal(s) from the sensor(s) 150 and then directly, or indirectly, activate modulated delivery of medium though the delivery catheter system 154. As can be seen in FIG. 14, valving (or otherwise modulating mechanisms) may be positioned near the proximal portion of the delivery system 154 (e.g., in proximity of the delivery catheter proximal portion, outside of the body, as at proximal valving 156), and/or may be placed in, around, and/or in proximity of the distal portion of the delivery catheter (e.g., inside of the body, as at distal valving 158), with such valving being actuated by the controller 152. Further, one or more of the sensor signals may be from a sensor located externally of the body such as an EKG, and/or one or more of the sensor signals may be derived from a sensor within the body (such as a pressure sensor placed in, about and/or in proximity to the distal portion of the catheter).

Figure 15:
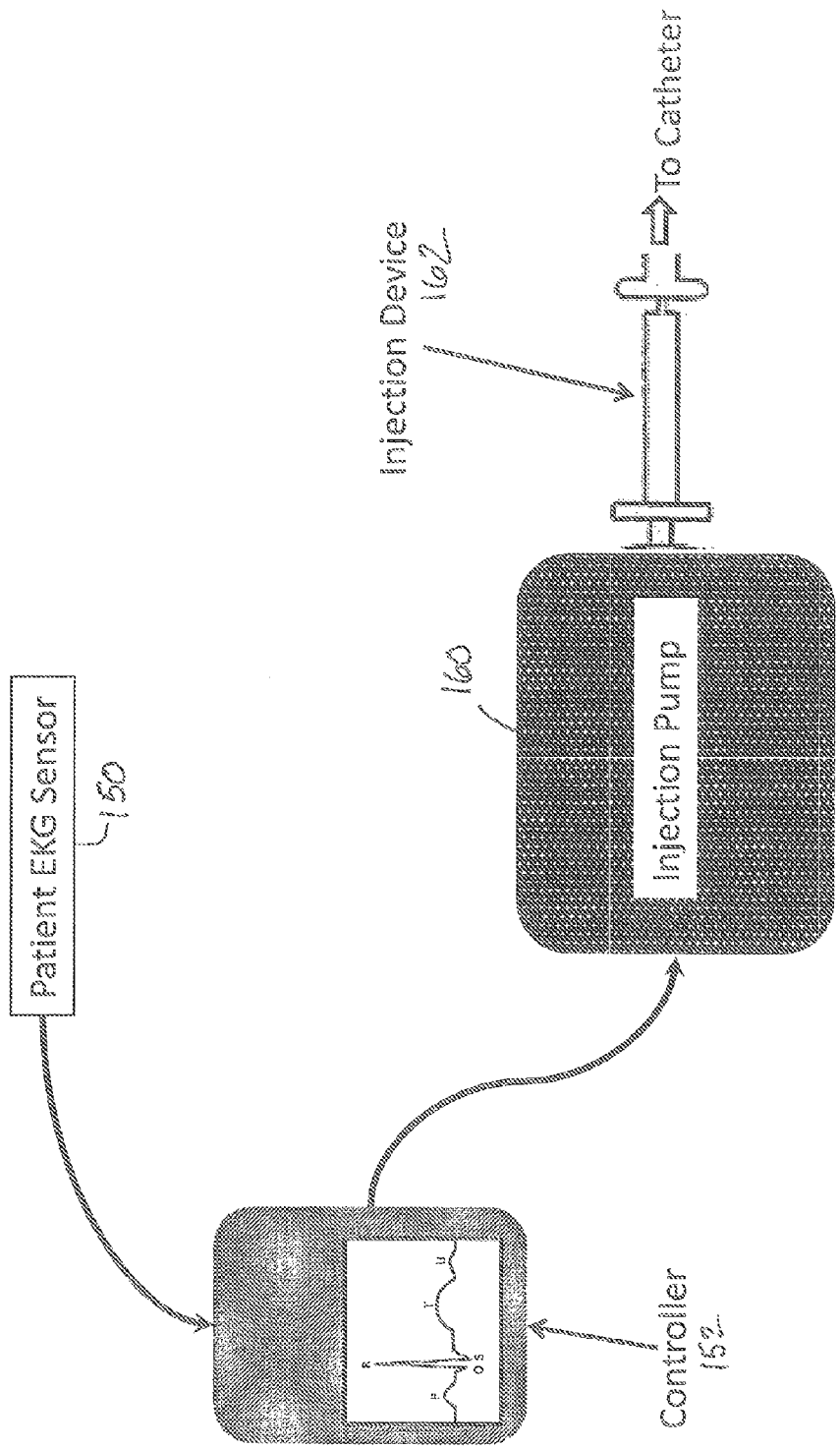
FIG. 15 illustrates an exemplary synchronized agent delivery with direct modulation.

Direct control of modulation may include, for example, activating the injection device directly to synchronize dispensing of medium through the injection delivery catheter to produce the injection flow rate (e.g., $Q_{Agent}$) profile as shown in exemplary FIG. 13. In this example, a signal from a sensor 150 (such as, for example, an EKG signal) is used by the controller 152 to directly actuate the injector pump 160 so as to increase/decrease the injector output to produce a medium agent injection flow rate (e.g., $Q_{Agent}$) profile as shown in FIG. 13. An example of such a system may be found in FIG. 15. As can be seen, an EKG signal of the patient's heart rate is received from an EKG sensor 150 by the controller 152. The controller 152 may selectively signal a start for increasing flow rate at some time interval after the QRS complex of the EKG, and a start for decreasing flow delivery before and/or during the QRS complex, for example. Thus, the controller 152 of FIG. 15 may then activate/deactivate the pump 160 operably coupled to injector 162 to varying degrees to provide dispensing of medium from the injector 162 when an operator has signaled to the controller 152 that an injection is warranted. The activation/deactivation of the injector pump 160 may be capable of producing an exemplary injection profile ($Q_{Agent}$) as described by FIG. 13.

Figure 16B:
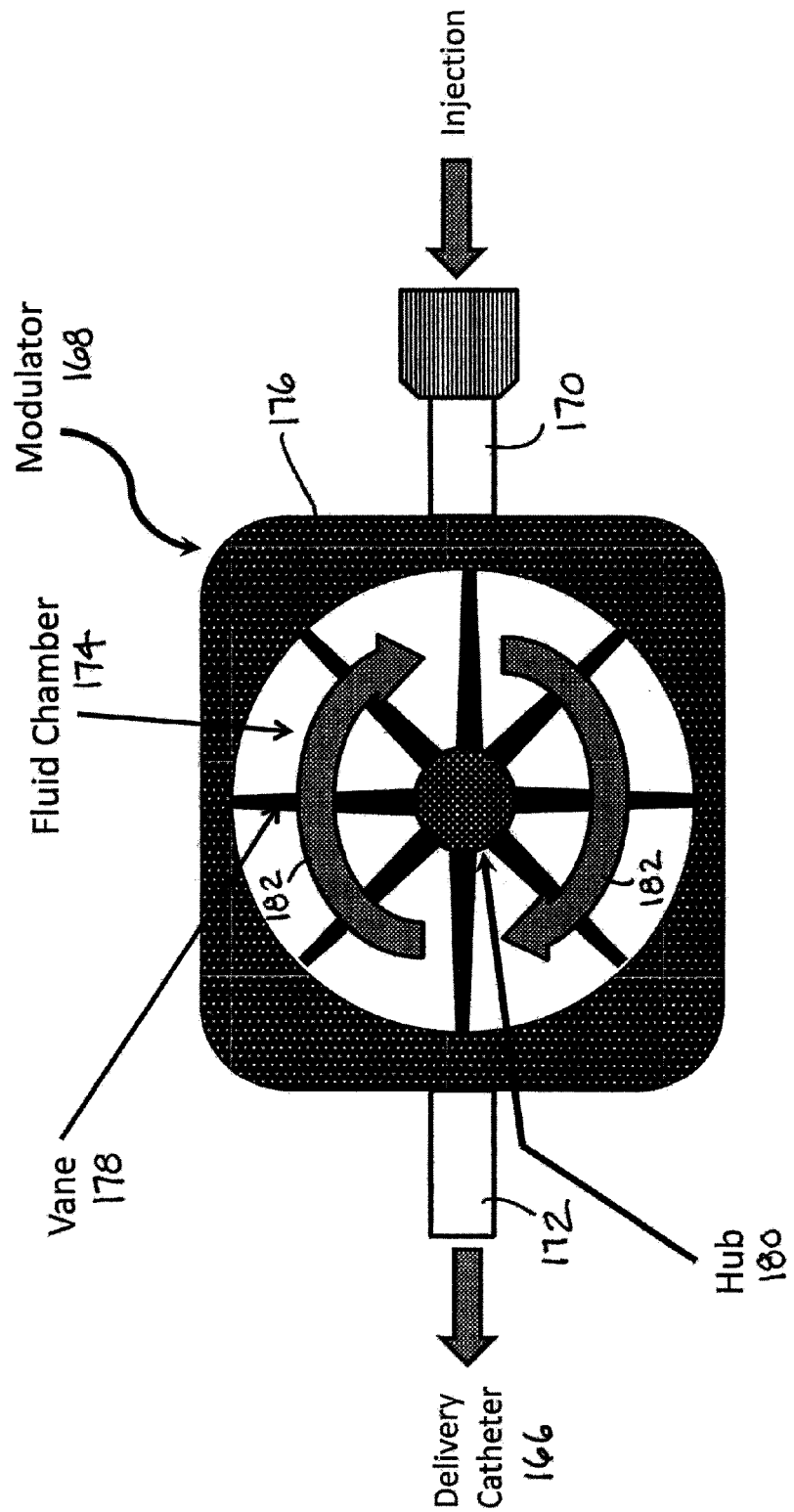
FIG. 16B illustrates an exemplary synchronized agent delivery with indirect modulation (top view), adjacent a proximal portion of such a treatment system.

Indirect control of modulation may include, for example, valving (or otherwise modulating) an injection dispensed from an injection device. As described previously in the various schemas of FIG. 14, indirect valving (or otherwise controlling mechanisms) may be proximally or distally positioned within, about, and/or upon the agent delivery system 154. An example of an indirect modulation control may be found in FIGS. 16A-16D. In this example, a sensor 165 is deployed distally on a delivery catheter 166 (as seen in FIG. 16A) and a modulating device (of FIG. 16B) is provided proximally (i.e., positioned proximally as shown for modulator 168 of FIG. 16C, for example). The sensor 165 of FIG. 16A is an exemplary pressure sensor positioned on the distal tip of the delivery catheter 166. As described previously, this is only one example of the various sensors that may be used in obtaining a signal to synchronize the delivery of medium with the blood flow rate. Moreover, FIG. 16A illustrates the positioning of the sensor 165 upon the distal tip of the delivery catheter 166. The exemplary positioning of the sensor 165 in FIG. 16A should not be limited to that shown in order to perform the functions described herein, since there may be a multitude of sensor types (and commensurate signals) positioned at various locations on (i.e., as a function of respiration), through (i.e., as a function of imaging) and within the body (i.e., as a function of a variable proximate a target delivery site). Clearly, even the placement of a distal pressure sensor in exemplary FIG. 16A could take many forms, such as: a pressure wire alongside the catheter; a lumen within the catheter body for pressure measurement; a pressure sensor deployed within the distal tip of the catheter; a pressure sensor deployed distally of the distal tip of the catheter and into the target vessel, to name but a few.

Referring to FIG. 16B, modulating device 168 may comprise an inlet port 170 (from the injection device) and an outlet port 172 (to the delivery catheter 166). The flow of injection fluid may pass through the injection port 170 and into a fluid chamber 174 within a body or housing 176 of the modulator 168. The modulator 168 may have a plurality of vane/plates 178 attached to a cylindrical hub 180 disposed within the fluid chamber 174. The vanes 178 and hub 180 may be formed to define a "pinwheel" structure of vane-hub that is capable of rotating freely (relative to fluid chamber 174 and body 176 of modulator 168) upon the injection of medium into the fluid chamber 174 through the injection port 170. The hub 180 may be designed to preferentially rotate in one direction. For example, FIG. 16B illustrates the preferential flow of fluid and rotation of the vane-hub, in a clockwise direction, via flow arrows 182. From the fluid chamber 174, injection fluid may flow out of the modulator 168 via the outlet port 172.

One advantage of a vane-hub modulator design of this type is that it may be easy to measure, or otherwise identify, the total volume of injection fluid delivered through the modulating device 168 (over time) since the volume of fluid passing through the device 168 during one rotation of the vane/hub may be easily determined, and the number of rotations simply counted by a counting mechanism. Alternatively, each "cell" of fluid between adjacent vanes 178 may be readily counted by a counting mechanism. The counting mechanism is not shown in the illustrations, but it may comprise a magnetic, mechanical, ultrasonic, infrared or similar measurement device capable of identifying the number of times a vane 178 and/or some other element of the vane-hub has passed within its field of measurement, or by determining the number of times the axis of the hub 180 has rotated. The output of such a counting device may be utilized to determine and display (in real-time) the total volume of medium used during a procedure. Advantageously, in the management of medium injected, an operator/physician may readily see the amount of medium used (as determined by the counting device and presented by a suitable display or indicative output). The determination of the volume (via calculations/conversions based on, for example, counted rotations) may be performed as part of the counting device, or may be performed by a display device. In addition to providing volume measurements, the counting mechanism/signal/display may incorporate various algorithms to alert an operator/physician before, or at a point which, a maximum volume of agent has been administered (i.e., operator determined value, Maximum Acceptable Contrast Dose, GURM ratio, etc.).

Figures 16C, 16D:
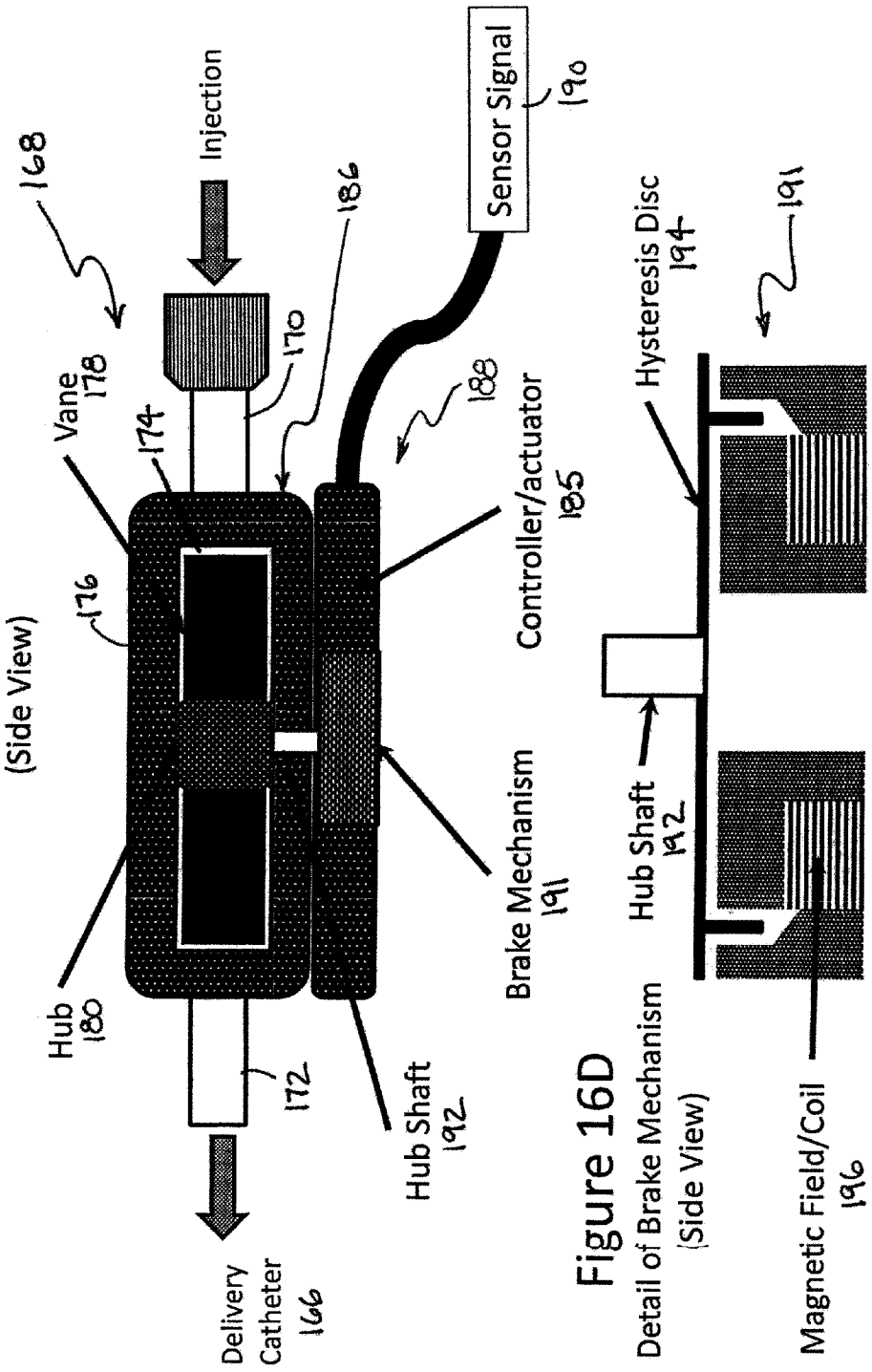
FIG. 16C illustrates an exemplary synchronized agent delivery with indirect modulation (side view), adjacent a proximal portion of such a treatment system.
FIG. 16D illustrates, in side sectional view, the brake mechanism of the exemplary synchronized agent delivery arrangement of FIG. 16C.

Continuing with the description of the exemplary modulation device 168 shown in FIGS. 16B-16C, a vane-hub modulator may comprise two components. One component 186 may be situated adjacent a controller/actuator 185 and may comprise the input port 170, the output port 172 and the fluid chamber 174 with rotating vane/hub 178/180. This component of the system, which may come into contact with fluids, may be disposable if so desired. A second component 188 comprising the controller/actuator 185, brake mechanism 191, sensor signal 190 receiver, and the like may be used to clutch, brake, or otherwise inhibit the rotation of the vane-hub so as to provide resistance to rotation. The resistance induced to the rotation may be coordinated with a signal 190 from sensor 165 of FIG. 16A, so as to modulate an injection from an injector to produce an agent fluid flow ($Q_{Agent}$) profile as described, for example, in FIG. 13.

The braking, or clutching of the modulator 168 of FIG. 16C may be performed through a variety of means, to include, for example, mechanical, hydromechanical, electromechanical, electromagnetic, chemomechanical, etc.

FIG. 16C illustrates one such means 191 for braking the shaft 192 of the vane-hub, using electromagnetic means. The exemplary braking structure 191 is further detailed in FIG. 16D, wherein the longitudinal shaft 192 of the hub 180 is coupled to a hysteresis plate/disc 194 positioned within a magnetic field 196. When electricity is applied to the magnetic coil 196, a magnetic flux is transferred to the hysteresis disk 194 (as it passes through the field) causing a magnetic "drag" on the disc 194. The drag, or braking, applied to the hysteresis plate 194 (and thus the shaft 192 of the vane-hub) may be increased/decreased with increasing/decreasing voltage applied to the magnetic field to modulate the flow of medium as intended. When electrical current is removed, the connected disc/shaft may rotate freely about an axis of shaft 192. In the example of FIG. 13, the maximum flow rate of agent ($Q_{Agent}$) is approximately 5.2 ml/second. Therefore, in producing profile of $Q_{Agent}$ of FIG. 13, one might set the injection of medium into the modulator 168 at a constant rate of 5.2 ml/second. Upon modulating, braking mechanism 191 of FIG. 16D may increase the drag (reduce the flow rate) of the agent as needed to produce the flow profile of $Q_{Agent}$ of FIG. 13.

FIGS. 16B and 16C describe one of numerous means to regulate the flow profile of injection agent thru a modulator, and as such, are intended to illustrate the modulation monitoring and control concepts disclosed herein without limitation. Of course, such means may be employed with various signals and sensors (such as shown in FIG. 16A) to "synchronize" the flow of injection medium with corporeal medium flow. Therefore, the example of FIG. 16 is but one example how one might use a modulator device to perform synchronization.

Previous embodiments of "synchronized" delivery described herein may include active sensing and subsequent modulating of the delivery of a medium. However, delivery of a medium to a delivery site may be also modulated by passively valving the medium delivery as a function of a physical attribute in and/or around the delivery site; such as pressure, for example. Referring to FIG. 23, a delivery catheter 260 may be placed to deliver a medium to a delivery site, such as the left main 24 of the coronary vasculature. In this setting, there are continuously changing pressures within the left main 24 as well as the aorta 22, as previously described. A valving mechanism 262 may be deployed within, on or in proximity of the distal portion of the delivery catheter 260.

FIGS. 24A and 24B illustrate in more detail the distal portion of the catheter 260 with a passive valving mechanism 262 present. As shown in FIGS. 24A and 24B, the valving mechanism may include a blood flow bypass lumen 264, allowing some blood flow alongside medium delivery lumen 266 of the catheter 260. A passive valve gate 268 is disposed to limit blood flow through bypass lumen 264 and medium flow through medium lumen 266, as a function of pressure differential around the delivery site. As shown in the FIG. 24A, when the pressure within the left main 24 (e.g., $P_{LM}$) is less than the pressure in the aorta 22 (e.g., $P_{AO}$), the valve gate 268 of delivery catheter 260 may allow the injection of medium to the delivery site (as illustrated by medium flow arrows **269*a* in FIG. 24A). Conversely, as shown in FIG. 24B, as the pressure differential between the left main 24 and the aorta changes 22, with the left main 24 increasing in pressure with respect to the aorta 22 (e.g., slowing of blood flow into the left main 24), the passive valve gate 268 may act to hinder, or reduce, the delivery of medium to the delivery site (as illustrated by the medium flow arrow 269*b* in FIG. 24B). Thus, the device of FIGS. 23, 24A and 24**B provides an arrangement that may allow "synchronized" delivery of medium to the coronary vasculature as a function of a passive valve mechanism.

FIGS. 25A and 25B illustrate another embodiment of passively valving the distal portion of a catheter so as to improve the efficiency of delivery of medium to a delivery site. FIG. 25A illustrates a delivery catheter 270 that may be placed in a sealing relationship (partial or total) with a coronary artery 25 such as, for example, as at catheter/artery interface 272. With such use, there may be a concern that blood flow from the aorta 22 is restricted from perfusing the occluded artery 25. However, as shown in FIG. 25A, distal portion of delivery catheter 270 may have a valve 274 and orifice(s) 276 disposed distally of the valve 274 so as to provide perfusion from the aorta 22, through the catheter 270, and distal to the delivery catheter (i.e., into the artery 25) when medium injection is not taking place. In this instance, valve 274 is closed, allowing blood to flow into orifice(s) 276, through the distal portion of the catheter 270, and past the catheter/artery interface 272. The valve 274 thus acts to allow blood flow distally, as illustrated by blood flow arrows 278 in FIG. 25A (while inhibiting the flow of medium past valve 274). Conversely, as shown in FIG. 25B, when delivery of medium is warranted, valve 274 may be deployed so as to reduce perfusion from the aorta 22 and allow medium delivery to the delivery site. In this instance, valve 274 is open, allowing medium to flow past valve 274, through the distal portion of the catheter 270, and past the coronary/artery interface 272. The valve 274 thus acts to allow medium flow distally, as illustrated by medium flow arrows 279 in FIG. 25B (while inhibiting the flow of blood past valve 274).

There are many forms wherein the passive distal valving of a delivery catheter may be employed to further enhance the efficiency and/or effectiveness of medium delivery to a delivery site. The previous examples are illustrative of the inventions, and should not be interpreted as limiting in their scope.

In addition to the various embodiments described herein to effect more efficient delivery of medium to a target site, the modulation of an injection may be further enhanced with various delivery catheter tip configurations, thus advantageously changing the flow characteristics in, around and/or proximate the delivery site. For example, FIGS. 17A-17D illustrate four embodiments that may be employed to perform such a function. As previously described by FIGS. 5A and 5B, it is clear that at least one of the challenges associated with the delivery of medium may involve the location of the delivery catheter tip and the pressure differentials surrounding the tip. FIGS. 5A and 5B illustrate a catheter delivery tip within the aorta 22, at the ostium 20 to the left main 24. This "catheter tip" placement may be common since physicians may be hesitant in delivering the tip of the catheter into the left main due to concerns of injuring/disrupting the vessel wall and/or causing spasms (and thus acute occlusion) within the left arterial system. If the delivery catheter is positioned as such, there may be little "driving force" (e.g., pressure differential) to preferentially deliver the medium from the delivery catheter tip into the ostium, versus into the aorta (and, thus systemically). FIGS. 17A-17D show various embodiments that may preferentially modulate the environment surrounding and/or proximate the delivery catheter tip in order to enhance the delivery of agent into the ostium. In many regards, these embodiments may also act to isolate/control the environment surrounding the delivery catheter distal delivery portion so as to accommodate more efficient delivery of a substance.

For example, FIG. 17A illustrates a delivery device 210 that may have a balloon inflated around its distal portion 212 so as to increase the pressure within the aorta 22 (at least during injection), and further "drive" the injection medium into the ostium 20. The embodiment of FIG. 17B illustrates a conical member 222, surrounding the catheter delivery tip of delivery device 220, which may act to capture/isolate medium, and/or increase flow resistance (when deployed) for the medium to flow to the aorta 22; and thus, preferentially "drive" the medium into the left main 24. $P_{AO}$ and $P_{LM}$ of FIG. 17B designate areas of pressure within the aorta (e.g. $P_{AO}$) and the left main (e.g., $P_{LM}$) solely for the purpose of identification. The conical member 222 may also be expandable; as well as the expansion of 222 could further be in response to the pressure gradient between $P_{AO}$ and $P_{LM}$.

The alternative exemplary embodiment described by FIG. 17C shows a delivery device 230 that includes a coaxial member or sleeve 232 surrounding a distal catheter delivery portion 234 and may, in essence, act to artificially "extend" the left main 24 into the aorta 22. Thus, upon injection of medium, the flow of the medium is subjected to greater resistance to flow along the path to the aorta 22 (via the sleeve 232) than would be present flowing to the ostium 20. In some ways, the coaxial nature of the coaxial 232 member may also advantageously function as a distal "reservoir" of medium, acting to store and then release medium from the temporary reservoir structure in response to the cyclical pressure changes seen, for example, by the left main 24.

FIG. 17D illustrates another embodiment in the modulation of the flow parameters surrounding the delivery catheter distal portion. As shown, a delivery device 240 has a delivery catheter tip with a coaxially expandable sheath 242 surrounding a distal portion of the catheter. When expanded, the sheath 242 could partially engage the ostium 20, as at 244 for example. The expansion of the sheath 242 may be actuated by the flow of injected medium through at least one or more orifices 246 along the distal portion of the catheter. The expanded sheath 242, when deployed, may create greater resistance to flow (for agent) along the path to the opening 20 of the aorta 22, than along the path into the left main 24, as indicated by the flow arrows in FIG. 17D.

There are many variations to the structures and configurations exemplified in FIGS. 17A-17D which may modulate, or otherwise control or isolate, the pressure and/or flow environment surrounding a distal portion of the delivery catheter. FIGS. 17A-17D are illustrative of embodiments that advantageously modulate the flow characteristics in, around and/or proximate the delivery site and, as such, should not be viewed as limiting the scope of the structures and methods for achieving such flow characteristics.

In addition to the various disclosed arrangements and processes that may act to modulate the environ of flow characteristics in, around and/or proximate the delivery site, other delivery catheter distal tip designs might advantageously "mix" the medium with the blood. The applicants have found that in at least some medium delivery scenarios (i.e., agent, target site, flow parameters) it may be necessary for the injected medium to travel a distance from the distal tip of the catheter before the medium may be sufficiently "mixed" with the blood flow (e.g., homogenous concentration of the medium within the blood). In the example described by FIGS. 5A and 5B, it is possible that an injected agent may not reach a homogenous concentration within the blood flow for some distance distally along the left main and/or arterial supply from the ostium. As an example, if it were to take approximately 2 cm to 3 cm for the medium to mix with the blood, then this distance along the vessel may not be "well opacified." In this situation, an operator of an injector may continue to increase the medium delivery in order to obtain greater opacification of the vessel. A delivery catheter having a distal tip construction as shown, for example, in FIG. 18 may be able to more readily mix the medium exiting the catheter with the blood flowing by the catheter, and therefore may advantageously reduce the amount of medium necessary to see the opacification of the artery.

Figure 18:
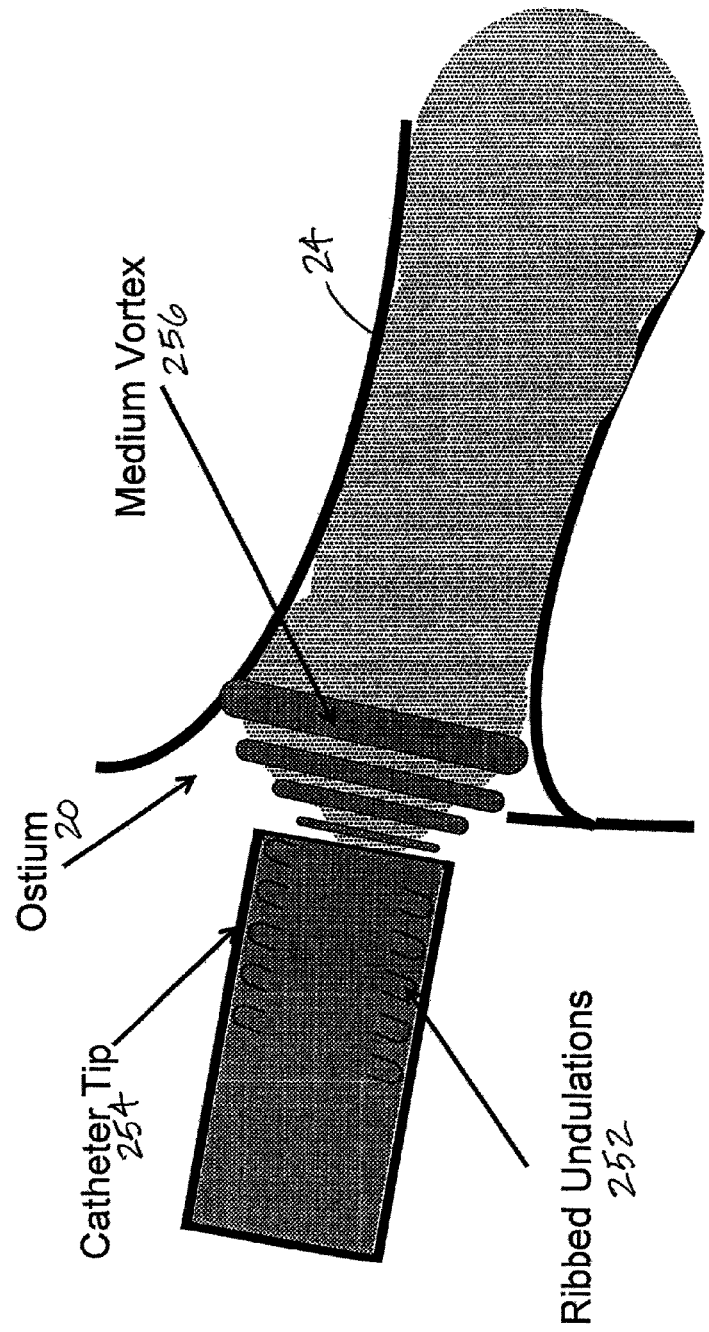
FIG. 18 illustrates an exemplary delivery catheter with distal disrupting structure.

The example of FIG. 18 shows a delivery catheter 250 having ribbed undulations 252 along the inner surface of its distal tip 254 so as to provide a flow pattern resembling a vortex 256 of the medium exiting the catheter 250. The disrupted medium flow pattern may more readily mix the medium and blood. Although FIG. 18 illustrates ribbed undulations along the inner surface of the delivery catheter, it is clear that there may be other structures and configurations that may perform the same function (such as: structures along the inner and/or outer diameters of the delivery catheter; structures deployed within the blood, distal to the catheter tip, to agitate/disrupt the blood/medium flow; structures such as orifices placed along the distal portion of the catheter to allow medium/blood mixing within the delivery catheter; etc.). In connection with the notion of mixing the medium and blood, FIG. 18 is only intended to illustrate an exemplary arrangement and process for doing so.

Note that "tip" of the catheter as used may be synonymous with the "distal portion," or any other portion of the catheter that may reside within the patient's body (e.g., distal of the proximal portion of the delivery catheter) and might play a role in the delivery of an agent to an intended target site.

In summarizing many of the embodiments described herein, there are numerous occasions in the diagnostic, prophylactic and treatment practice of medicine wherein an agent, substance, material, medicant, or medium is preferably delivered to a specific site within the body. Some of the examples described herein have advantageously comprised delivery control attributes that may derived from one or more of the modulating elements/functions illustrated in FIG. 19 (i.e., injection device type, regulation type, sequential versus direct delivery, synchronization with corporeal flow, activation/deactivation at pump versus after pump, flow environ manipulation). FIG. 19 attempts to summarize some of the described elements/functions with reference to illustrative FIGS. of this disclosure and/or their descriptions. As importantly, the various elements/functions in media delivery modulation are not, per se, mutually exclusive since one or more of these elements/functions may be used in combination to derive control attributes desired. As such, the various elements/functions identified in FIG. 19 may be selected (e.g., "mix-and-matched") to produce a modulator that optimally performs an intended purpose. For example, one might consider a variety of attributes in performance of medium modulating function, such as: target site location, target site access, fluid dynamics proximate the target site, agent to be delivered (e.g., quantity, viscosity, toxicity), injection frequency, concentration of agent within target site, target site isolation, ease of use of modulator, complexity in administration, cost of the system, and cost of agent, to name a few.

FIG. 19 can be considered a general summary for guiding the reader in identifying an exemplary function/element. Therefore, FIG. 19 is not, per se, inclusive of all the figures and descriptions within this disclosure that may contain a particular function/element; nor, is FIG. 19 inclusive of all embodiments disclosed herein. It is contemplated that the disclosed features, systems and schemes for modulation may be combined in a myriad of combinations and sub combinations to achieve operative introduction of medium (e.g., opacity) without excessive introduction thereof, in addition to those specifically shown and described.

Many of the examples of systems illustrated have involved the delivery of a cardiovascular contrast agent. However, there are many other applications wherein the controlled delivery of a substance to a specific structure/organ/site of the body may also benefit from the devices and methods disclosed herein. Due to the variety of medical applications, as well as the diversity of means to modulate (for example, elements/functions of FIG. 19) there may be a multitude of mechanisms employed to produce a modulator for its unique and intended purpose. An example of how one might go about employing various elements/functions in the construction of a modulator device is further described below, as it pertains to a non-cardiovascular procedure of lymphography.

Lymphography employs the delivery of an imaging agent to the lymphatic system wherein an agent is injected, and subsequently radiograph(s) taken, in the visualization of metastatic cancer cells. Procedurally (and after identifying the lymphatic), a needle/catheter may be inserted into a lymphatic channel/vessel in the foot (near the base of the first metatarsal) and a contrast medium (such as Ethiodol) may injected into the body at a very slow rate (approximately 60 to 90 minutes). The total quantity of injection might be 6-7 ml. The patient typically remains on his or her back during the procedure. Once the injection is complete, radiographs may be taken. Of note, the "flow" of fluid in the lymphatic system is consistently slow, as compared to the high flow and variability of the coronary arteries. Moreover, the lymphatic channel/vessels may be very sensitive (e.g., rupture) to over-pressurization.

Given the description of the lymphatic example (and referring to FIG. 19), one might construct a modulator with elements/functions that satisfy the following attributes: long delivery time; small volume delivered; constant flow rate; sensitivity to over-pressurization; sufficiently portable/movable to accommodate patient during the delivery; and, equal to or less expensive than using an automated injector. Given these attributes one might consider a manually-loaded injector device to deliver the medium sequentially (delayed) wherein the device may be filled with an amount of fluid to be delivered (e.g., 6 ml) first, and upon release of the injection, may deliver the medium over an extended period of time (e.g., 90 minutes). An element in regulation might include a device with constant flow rate (i.e., constant flow rate irrespective of variable pressures), or a regulator element that functions with constant pressure differentials (i.e., irrespective of variable flow rates). Because of the high sensitivity to pressures in the lymphatic, the latter alternative might be more amenable in accommodating high pressure "spikes" (for example, if the delivery catheter were to occlude during the delivery). Viewing FIG. 19, elements of corporeal flow synchronization, flow activation (via signal), and distal environ alternation may be less important, and therefore those features may not be included in the exemplary device construction. Ultimately, a multi-component, sequential delivery device as illustrated and described in FIGS. 9A-9C may simply modulate the delivery of a controlled amount of agent, without the risk of rupturing the lymphatic channels/vessels due to over-pressurization. The sequential delivery allows for filling a precise amount of fluid to be delivered, and once the lymphatic vessel is accessed, may continue to deliver the medium over time.

Clearly, the lymphatic medium delivery is but one additional, non-cardiovascular example and it is intended to help further illustrate how the various elements and components disclosed herein may be used in a variety of ways to satisfy a multitude of clinical applications in the delivery of a fluidal substance. Moreover, it is anticipated that the systems described herein may be formed and/or constructed of materials generally recognized to be suitable for medical use, and may include disposable materials, or reusable materials, or a combination of both in the construction of components of the system.

It should be understood that the medium delivery modulation devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain. In addition, any feature disclosed with respect to one embodiment may be incorporated in another embodiment, and vice-versa.

What is claimed is:

1. A system for modulating delivery of a fluid medium to a selected site within a patient's body, the system comprising:
   a syringe for injecting the fluid medium, the syringe comprising a chamber for receiving the fluid medium therein;
   a delivery catheter comprising a conduit for delivering the fluid medium from outside of the body to the selected site within the body;
   a flow diverter assembly disposed in a fluid medium flow path between the syringe and the delivery catheter, the flow diverter assembly configured to simultaneously divert at least some of the fluid medium within the chamber of the syringe away from the delivery of the medium through the delivery catheter conduit during injecting with the syringe, and wherein the flow diverter assembly creates increasing medium fluid flow resistance with increasing pressure level of the fluid medium passing into the flow diverter assembly; and
   a fluid coupling element having a lumen therethrough, wherein the coupling element includes:
      a first medium port fluidly coupled to the flow diverter assembly,
      a second medium port fluidly coupled to the syringe, and
      a third medium port fluidly coupled to the delivery catheter;
   wherein the flow diverter assembly comprises a valve operably connected to the coupling element;
   wherein the coupling element is a stopcock that comprises a diverter arm, and wherein the valve comprises:
      a valve housing attached to the diverter arm, wherein the valve housing and the diverter arm define an internal chamber therein, the internal chamber having a longitudinal axis therethrough, wherein the valve housing comprises a cylindrical pocket, the valve further comprising a valve compression plate disposed in the cylindrical pocket; and a diffuser received within the internal chamber, the diffuser being movable along the longitudinal axis, wherein the diffuser comprises a radial shoulder, the valve further comprising a deformable o-ring disposed between the radial shoulder and a face of the valve compression plate, wherein the face of the valve compression plate comprises a discontinuity, wherein:

the valve compression plate comprises an inner opening and an outer circumferential face; and the discontinuity is in the form of a first groove channel that extends radially between the inner opening and an outer circumferential face.

2. The system of claim 1, wherein the first groove channel is wider at the outer circumferential face than at the inner opening.

3. The system of claim 2, wherein the discontinuity further comprises a second groove channel disposed within the first groove channel, wherein the second groove channel is deeper than the first groove channel.

* * * * *